(12) United States Patent
Keating et al.

(10) Patent No.: US 7,297,489 B2
(45) Date of Patent: *Nov. 20, 2007

(54) **MUTATIONS IN AND GENOMIC STRUCTURE OF *HERG*—A LONG QT SYNDROME GENE**

(75) Inventors: Mark Keating, Brookline, MA (US); Igor Splawski, Alston, MA (US)

(73) Assignee: University of Utah Research Foundation, Salt Lake City, UT (US)

( * ) Notice: Subject to any disclaimer, the term of this patent is extended or adjusted under 35 U.S.C. 154(b) by 399 days.

This patent is subject to a terminal disclaimer.

(21) Appl. No.: 10/696,708

(22) Filed: Oct. 30, 2003

(65) Prior Publication Data

US 2004/0078833 A1 Apr. 22, 2004

Related U.S. Application Data

(60) Continuation of application No. 09/735,995, filed on Dec. 14, 2000, now abandoned, which is a division of application No. 09/226,012, filed on Jan. 6, 1999, now Pat. No. 6,207,383, which is a continuation-in-part of application No. 09/122,847, filed on Jul. 27, 1998, now abandoned.

(51) Int. Cl.
*C12Q 1/68* (2006.01)
*C12N 15/85* (2006.01)
*C07H 21/04* (2006.01)

(52) U.S. Cl. .................. 435/6; 536/24.33; 435/325

(58) Field of Classification Search ............... None
See application file for complete search history.

(56) References Cited

U.S. PATENT DOCUMENTS 5,599,673 A   2/1997  Keating et al.
6,207,383 B1* 3/2001  Keating et al. ............ 435/6

OTHER PUBLICATIONS

Itoh et al (Human Genetics, 1998, vol. 102, pp. 435-439).*
Ackerman, M.J., M.D., Ph.D., "The Long QT Syndrome: Ion Channel Diseases of the Heart", *Mayo Clin. Proc.* 1998; 73:250-269.
Akimoto, K., et al., "Novel Missense Mutation (G601S) of HERG in a Japanese Long QT Syndrome Family", *Human Mutation* Supplement 1998; 1:S184-S186.
Babij, P., et al., "Inhibition of Cardiac Delayed Rectifier K$^+$Current by Overexpression of the Long-QT Syndrome HERG G628S Mutation in Transgenic Mice", *Circ. Res.* 1998; 83(6):668-678.
Benson, D., et al., "Missense Mutation in the Pore Region of *HERG* Causes Familial Long QT Syndrome", *Circulation* May 15, 1996; 93(10):1791-1795.
Curran, M., et al., "A Molecular Basis for Cardiac Arrhythmia: *HERG* Mutations Cause Long QT Syndrome", *Cell* Mar. 10, 1995; 80:795-803.

Dausse, E., et al., "A mutation in HERG Associated with Notched T Waves in Long QT Syndrome", *J. Mol. Cell Cardiol.* 1996; 28:1609-1615.
Fung, D., et al., "Rsal and Mael intragenic RFLPs in the human HERG gene", *Clin. Genet.* 1998; 53:504.
Itoh, T., et al., "Genomic organization and mutational analysis of *HERG*, a gene responsible for familial long QT syndrome", *Hum. Genet.* 1998; 103:290-294.
Janse, M.J. and Wilde, A.A.M., "Molecular Mechanisms of Arrhythmias", *Rev. Port. Cardiol.* 1998; 17(Supl. II):41-46.
Jiang, C., et al., "Two long QT syndrome loci map to chromosomes 3 and 7 with evidence for further heterogeneity", *Nature Genetics* Oct. 1994; 8:141-147.
Keating, M.T., MD, "Genetic Approaches to Cardiovascular Disease Supravalvular Aortic Stenosis, Williams Syndrome, and Long-QT Syndrome", *Circulation* 1995;92(1):142-147.
Keating, , M.T., "The Long QT Syndrome A Review of Recent Molecular Genetic and Physiologic Discoveries", *Medicine* 1996; 75(1):1-5.
Kupershmidt, S., et al., "A K$^+$Channel Splice Variant Common in Human Heart Lacks a C-terminal Domain Required for Expression of Rapidly Activating Delayed Rectifier Current", *J. Biol. Chem.* Oct. 16, 1998 273(42):27231-27235.
Lazzara, R., "Mechanisms and management of congenital and acquired long QT syndromes", *Arch. Mal. Coeur Vass.* 1996; 89(Spec. No. 1)51-55.
Locati, E.H., et al., "Age-and Sex-Related Differences in Clinical Manifestations in Patients With Congenital Long-QT Syndrome", *Circulation* Jun. 9, 1998; 97(22):2237-2244.
London, B., et al., "Two Isoforms of the Mouse *Ether-a-go-go*-Related Gene Coassemble to Form Channels With Properties Similar to the Rapidly Activating Component of the Cardiac Delayed Rectifier K$^+$Current", *Circ. Res.* Nov. 1997; 81(5):870-878.
McDonald, T., et al., "A minK-HERG complex regulates the cardiac potassium current $I_{Kr}$", *Nature* Jul. 17, 1997; 388:289-292.
Roden, D.M., et al., "Multiple Mechanisms in the Long-QT Syndrome", *Circulation* 1996; 94(8):1996-2012.
Roden, D.M., et al., "Recent Advances in Understanding the Molecular Mechanisms of the Long QT Syndrome", *J. Cardiovasc. Electrophysiol.* Nov. 1995; 6(11)1023-1031.

(Continued)

*Primary Examiner*—Celine Qian
(74) *Attorney, Agent, or Firm*—Rothwell, Figg, Ernst & Manbeck p.c.

(57) ABSTRACT

The invention relates to the determination of the genomic structure of HERG which is a gene associated with long QT syndrome. The sequences of the 15 intron/exon junctions has been determined and this information is useful in devising primers for amplifying and sequencing across all of the exons of the gene. This is useful for determining the presence or absence of mutations which are known to cause long QT syndrome. Also disclosed are many new mutations in HERG which have been found to be associated with long QT syndrome.

7 Claims, 21 Drawing Sheets

OTHER PUBLICATIONS

Sanguinetti, M.C., et al., "A Mechanistic Link between an Inherited and an Acquired Cardiac Arrhythmia: *HERG* Encodes the $I_{Kr}$ Potassium Channel", *Cell* Apr. 21, 1995; 81:229-307.

Satler, C., et al., "Multiple different missense mutations in the pore region of *HERG* in patients with long QT syndrome", *Hum. Genet.* 1998; 102:265-272.

Salter, C., et al., "Novel Missense Mutation in the Cyclic Nucleotide-Binding Domain of *HERG* Causes Long QT Syndrome", *American Journal of Medical Genetics* 1996; 65:27-35.

Schönherr, R., et al., "Molecular determinants for activation and inactivation of HERG, a human inward rectifier potassium channel", *Journal of Physiology* 1996; 493.3:635-342.

Schulze-Bahr, E., et al., "Autosomal Recessive long-QT syndrome (Jervell Lange-Nielsen syndrome) is genetically heterogeneous", *Hum. Genet.* 1997; 100:573-576.

Schwartz, P., et al., "Long QT Syndrome Patients With Mutations of the *SCN5A* and *HERG* Genes Have Differential Responses to Na$^+$Channel Blockade and to Increases in Heart Rate", *Circulation* Dec. 15, 1995; 92(12):3381-3386.

Splawski, I., et al., "Genomic Structure of Three Long QT Syndrome Genes: *KVLQT1, HERG* and *KCNE1*", *Genomics* 1998; 51:86-97.

Tanaka, T., et al., "Four Novel *KVLQT1* and Four Novel *HERG* Mutations in Familial Long-QT Syndrome", *Circulation* Feb. 4, 1997; 95(3):565-567.

Trudeau, M., et al., "HERG, a Human Inward Rectifier in the Voltage-Gated Potassium Channel Family", *Science* Jul. 7, 1995; 269:92-95, 1087.

Vincent, G.M. MD, "The Molecular Genetics of The Long QT Syndrome: Genes Causing Fainting and Sudden Death", *Annu. Rev. Med* 1998; 49;263-74.

van den Berg, M., et al., "The long QT syndrome: a novel missense mutation in the S6 region of the KVLQT1 gene", *Hum. Genet.* 1997; 100:356-361.

Wang, Q., et al., "Genetics, molecular mechanisms and management of long QT syndrome", *Ann. Med.* 1998; 30:58-65.

Wang, Q., et al., "The molecular basis of long QT syndrome and prospects for therapy", *Mol. Med. Today* Sep. 1998; 4(9):382-388.

Wang, Q., et al., "Molecular genetica of long QT syndrome from gene to patients", *Curr. Opin. Cardiol.* 1997; 12:310-320.

Warmke, J.W. et al., "A family of potassium channel gene related to *eag* in *Drosophila* and mammals" *Proc. Natl. Acad. Sci. USA* 91:3439-3442 (1994).

Waltanasirichaigoon, D., and Beggs, A.H., "Molecular genetics of long-QT syndrome", *Curr. Opin. Pediatr.* 1998; 10:628-634.

Zareba, W., et al., "Influence of the Genotype on the Clinical Course of the Long-QT Syndrome", *N. Eng. J. Med.* Oct. 1998; 339(14):960-965.

Zhou, Z., et al., "HERG Channel Cysfunction in Human Long QT Syndrome", *J. Biol. Chem.* Aug. 14, 1998; 273(33):21061-21066.

Zou, A., et al., "A mutation in the pore region of HERG K$^+$channels expressed in *Xenopus oocytes* reduces rectification by shifting the voltage dependence of inactivation", *Journal of Physiology*, 1998; 509.1:129-137.

Omim Entry 152427—Long QT Syndrome, Type 2; LQT2 7pp., no date.

* cited by examiner

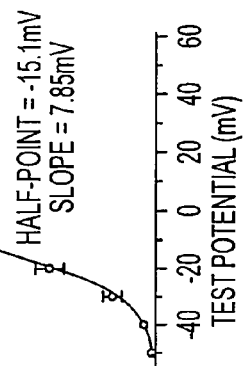
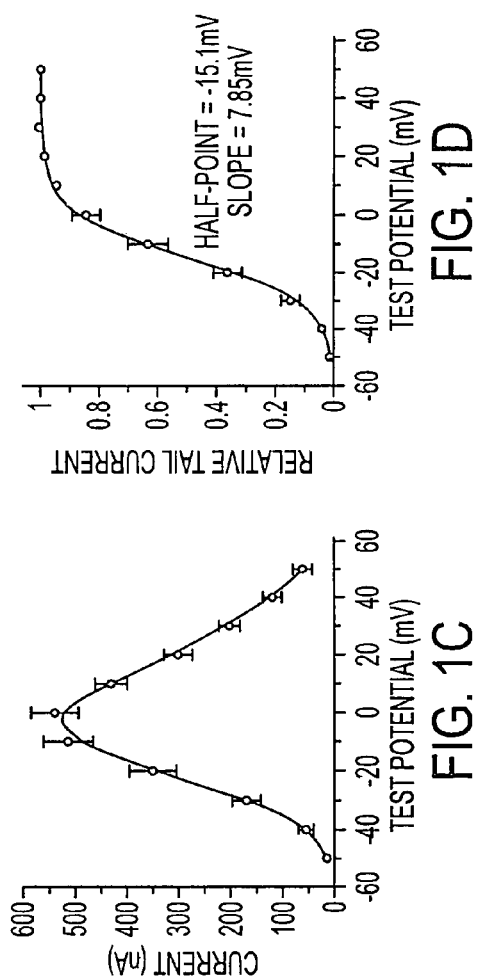
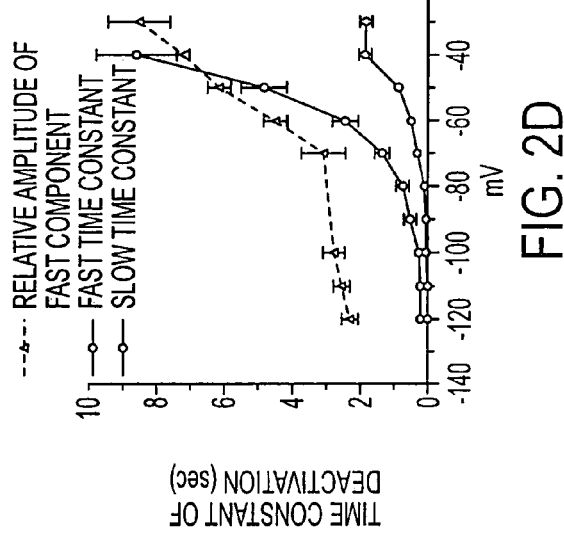
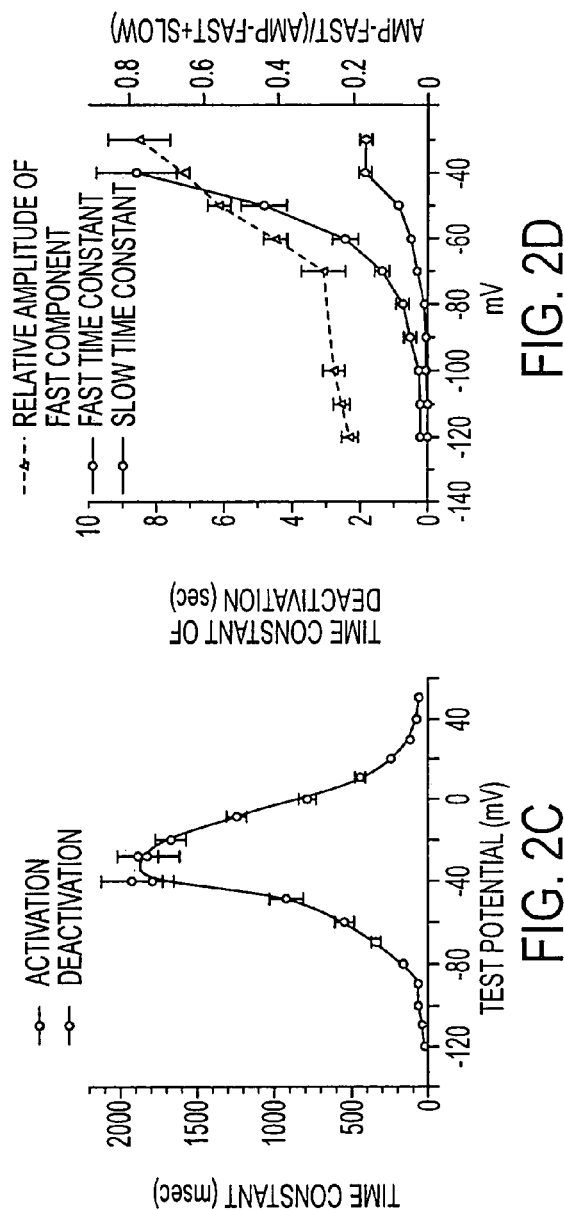

```
AGCCTAGTGCTGGGCCGGGCCGGGCCGGGGTGGGTGGGGGCCCGCCCGGCCGCCCATGGGCTCAGGATGCCGGTGCGGAGG-81
                                                        ▽    M  P  V  R  R  -5
GGCCACGTCGCGCCGCAGAACACCTTCCTGGACACCATCATCCGCAAGTTTGAGGGCCAGAGCCGTAAGTTCATCATCGCC-162
 G  H  V  A  P  Q  N  T  F  L  D  T  I  I  R  K  F  E  G  Q  S  R  K  F  I  I  A -32
AACGCTCGGGTGGAGAACTGCGCCGTCATCTACTGCAACGACGGCTTCTGCGAGCTGTGCGGCTACTCGCGGGCCGAGGTG-243
 N  A  R  V  E  N  C  A  V  I  Y  C  N  D  G  F  C  E  L  C  G  Y  S  R  A  E  V -59
ATGCAGCGACCCTGCACCTGCGACTTCCTGCACGGGCCGCGCACGCAGCGCCGCGCTGCCGCGCAGATCGCGCAGGCACTG-324
 M  Q  R  P  C  T  C  D  F  L  H  G  P  R  T  Q  R  R  A  A  A  Q  I  A  Q  A  L -86
                                              ▽
CTGGGCGCCGAGGAGCGCAAAGTGGAAATCGCCTTCTACCGGAAAGATGGGAGCTGCTTCCTATGTCTGGTGGATGTGGTG-405
 L  G  A  E  E  R  K  V  E  I  A  F  Y  R  K  D  G  S  C  F  L  C  L  V  D  V  V -113
CCCGTGAAGAACGAGGATGGGGCTGTCATCATGTTCATCCTCAATTTCGAGGTGGTGATGGAGAAGGACATGGTGGGGTCC-486
 P  V  K  N  E  D  G  A  V  I  M  F  I  L  N  F  E  V  V  M  E  K  D  M  V  G  S -140
                                              ▽
CCGGCTCATGACACCAACCACCGGGGCCCCCCCACCAGCTGGCTGGCCCCAGGCCGCGCCAAGACCTTCCGCCTGAAGCTG-567
 P  A  H  D  T  N  H  R  G  P  P  T  S  W  L  A  P  G  R  A  K  T  F  R  L  K  L -167
CCCGCGCTGCTGGCGCTGACGGCCCGGGAGTCGTCGGTGCGGTCGGGCGGCGCGGGCGGCGCGGGCGCCCCGGGGGCCGTG-648
 P  A  L  L  A  L  T  A  R  E  S  S  V  R  S  G  G  A  G  G  A  G  A  P  G  A  V -194
GTGGTGGACGTGGACCTGACGCCCGCGGCACCCAGCAGCGAGTCGCTGGCCCTGGACGAAGTGACAGCCATGGACAACCAC-729
 V  V  D  V  D  L  T  P  A  A  P  S  S  E  S  L  A  L  D  E  V  T  A  M  D  N  H -221
GTGGCAGGGCTCGGGCCCGCGGAGGAGCGGCGTGCGCTGGTGGGTCCCGGCTCTCCGCCCCGCAGCGCGCCCGGCCAGCTC-810
 V  A  G  L  G  P  A  E  E  R  R  A  L  V  G  P  G  S  P  P  R  S  A  P  G  Q  L -248
CCATCGCCCCGGGCGCACAGCCTCAACCCCGACGCCTCGGGCTCCAGCTGCAGCCTGGCCCGGACGCGCTCCCGAGAAAGC-891
 P  S  P  R  A  H  S  L  N  P  D  A  S  G  S  S  C  S  L  A  R  T  R  S  R  E  S -275
TGCGCCAGCGTGCGCCGCGCCTCGTCGGCCGACGACATCGAGGCCATGCGCGCCGGGGTGCTGCCCCCGCCACCGCGCCAC-972
 C  A  S  V  R  R  A  S  S  A  D  D  I  E  A  M  R  A  G  V  L  P  P  P  P  R  H -302
       ▽
GCCAGCACCGGGGCCATGCACCCACTGCGCAGCGGCTTGCTCAACTCCACCTCGGACTCCGACCTCGTGCGCTACCGCACC-1053
 A  S  T  G  A  M  H  P  L  R  S  G  L  L  N  S  T  S  D  S  D  L  V  R  Y  R  T -329
ATTAGCAAGATTCCCCAAATCACCCTCAACTTTGTGGACCTCAAGGGCGACCCCTTCTTGGCTTCGCCCACCAGTGACCGT-1134
 I  S  K  I  P  Q  I  T  L  N  F  V  D  L  K  G  D  P  F  L  A  S  P  T  S  D  R -356
                                                             ▽
GAGATCATAGCACCTAAGATAAAGGAGCGAACCCACAATGTCACTGAGAAGGTCACCCAGGTCCTGTCCCTGGGCGCCGAC-1215
 E  I  I  A  P  K  I  K  E  R  T  H  N  V  T  E  K  V  T  Q  V  L  S  L  G  A  D -383
GTGCTGCCTGAGTACAAGCTGCAGGCACCGCGCATCCACCGCTGGACCATCCTGCATTACAGCCCCTTCAAGGCCGTGTGG-1296
 V  L  P  E  Y  K  L  Q  A  P  R  I  H  R  W  T  I  L  H  Y  S  P  F  K  A  V  W -410
GACTGGCTCATCCTGCTGCTGGTCATCTACACGGCTGTCTTCACACCCTACTCGGCTGCCTTCCTGCTGAAGGAGACGGAA-1377
 D  W  L  I  L  L  L  V  I  Y  T  A  V  F  T  P  Y  S  A  A  F  L  L  K  E  T  E -437
 ─ ─  ─  ─  ─  ─  ─  ─  ─  ─  ─  ─  ─
      S1
GAAGGCCCGCCTGCTACCGAGTGTGGCTACGCCTGCCAGCCGCTGGCTGTGGTGGACCTCATCGTGGACATCATGTTCATT-1458
 E  G  P  P  A  T  E  C  G  Y  A  C  Q  P  L  A  V  V  D  L  I  V  D  I  M  F  I -464
                                          ─  ─  ─  ─  ─  ─  ─  ─  ─  ─  ─  ─  ─
                                                      S2
GTGGACATCCTCATCAACTTCCGCACCACCTACGTCAATGCCAACGAGGAGGTGGTCAGCCACCCCGGCCGCATCGCCGTC-1539
 V  D  I  L  I  N  F  R  T  T  Y  V  N  A  N  E  E  V  V  S  H  P  G  R  I  A  V -491
 ─  ─  ─  ─  ─  ─  ─
CACTACTTCAAGGGCTGGTTCCTCATCGACATGGTGGCCGCCATCCCCTTCGACCTGCTCATCTTCGGCTCTGGCTCTGAG-1620
 H  Y  F  K  G  W  F  L  I  D  M  V  A  A  I  P  F  D  L  L  I  F  G  S  G  S  E -518
       ▽           ─  ─  ─  ─  ─  ─  ─  ─  ─  ─  ─  ─  ─  ─
                                    S3
GAGCTGATCGGGCTGCTGAAGACTGCGCGGCTGCTGCGGCTGGTGCGCGTGGCGCGGAAGCTGGATCGCTACTCAGAGTAC-1701
 E  L  I  G  L  L  K  T  A  R  L  L  R  L  V  R  V  A  R  K  L  D  R  Y  S  E  Y -545
    ─  ─  ─  ─  ─  ─  ─  ─  ─  ─  ─  ─  ─  ─
                S4
GGCGCGGCCGTGCTGTTCTTGCTCATGTGCACCTTTGCGCTCATCGCGCACTGGCTAGCCTGCATCTGGTACGCCATCGGC-1782
 G  A  A  V  L  F  L  L  M  C  T  F  A  L  I  A  H  W  L  A  C  I  W  Y  A  I  G -572
       ─  ─  ─  ─  ─  ─  ─  ─  ─  ─  ─  ─  ─  ─  ─  ─
               S5
AACATGGAGCAGCCACACATGGACTCACGCATCGGCTGGCTGCACAACCTGGGCGACCAGATAGGCAAACCCTACAACAGC-1863
 N  M  E  Q  P  H  M  D  S  R  I  G  W  L  H  N  L  G  D  Q  I  G  K  P  Y  N  S -599
AGCGGCCTGGGCGGCCCCTCCATCAAGGACAAGTATGTGACGGCGCTCTACTTCACCTTCAGCAGCCTCACCAGTGTGGGC-1944
 S  G  L  G  G  P  S  I  K  D  K  Y  V  T  A  L  Y  F  T  F  S  S  L  T  S  V  G -626
                                  ─  ─  ─  ─  ─  ─  ─  ─  ─  ─  ─  ─  ─  ─
                                               Pore   ▽
TTCGGCAACGTCTCTCCCAACACCAACTCAGAGAAGATCTTCTCCATCTGCGTCATGCTCATTGGCTCCCTCATGTATGCT-2025
 F  G  N  V  S  P  N  T  N  S  E  K  I  F  S  I  C  V  M  L  I  G  S  L  M  Y  A -653
 ─  ─  ─  ─  ─                 ─  ─  ─  ─  ─  ─  ─  ─  ─  ─  ─  ─  ─  ─  ─
                                                S6
```

FIG. 8A

```
AGCATCTTCGGCAACGTGTCGGCCATCATCCAGCGGCTGTACTCGGGCACAGCCCGCTACCACACACAGATGCTGCGGGTG-2106
 S  I  F  G  N  V  S  A  I  I  Q  R  L  Y  S  G  T  A  R  Y  H  T  Q  M  L  R  V  -680
CGGGAGTTCATCCGCTTCCACCAGATCCCCAATCCCCTGCGCCAGCGCCTCGAGGAGTACTTCCAGCACGCCTGGTCCTAC-2187
 R  E  F  I  R  F  H  Q  I  P  N  P  L  R  Q  R  L  E  E  Y  F  Q  H  A  W  S  Y  -707
                           ▽
ACCAACGGCATCGACATGAACGCGGTGCTGAAGGGCTTCCCTGAGTGCCTGCAGGCTGACATCTGCCTGCACCTGAACCGC-2268
 T  N  G  I  D  M  N  A  V  L  K  G  F  P  E  C  L  Q  A  D  I  C  L  H  L  N  R  -734
TCACTGCTGCAGCACTGCAAACCCTTCCGAGGGGCCACCAAGGGCTGCCTTCGGGCCCTGGCCATGAAGTTCAAGACCACA-2349
 S  L  L  Q  H  C  K  P  F  R  G  A  T  K  G  C  L  R  A  L  A  M  K  F  K  T  T  -761
CATGCACCGCCAGGGGACACACTGGTGCATGCTGGGGACCTGCTCACCGCCCTGTACTTCATCTCCCGGGGCTCCATCGAG-2430
 H  A  P  P  G  D  T  L  V  H  A  G  D  L  L  T  A  L  Y  F  I  S  R  G  S  I  E  -788
                              ▽
ATCCTGCGGGGCGACGTCGTCGTGGCCATCCTGGGGAAGAATGACATCTTTGGGGAGCCTCTGAACCTGTATGCAAGGCCT-2511
 I  L  R  G  D  V  V  V  A  I  L  G  K  N  D  I  F  G  E  P  L  N  L  Y  A  R  P  -815
                                 cNBD
GGCAAGTCGAACGGGGATGTGCGGGCCCTCACCTACTGTGACCTACACAAGATCCATCGGGACGACCTGCTGGAGGTGCTG-2592
 G  K  S  N  G  D  V  R  A  L  T  Y  C  D  L  H  K  I  H  R  D  D  L  L  E  V  L  -842
                                                                  ▽
GACATGTACCCTGAGTTCTCCGACCACTTCTGGTCCAGCCTGGAGATCACCTTCAACCTGCGAGATACCAACATGATCCCG-2673
 D  M  Y  P  E  F  S  D  H  F  W  S  S  L  E  I  T  F  N  L  R  D  T  N  M  I  P  -869
GGCTCCCCCGGCAGTACGGAGTTAGAGGGTGGCTTCAGTCGGCAACGCAAGCGCAAGTTGTCCTTCCGCAGGCGCACGGAC-2754
 G  S  P  G  S  T  E  L  E  G  G  F  S  R  Q  R  K  R  K  L  S  F  R  R  R  T  D  -896
 ▽
AAGGACACGGAGCAGCCAGGGGAGGTGTCGGCCTTGGGGCCGGGCCGGGCGGGGGCAGGGCCGAGTAGCCGGGGCCGGCCG-2835
 K  D  T  E  Q  P  G  E  V  S  A  L  G  P  G  R  A  G  A  G  P  S  S  R  G  R  P  -923
GGGGGGCCGTGGGGGGAGAGCCCGTCCAGTGGCCCCTCCAGCCCTGAGAGCAGTGAGGATGAGGGCCCAGGCCGCAGCTCC-2916
 G  G  P  W  G  E  S  P  S  S  G  P  S  S  P  E  S  S  E  D  E  G  P  G  R  S  S  -950
AGCCCCCTCCGCCTGGTGCCCTTCTCCAGCCCCAGGCCCCCCGGAGAGCCGCCGGGTGGGGAGCCCCTGATGGAGGACTGC-2997
 S  P  L  R  L  V  P  F  S  S  P  R  P  P  G  E  P  P  G  G  E  P  L  M  E  D  C  -977
                                ▽
GAGAAGAGCAGCGACACTTGCAACCCCCTGTCAGGCGCCTTCTCAGGAGTGTCCAACATTTTCAGCTTCTGGGGGGACAGT-3078
 E  K  S  S  D  T  C  N  P  L  S  G  A  F  S  G  V  S  N  I  F  S  F  W  G  D  S  -1004
CGGGGCCGCCAGTACCAGGAGCTCCCTCGATGCCCCGCCCCCACCCCCAGCCTCCTCAACATCCCCCTCTCCAGCCCGGGT-3159
 R  G  R  Q  Y  Q  E  L  P  R  C  P  A  P  T  P  S  L  L  N  I  P  L  S  S  P  G  -1031
                                                                      ▽
CGGCGGCCCCGGGGCGACGTGGAGAGCAGGCTGGATGCCCTCCAGCGCCAGCTCAACAGGCTGGAGACCCGGCTGAGTGCA-3240
 R  R  P  R  G  D  V  E  S  R  L  D  A  L  Q  R  Q  L  N  R  L  E  T  R  L  S  A  -1058
GACATGGCCACTGTCCTGCAGCTGCTACAGAGGCAGATGACGCTGGTCCCGCCCGCCTACAGTGCTGTGACCACCCCGGGG-3321
 D  M  A  T  V  L  Q  L  L  Q  R  Q  M  T  L  V  P  P  A  Y  S  A  V  T  T  P  G  -1085
                                                                   ▽
CCTGGCCCCACTTCCACATCCCCGCTGTTGCCCGTCAGCCCCCTCCCCACCCTCACCTTGGACTCGCTTTCTCAGGTTTCC-3402
 P  G  P  T  S  T  S  P  L  L  P  V  S  P  L  P  T  L  T  L  D  S  L  S  Q  V  S  -1112
CAGTTCATGGCGTGTGAGGAGCTGCCCCCGGGGGCCCCAGAGCTTCCCCAAGAAGGCCCCACACGACGCCTCTCCCTACCG-3483
 Q  F  M  A  C  E  E  L  P  P  G  A  P  E  L  P  Q  E  G  P  T  R  R  L  S  L  P  -1139
GGCCAGCTGGGGGCCCTCACCTCCCAGCCCCTGCACAGACACGGCTCGGACCCGGGCAGTTAGTGGGGCTGCCCAGTGTGG-3564
 G  Q  L  G  A  L  T  S  Q  P  L  H  R  H  G  S  D  P  G  S  *                     -1159
ACACGTGGCTCACCCAGGGATCAAGGCGCTGCTGGGCCGCTCCCCTTGGAGGCCCTGCTCAGGAGGCCCTGACCGTGGAAG-3645
GGGAGAGGAACTCGAAAGCACAGCTCCTCCCCCAGCCCTTGGGACCATCTTCTCCTGCAGTCCCCTGGGCCCCAGTGAGAG-3726
GGCAGGGGCAGGGCCGGCAGTAGGTGGGGCCTGTGGTCCCCCCACTGCCCTGAGGGCATTAGCTGGTCTAACTGCCCGGA-3807
GGCACCCGGCCCTGGGCCTTAGGCACCTCAAGGACTTTTCTGCTATTTACTGCTCTTATTGTTAAGGATAATAATTAAGGA-3888
TCATATGAATAATTAATGAAGATGCTGATGACTATGAATAATAAATAATTATCCTGAGGAG(A)n            -3949
```

FIG. 8B

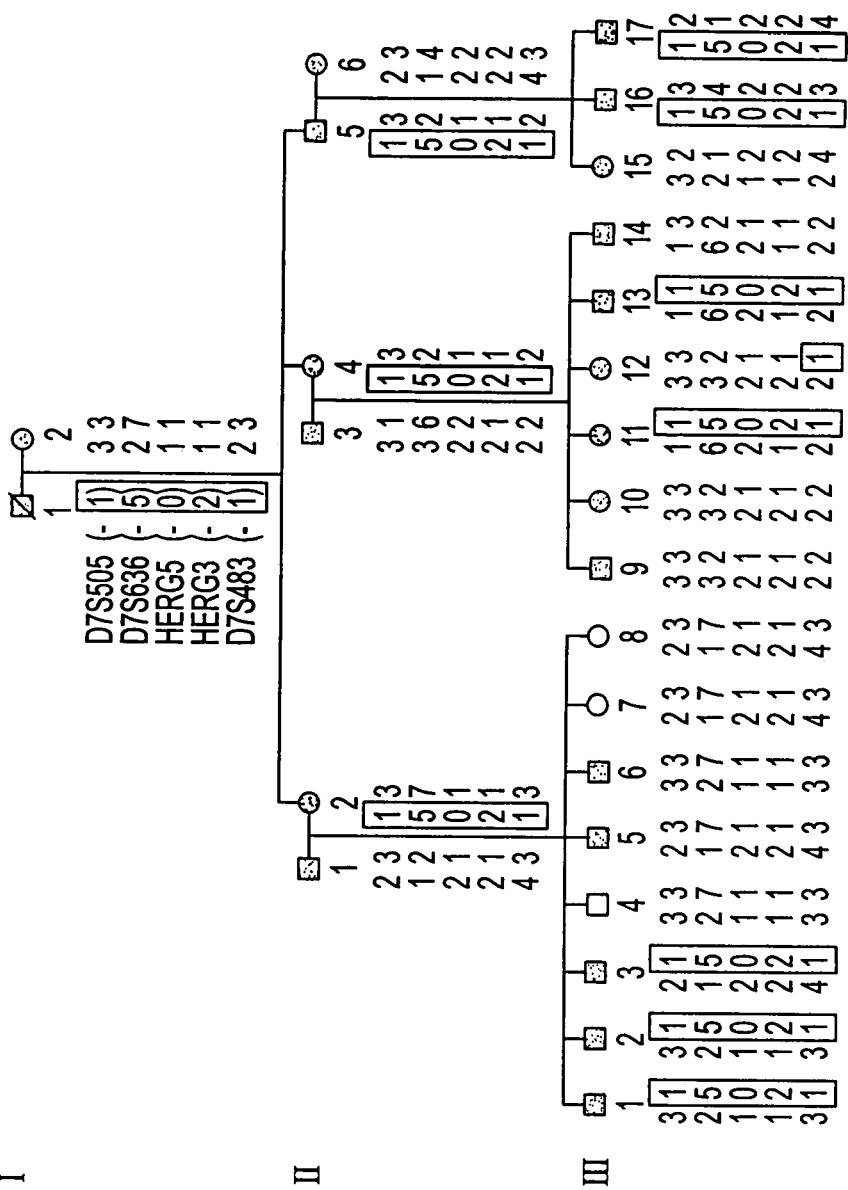
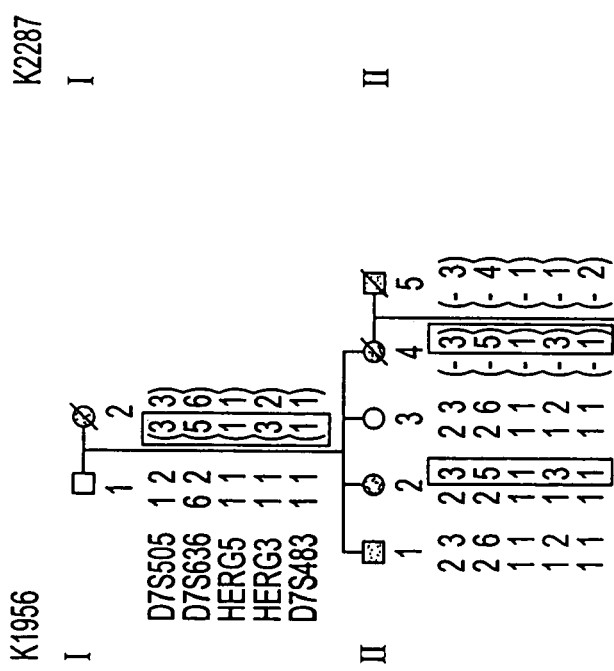
FIG. 9B
FIG. 9A

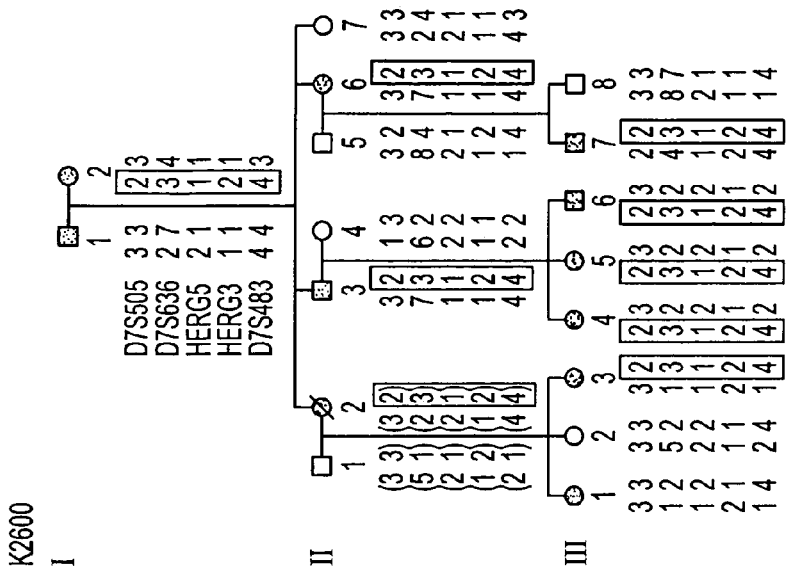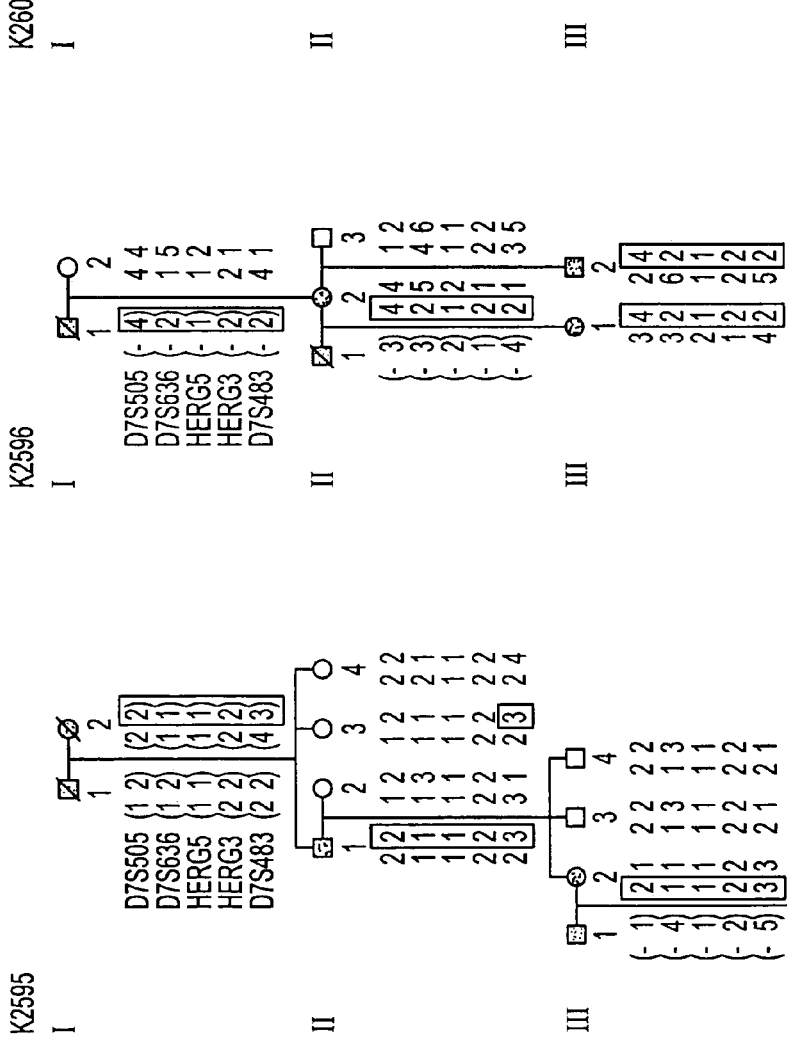
FIG. 9E
FIG. 9D
FIG. 9C

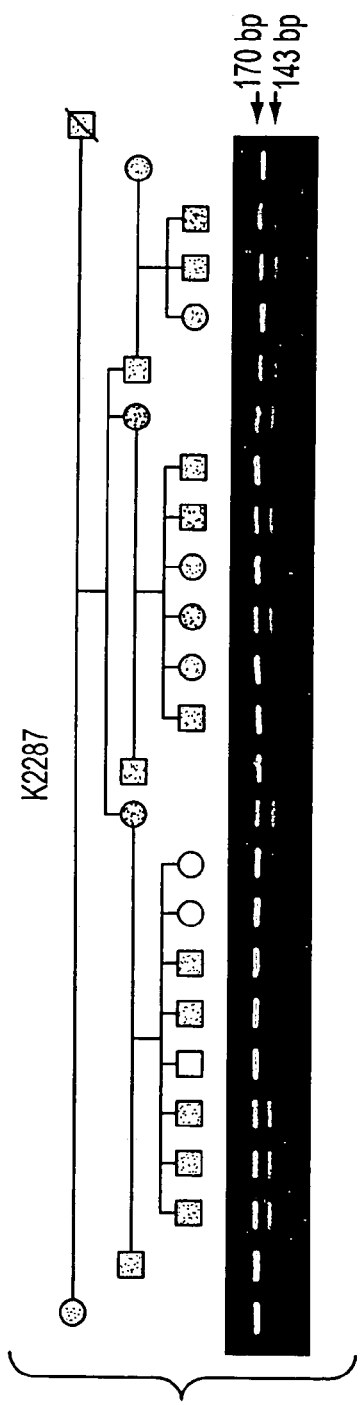
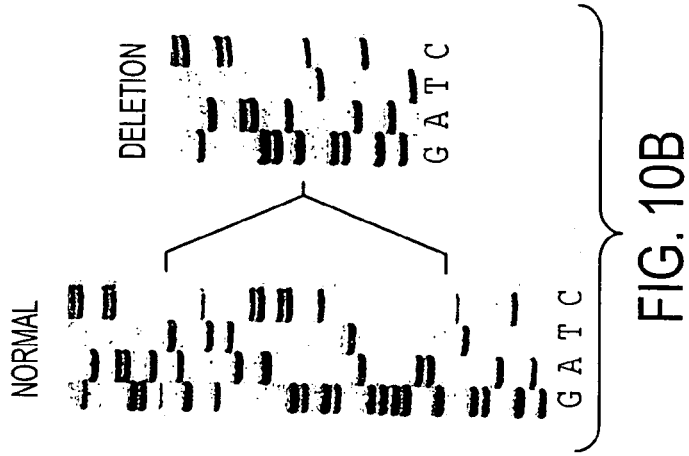
FIG. 10A
FIG. 10B

```
TGG TTC CTC ATC GAC ATG GTG GCC GCC ATC CCC TTC GAC CTG CTC    SEQ ID NO:96
 W   F   L   I   D   M   V   A   A   I   P   F   D   L   L     SEQ ID NO:97
              └─────────────────── S3 ───────────────────┘
```

FIG. 10C

```
NORMAL    GTC ATC TAC ACG GCT GTC TTC ACA CCC TAC TCG GCT GCC TTC CTG AAG GAG    SEQ ID NO:98
           V   I   Y   T   A   V   F   T   P   Y   S   A   A   F   L   K   E     SEQ ID NO:99
                          ↑
DELETION  GTC ATC TAC CGG CTG TCT TCA CAC CCT ACT CGG CTG CCT TCC TGC TGA         SEQ ID NO:100
           V   I   Y   R   L   S   S   H   P   T   R   L   P   S   C               SEQ ID NO:101
```

FIG. 11C

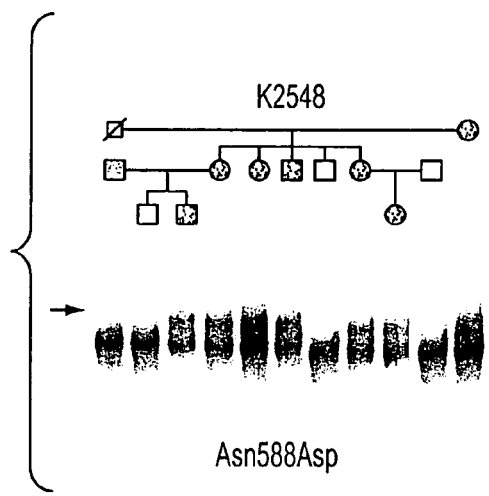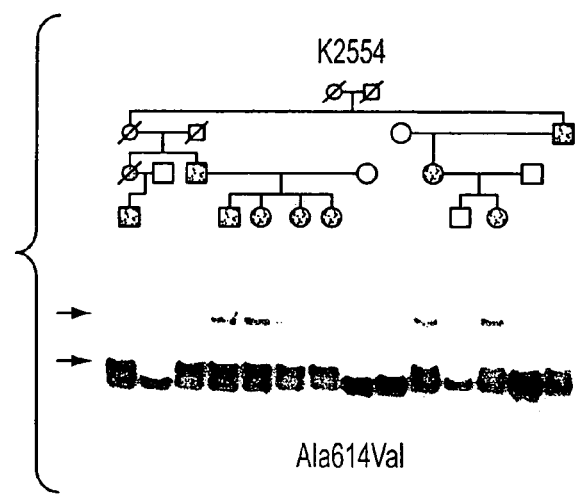
FIG. 13A  FIG. 13B
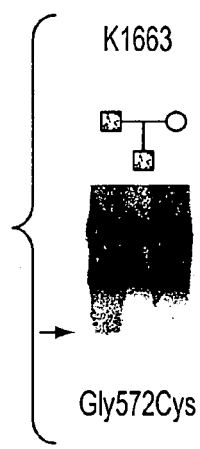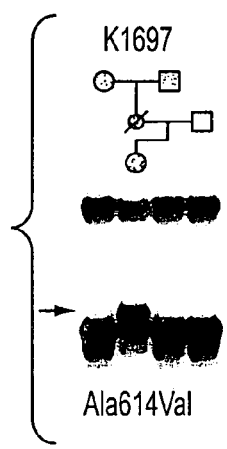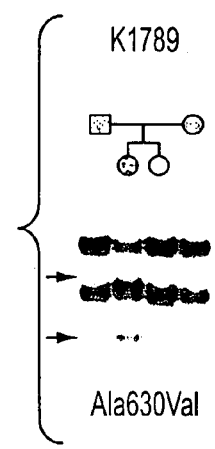
FIG. 13C  FIG. 13D  FIG. 13E

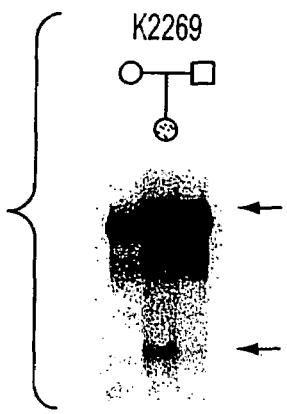
FIG. 14A
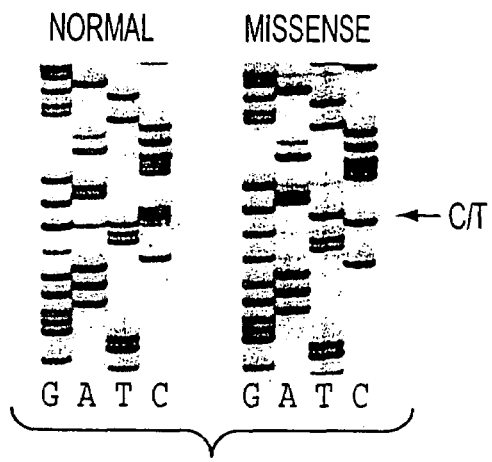
FIG. 14B
```
          AGC → S    SEQ ID
          GGC        NO:
           \/
        S V G F G N V S    112
        ←—— PORE ——→
K2269   S V G F S N V S    113
H-Erg   S V G F G N V S    112
M-Eag   S V G F G N I A    114
R-Eag   S V G F G N I A    114
Eag     S V G F G N V A    115
Elk     S V G F G N V S    112
Shaker  T V G Y G D M T    116
```
FIG. 14C

MUTATIONS IN AND GENOMIC STRUCTURE OF *HERG*—A LONG QT SYNDROME GENE

CROSS REFERENCE TO RELATED APPLICATIONS

The present application is a continuation of U.S. patent application Ser. No. 09/735,995, filed on 14 Dec. 2000 now abandoned, which in turn is a division of U.S. patent application Ser. No. 09/226,012, filed on 6 Jan. 1999, now U.S. Pat. No. 6,207,383, which in turn is a continuation-in-part of Ser. No. 09/122,847, filed 27 Jul. 1998 now abandoned, to which priority is claimed and which are incorporated herein by reference.

This application was made with Government support under Grant No. P50-HL52338-02. The federal government may have certain rights in this invention.

BACKGROUND OF THE INVENTION

The present invention is directed to a process for the diagnosis of long QT syndrome (LQT). LQT has been associated with specific genes including HERG, SCN5A, KVLQT1 and KCNE1. LQT may be hereditary and due to specific mutations in the above genes or it may be acquired, e.g., as a result of treatment with drugs given to treat cardiac arrhythmias or of treatment with other types of medications such as antihistamines or antibiotics such as erythromycin. The acquired form of LQT is the more prevalent form of the disorder. It had previously been shown that the HERG gene encodes a $K^+$ channel which is involved in the acquired form of LQT. It is shown that increasing the $K^+$ levels in patients taking drugs to prevent cardiac arrhythmias may decrease the chances of the acquired form of LQT from developing and can be used as a preventive measure. Also, this knowledge can now be used to develop drugs which may activate this $K^+$ channel and which could be given in conjunction with the drugs presently used to treat cardiac arrhythmias. Activation of the $K^+$ channel should decrease the risk of developing LQT and torsade de pointes.

The publications and other materials used herein to illuminate the background of the invention or provide additional details respecting the practice, are incorporated by reference, and for convenience are respectively grouped in the appended List of References.

Although sudden death from cardiac arrhythmias is thought to account for 11% of all natural deaths, the mechanisms underlying arrhythmias are poorly understood (Kannel, 1987; Willich et al., 1987). One form of long QT syndrome (LQT) is an inherited cardiac arrhythmia that causes abrupt loss of consciousness, syncope, seizures and sudden death from ventricular tachyarrhythmias, specifically torsade de pointes and ventricular fibrillation (Ward, 1964; Romano, 1965; Schwartz et al., 1975; Moss et al., 1991). This disorder usually occurs in young, otherwise healthy individuals (Ward, 1964; Romano, 1965; Schwartz, 1975). Most LQT gene carriers manifest prolongation of the QT interval on electrocardiograms, a sign of abnormal cardiac repolarization (Vincent et al., 1992). The clinical features of LQT result from episodic cardiac arrhythmias, specifically torsade de pointes, named for the characteristic undulating nature of the electrocardiogram in this arrhythmia. Torsade de pointes may degenerate into ventricular fibrillation, a particularly lethal arrhythmia. Although LQT is not a common diagnosis, ventricular arrhythmias are very common; more than 300,000 United States citizens die suddenly every year (Kannel et al., 1987; Willich et al., 1987) and, in many cases, the underlying mechanism may be aberrant cardiac repolarization. LQT, therefore, provides a unique opportunity to study life-threatening cardiac arrhythmias at the molecular level. A more common form of this disorder is called "acquired LQT" and it can be induced by many different factors, particularly treatment with certain medications and reduced serum $K^+$ levels (hypokalemia).

Autosomal dominant and autosomal recessive forms of the hereditary form of this disorder have been reported. Autosomal recessive LQT (also known as Jervell-Lange-Nielsen syndrome) has been associated with congenital neural deafness; this form of LQT is rare (Jervell and Lange-Nielsen, 1957). Autosomal dominant LQT (Romano-Ward syndrome) is more common, and is not associated with other phenotypic abnormalities. A disorder very similar to inherited LQT can also be acquired, usually as a result of pharmacologic therapy (Schwartz et al., 1975; Zipes, 1987).

In 1991, the complete linkage between autosomal dominant LQT and a polymorphism at HRAS was reported (Keating et al., 1991a; Keating et al., 1991b). This discovery localized LQT1 to chromosome 11p15.5 and made presymptomatic diagnosis possible in some families. Autosomal dominant LQT was previously thought to be genetically homogeneous, and the first seven families that were studied were linked to 11p15.5 (Keating et al., 1991b). In 1993, it was found that there was locus heterogeneity for LQT (Benhorin et al., 1993; Curran et al., 1993b; Towbin et al., 1994). Two additional LQT loci were subsequently identified, LQT2 on chromosome 7q35-36 (nine families) and LQT3 on 3p21-24 (three families) (Jiang et al., 1994). The genes responsible for LQT at these loci were subsequently identified. These are KVLQT1 (LQT1), HERG (LQT2), and SCN5A (LQT3) (Wang et al., 1996; Curran et al., 1995; Wang et al., 1995; U.S. Pat. No. 5,599,673). Later, KCNE1 (LQT5) was also associated with long QT syndrome (Splawski et al., 1997; Duggal et al., 1998). These genes encode ion channels involved in generation of the cardiac action potential. Mutations can lead to channel dysfunction and delayed myocellular repolarization. Because of regional heterogeneity of channel expression within the myocardium, the aberrant cardiac repolarization creates a substrate for arrhythmia. KVLQT1 and KCNE1 are also expressed in the inner ear (Neyroud et al., 1997; Vetter et. al., 1996). It has been demonstrated that homozygous or compound heterozygous mutations in each of these genes can cause deafness and the severe cardiac phenotype of the Jervell and Lange-Nielsen syndrome (Neyroud et al., 1997; Splawski et al., 1997; Schultze-Bahr et al., 1997; Tyson et al., 1997). Loss of functional channels in the ear apparently disrupts the production of endolymph, leading to deafness. Several families remain unlinked to the known loci, indicating additional locus heterogeneity for LQT. This degree of heterogeneity suggests that distinct LQT genes may encode proteins that interact to modulate cardiac repolarization and arrhythmia risk.

Presymptomatic diagnosis of LQT is currently based on prolongation of the QT interval on electrocardiograms. QTc (QT interval corrected for heart rate) greater than 0.44 second has traditionally classified an individual as affected. Most LQT patients, however, are young, otherwise healthy individuals, who do not have electrocardiograms. Moreover, genetic studies have shown that QTc is neither sensitive nor specific (Vincent et al., 1992). The spectrum of QTc intervals for gene carriers and non-carriers overlaps, leading to misclassifications. Non-carriers can have prolonged QTc intervals and be diagnosed as affected. Conversely, some LQT gene carriers have QTc intervals of ≦0.44 second but are still at increased risk for arrhythmia. Correct presymptomatic diagnosis is important for effective, gene-specific treatment of LQT.

Genetic screening using mutational analysis can improve presymptomatic diagnosis. The presence of a mutation would unequivocally distinguish affected individuals and identify the gene underlying LQT even in small families and sporadic cases. To facilitate the identification of LQT-associated mutations, we defined the genomic structure of HERG and designed primer pairs for the amplification of each exon. Single strand conformational polymorphism (SSCP) analyses identified additional mutations in HERG.

In 1994, Warmke and Ganetzky identified a novel human cDNA, human ether a-go-go related gene (HERG, Warmke and Ganetzky, 1994). HERG was localized to human chromosome 7 by PCR analysis of a somatic cell hybrid panel (Warmke and Ganetzky, 1994). The function of the protein encoded by HERG was not known, but it has predicted amino acid sequence homology to potassium channels. HERG was isolated from a hippocampal cDNA library by homology to the Drosophila ether a-go-go gene (eag), which encodes a calcium-modulated potassium channel (Bruggemann et al., 1993). HERG is not the human homolog of eag, however, sharing only ~50% amino acid sequence homology. The function of HERG was unknown, but it was strongly expressed in the heart and was hypothesized to play an important role in repolarization of cardiac action potentials and was linked to LQT (Curran et al., 1995).

Acquired LQT usually results from therapy with medications that block cardiac $K^+$ channels (Roden, 1988). The medications most commonly associated with LQT are anti-arrhythrnic drugs (e.g., quinidine, sotalol) that block the cardiac rapidly-activating delayed rectifier $K^+$ current, $I_{Kr}$, as part of their spectrum of pharmacologic activity. Other drugs may also cause acquired LQT. These include antihistamines and some antibiotics such as erythromycin. $I_{Kr}$ has been characterized in isolated cardiac myocytes (Balser et al., 1990; Follmer et al., 1992; Sanguinetti and Jurkiewicz, 1990; Shibasaki, 1987; T. Yang et al., 1994), and is known to have an important role in initiating repolarization of action potentials.

To define the physiologic role of HERG, the full-length cDNA was cloned and the channel was expressed in Xenopus oocytes. Voltage-clamp analyses of the resulting currents revealed that HERG encodes a $K^+$ channel with biophysical characteristics nearly identical to $I_{Kr}$. These data suggest that HERG encodes the major subunit for the $I_{Kr}$ channel, and provide a mechanistic link between some forms of inherited and drug-induced LQT.

SUMMARY OF THE INVENTION

The HERG genomic structure is defined showing that it comprises 15 exons and spans 55 kilobases. Primer pairs are presented which allow analysis of all 15 exons for mutations which may be associated with long QT syndrome. Many new mutations in HERG associated with long QT syndrome are also presented.

BRIEF DESCRIPTION OF THE FIGURES

FIGS. 1A-1D. Currents elicited by depolarizing voltage steps in Xenopus oocytes injected with HERG cRNA. FIG. 1A—Currents activated by 4 sec pulses, applied in 10 mV increments from −50 to −10 mV. Current during the pulse progressively increased with voltage, as did tail current upon return to the holding potential. Holding potential was −70 mV. The inset illustrates the voltage pulse protocol. FIG. 1B—Currents activated with test pulses of 0 to +40 mV, applied in 10 mV increments. Current magnitude during the pulse progressively decreased with voltage, whereas the tail current saturated at +10 mV. Note that currents do not exhibit slow inactivation. FIG. 1C—Current-voltage relationship for peak HERG current recorded during 4 sec pulses (n=10). FIG. 1D—Voltage-dependence of HERG channel activation. Amplitude of tail currents were measured at −70 mV following 4 sec pulses, then normalized relative to the largest current. Data was fit to a Boltzmann function: $I=1/(1+\exp[(V_t-V_{1/2})/k])$, where I=relative tail current, $V_t$=test potential, $V_{1/2}$ is the voltage required for half activation of current, and k is the slope factor. ($V_{1/2}$=−15.1±0.6 mV; k=7.85±0.2 mV, n=10)

FIGS. 2A-2D. Kinetics of HERG current activation and deactivation. FIG. 2A—Activating currents were activated by 3.25 sec pulses to test potentials ranging from −50 to +20 mV (10 mV steps). Currents and corresponding single exponential fits ($I=A_0+A_1 e^{-t/t}$) are superimposed. FIG. 2B—Deactivation of HERG currents. Current was activated with 1.6 sec pulses to +20 mV, followed by return to test potentials ranging from −40 to −100 mV (10 mV steps). Deactivating currents and corresponding biexponential fits ($I_{tail}=A_0+AMP_f \cdot \exp^{-t/tf}+AMP_s \cdot \exp^{-t/ts}$) are superimposed. Currents were not leak subtracted. FIG. 2C—Voltage-dependent kinetics of activation (n=15) and rapid deactivation (n=11). FIG. 2D—Plot of time constants ($t_f$, $t_s$) and relative amplitudes of the fast ($AMP_f$) and slow ($AMP_s$) components of HERG current deactivation as a function of test potential (n=11). Relative amplitudes were not determined at −80 and −90 mV due to the small current magnitudes near the reversal potential.

FIG. 3A—Tail currents were elicited at potentials of −105 to −80 mV (applied in 5 mV steps) in an oocyte bathed in ND96 solution ($[K^+]_e$=2 mM) following a pulse to +20 mV. The estimated reversal potential of tail currents was −97 mV. Currents were not leak subtracted. FIG. 3B—Tail currents were elicited at potentials of −75 to −50 mV (applied in 5 mV steps) in the same oocyte bathed in modified ND96 solution ($[K^+]_e$=10 mM). The reversal potential of tail currents was −65 mV. FIG. 3C—Reversal potential ($E_{rev}$) of HERG current varies as a function of $[K^+]_e$. $E_{rev}$ was measured for each oocyte by determining the zero-intercept from a plot of tail current amplitude as a function of test potential. Data represent the mean of 5 determinations, except for 2 mM $[K^+]_e$ (n=15). The dotted line is the relationship predicted by the Nernst equation for a perfectly $K^+$-selective channel. The solid curve represents a fit of the data to the Goldman-Hodgkin-Katz current equation (Goldman, 1943; Hodgkin and Katz, 1949): $E_{rev}=58 \cdot \log\{(r[Na^+]_e+[K^+]_e)/(r[Na^+]_i+[K^+]_i)\}$. The relative permeability of $Na^+$ to $K^+$ (r) determined from this fit was 0.007.

FIGS. 4A-C—Currents elicited by 4 sec pulses to test potentials ranging from −50 to +20 mV in an oocyte bathed in modified ND96 solution containing 10 mM KCl (A), 2 mM KCl (B), or 5 min after switching to ND96 solution with no added KCl (C). FIG. 4D—Current-voltage relationship for currents shown in panels A-C. FIG. 4E—HERG current amplitude varies as a function of $[K^+]_e$. Currents were measured at a test potential of +20 mV (n=4-6). The solid line is a linear fit to data ($I_{HERG}$=189+

37.5[K$^+$]$_e$). Note that this relationship at lower and higher [K$^+$]$_e$ would not be expected to be a linear function of [K$^+$]$_e$.

Figure 5B:
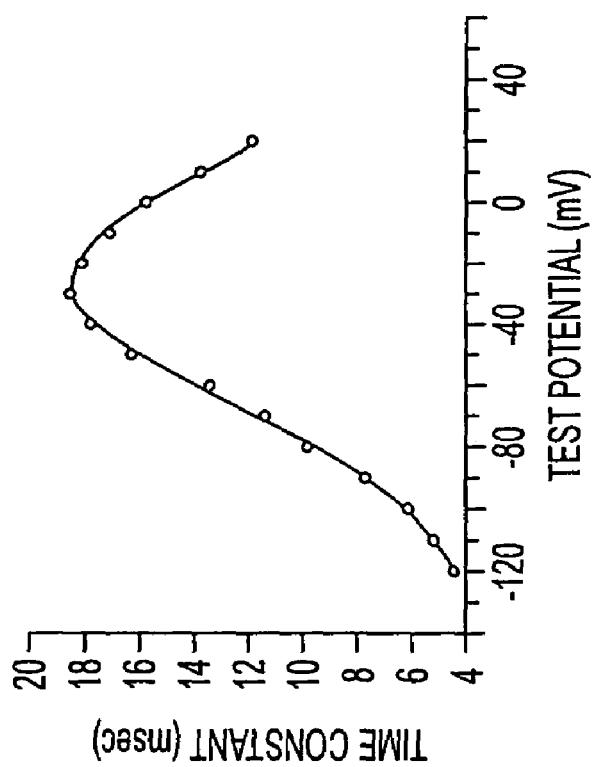
Figure 5A:
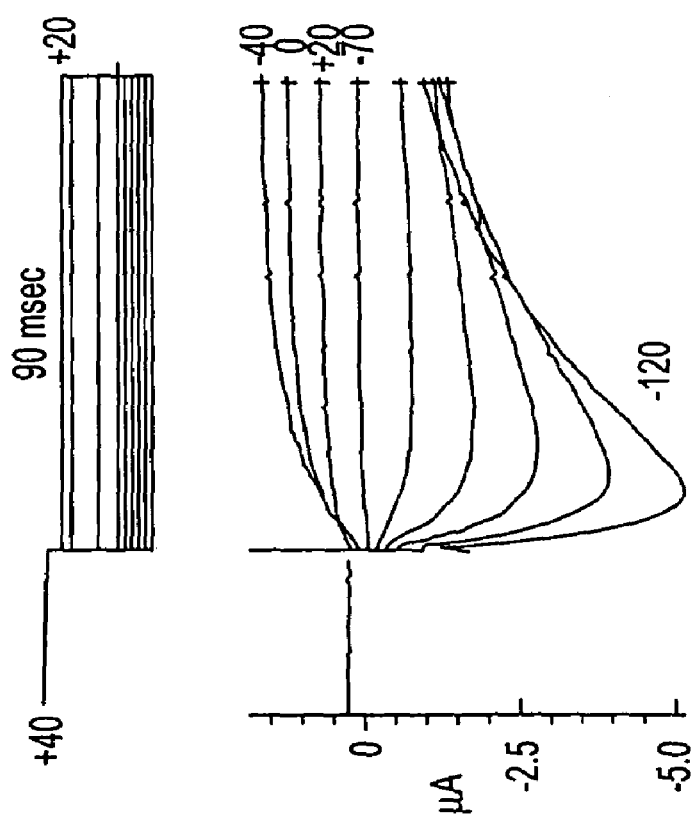
Figure 5D:
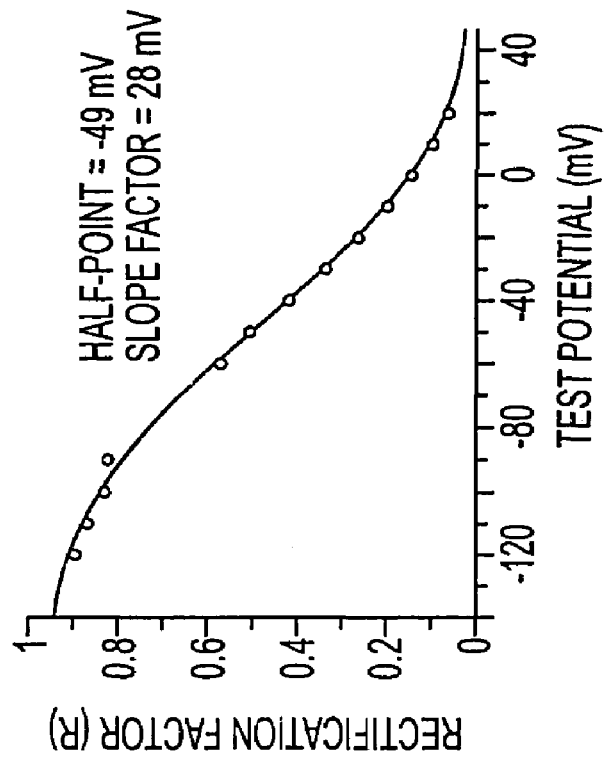
Figure 5C:
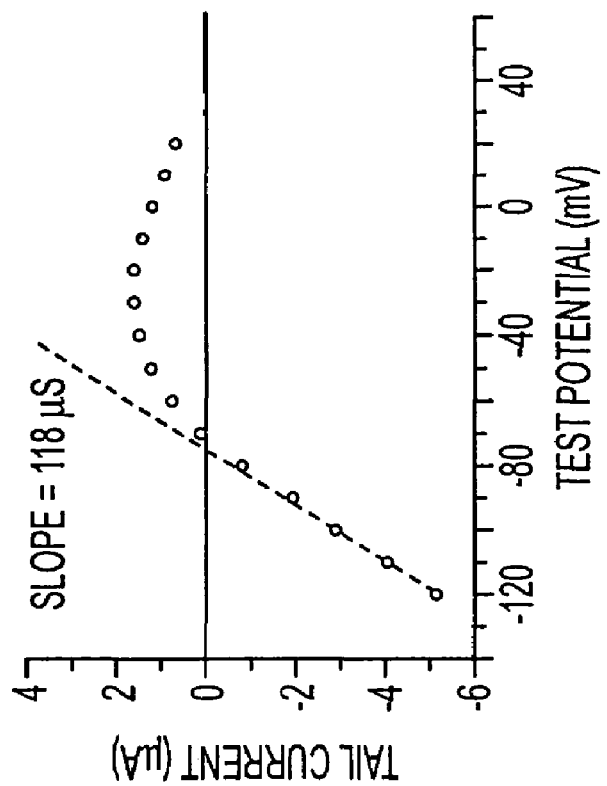

FIGS. 5A-5D. HERG rectification results from rapid inactivation. FIG. 5A—Currents recorded at test potentials of +20, 0, −40, and −70 to −120 mV (in 10 mV steps) following activation with a 260 msec pulse to +40 mV ([K$^+$]$_e$=10 mM). Currents were recorded at a sampling rate of 10 kHz. Only the final 30 msec of the activating pulse is shown, followed by the 90 msec tail current. P/3 subtraction was used to eliminate leak current; initial 2 msec of tail currents were blanked. Tail currents recorded at some potentials (+20 to −60 mV) were fit with a single exponential function, since deactivation was slow enough that it did not to contribute significantly to net kinetics of tail current. At more negative potentials (−70 to −120 mV), currents were fit with a biexponential function to account for the fast phase of deactivation that overlapped recovery from inactivation. Fits to the data are superimposed over the current traces. FIG. 5B—Time constants for recovery from fast inactivation determined from fits of tail currents as described above. FIG. 5C—Fully-activated HERG I-V relationship. The maximal conductance of HERG current (118 μS) was determined from the slope of a linear fit to current amplitudes at potentials between −90 and −120 mV. FIG. 5D—Voltage-dependence of rapid inactivation of HERG current. The rectification factor, R, at each potential was calculated using current amplitudes plotted in panel (C):

$$R = [G \cdot n \cdot (V_t - E_{rev})] / I_{HERG}$$

where: G=maximal conductance of HERG (118 μS); n=activation variable at +40 mV (1.0); $V_t$=test potential; $E_{rev}$=reversal potential (−73 mV). The data were fit with a Boltzmann equation: $1/(1+\exp[(E_{rev}-V_{1/2})/k])$. The value of $V_{1/2}$ was −49 mV and the slope factor (k) was +28 mV.

Figure 6A:
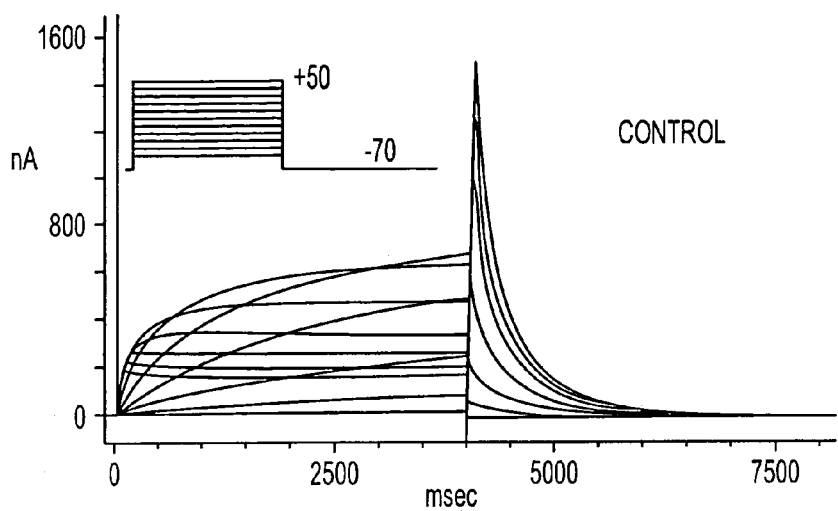
Figure 6B:
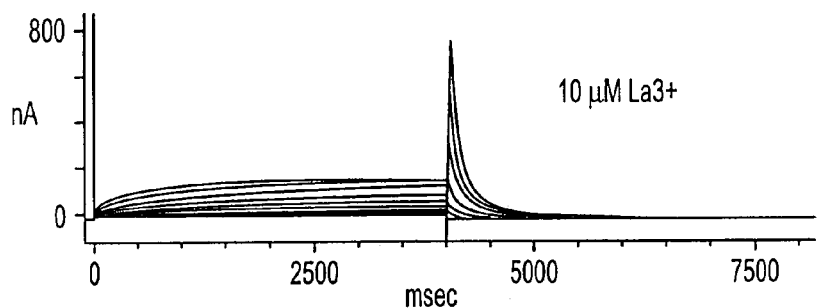
Figure 6C:
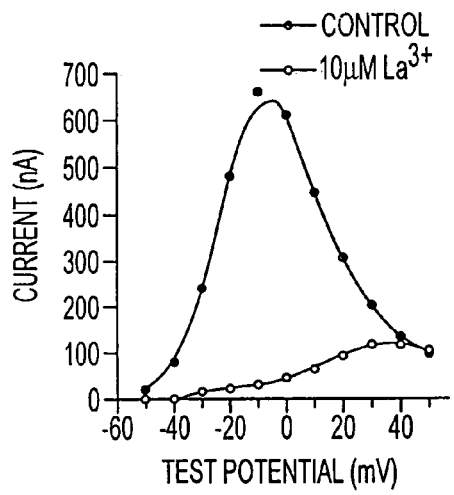
Figure 6D:
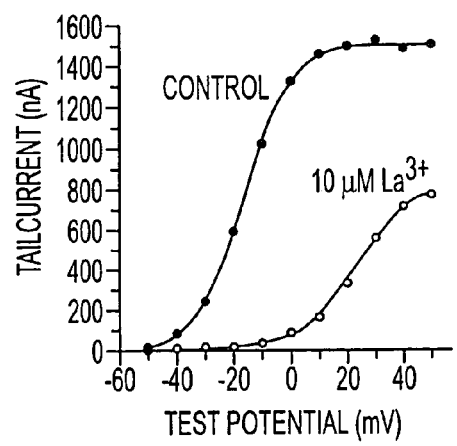

FIGS. 6A-6D. HERG current is blocked by La$^{3+}$. FIG. 6A—Control currents activated by 4 sec pulses to potentials ranging from −50 to +50 mV. Currents were not leak subtracted. FIG. 6B—Currents elicited with the same pulse protocol after exposure of oocyte to 10 μM LaCl$_3$. FIG. 6C—I-V relationship of HERG currents measured at the end of 4 sec test pulses. FIG. 6D—Isochronal activation curves were determined from plots of tail current amplitudes as a function of test potential. Data were fitted to a Boltzmann function to obtain the smooth isochronal activation curve. La$^{3+}$ shifted the half-point of activation from −16 mV to +23 mV.

Figure 7:
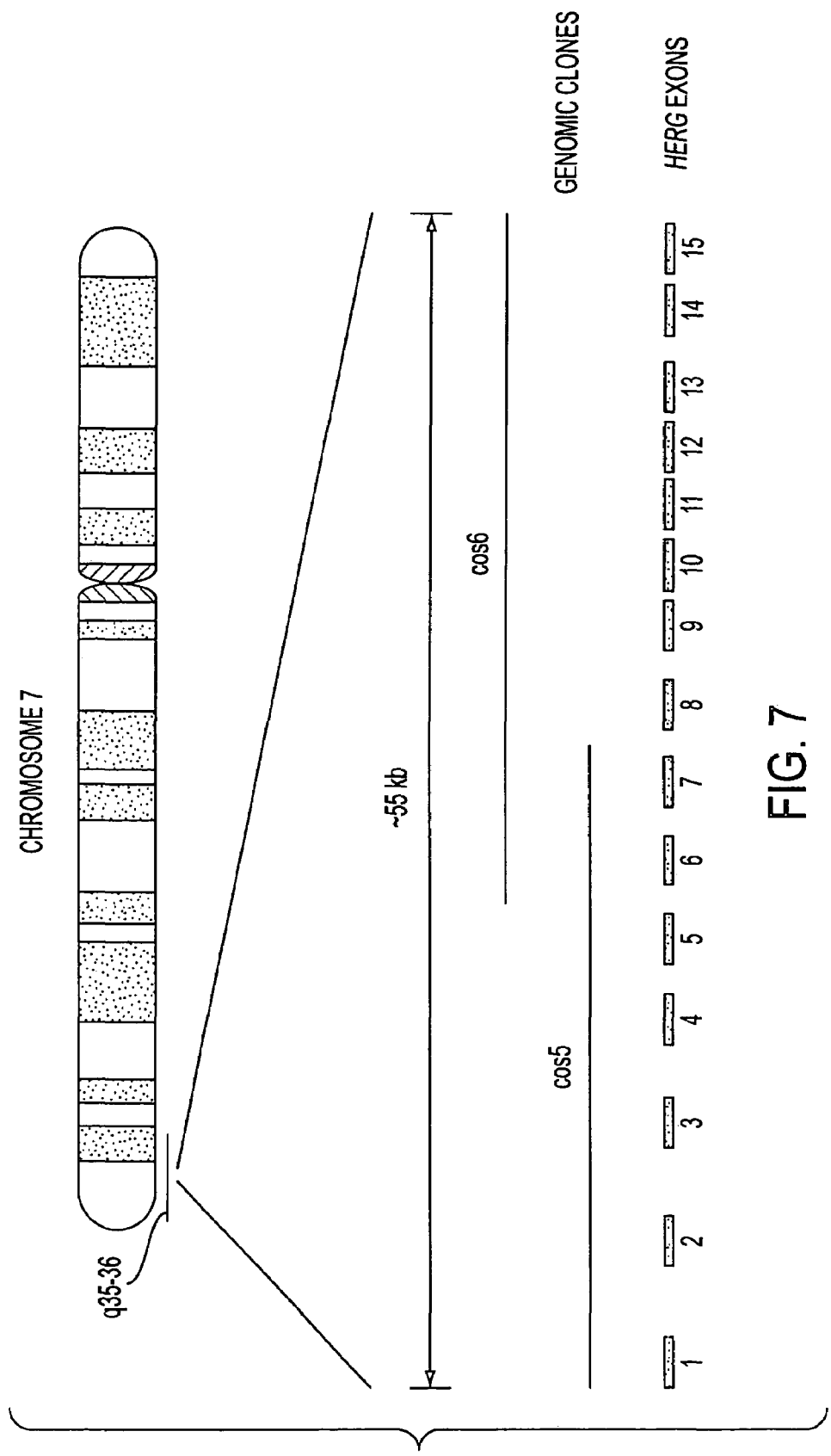

FIG. 7. Physical map and exon organization of HERG. The genomic region of HERG encompasses approximately 55 kilobases. The overlapping cosmid clones containing the entire HERG transcript sequence are shown. The location of HERG exons relative to genomic clones is indicated. Sizes of exons and distances are not drawn to scale.

FIGS. 8A-8B. Genomic organization of HERG coding and 5' and 3' untranslated sequences. Positions of introns are indicated with arrowheads. The six putative membrane-spanning segments (S1 to S6) and the putative pore (Pore) and cyclic nucleotide binding (cNBD) regions are underlined. The asterisk marks the stop codon. The nucleic acid and protein of FIGS. 8A-B are SEQ ID NO:3 and SEQ ID NO:4, respectively.

FIGS. 9A-9E. Pedigree structure and genotypic analyses of five new LQT families. Individuals showing the characteristic features of LQT, including prolongation of the QT interval and history of syncope, seizures or aborted sudden death, are indicated by filled circles (females) or squares (males). Unaffected individuals are indicated by empty circles or squares. Individuals with an equivocal phenotype, or for whom phenotypic data are unavailable, are stippled. Circles or squares with a slash denote deceased individuals. Haplotypes for polymorphic markers linked to LQT2 are shown under each individual. These markers include (centromere to telomere) D7S505, D7S636, HERG 5-11, HERG 3-8, D7S483 (Gyapay et al., 1994; Wang et al., 1995). Haplotypes cosegregating with the disease phenotype are indicated by a box. Recombination events are indicated with a horizontal black line. Informed consent was obtained from all individuals, or their guardians, in accordance with local institutional review board guidelines. Haplotype analyses indicate that the LQT phenotype in these kindreds is linked to markers on chromosome 7q35-36.

FIGS. 10A-10C. HERG intragenic deletions associated with LQT in two families. Pedigree structure of K2287 (FIG. 10A), results of PCR amplification using primer pair 1-9 (FIG. 10A), results of DNA sequencing of normal and mutant K2287 HERG genes (FIG. 10B), and the effect of the deletion on predicted structure of HERG protein (FIG. 10C) are shown. Note that an aberrant fragment of 143 bp is observed in affected members of this kindred, indicating the presence of a disease-associated intragenic deletion. DNA sequence of normal and aberrant PCR products defines a 27 bp deletion (ΔI500-F508). This mutation causes an in-frame deletion of 9 amino acids in the third membrane spanning domain (S3). Deleted sequences are indicated.

Figure 1A:
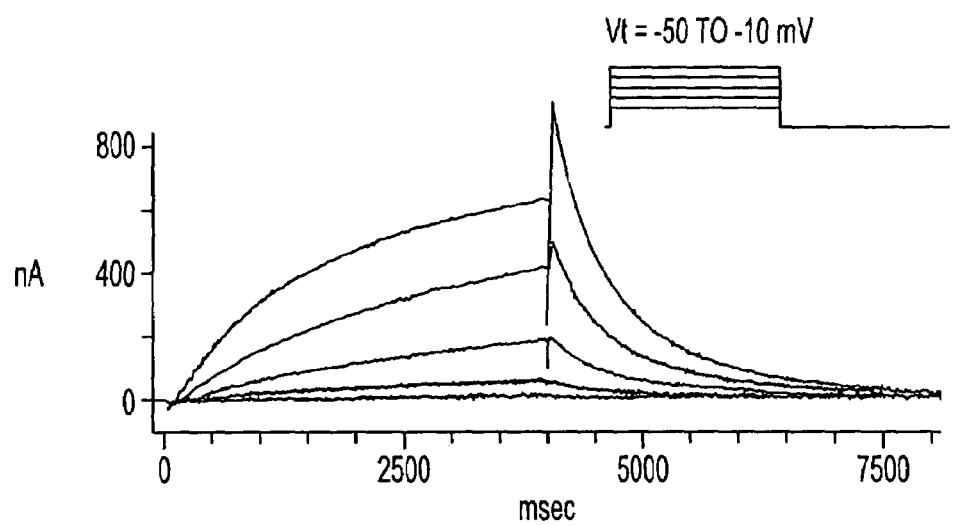
Figure 11A:
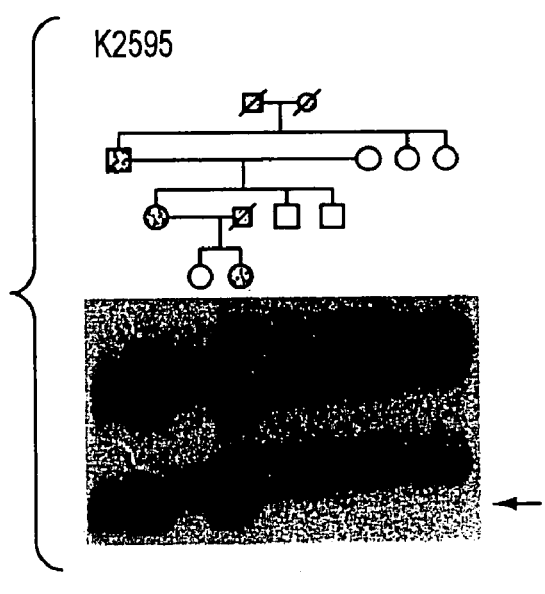
Figure 11B:
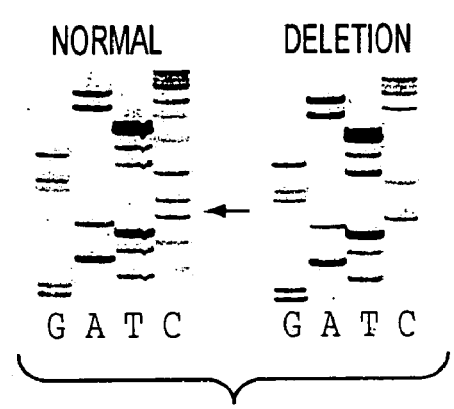

FIGS. 11A-11C. Pedigree structure of K2595 is shown (FIG. 11A). Deceased individuals are indicated by a slash. The result of SSCP analyses using primer pair 1-9 are shown beneath each individual (FIG. 1A). Note that an aberrant SSCP conformer cosegregates with the disease in this family. DNA sequence shows a single base-pair deletion (Δ1261) (FIG. 11B). This deletion results in a frameshift followed by a stop codon 12 amino acids downstream (FIG. 1C). The deleted nucleotide is indicated with an arrow.

Figure 12E:
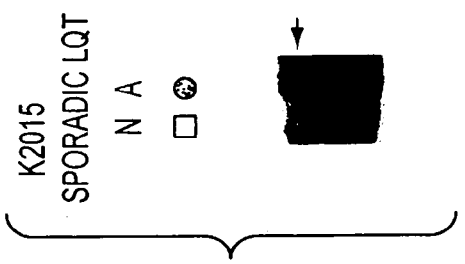
Figure 12C:
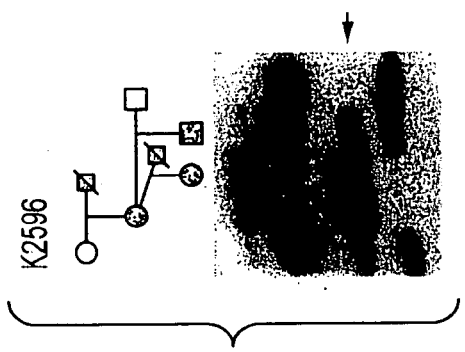
Figure 12A:
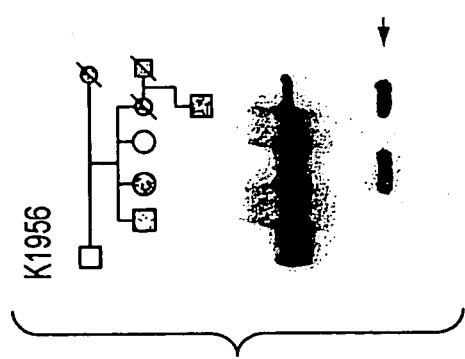
Figure 12F:
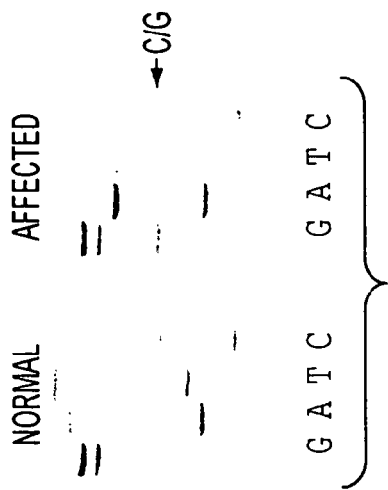
Figure 12D:
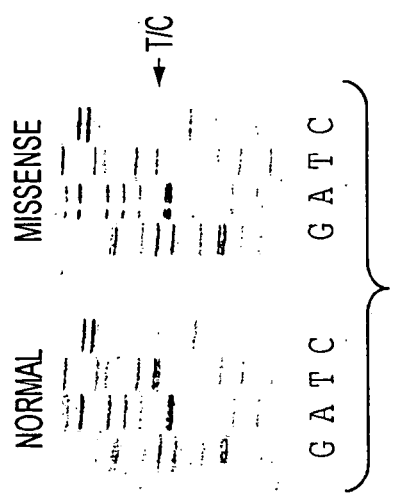
Figure 12B:
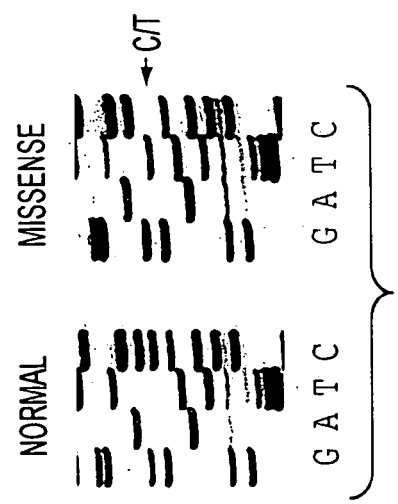
Figures 12G, 12H, 12I:
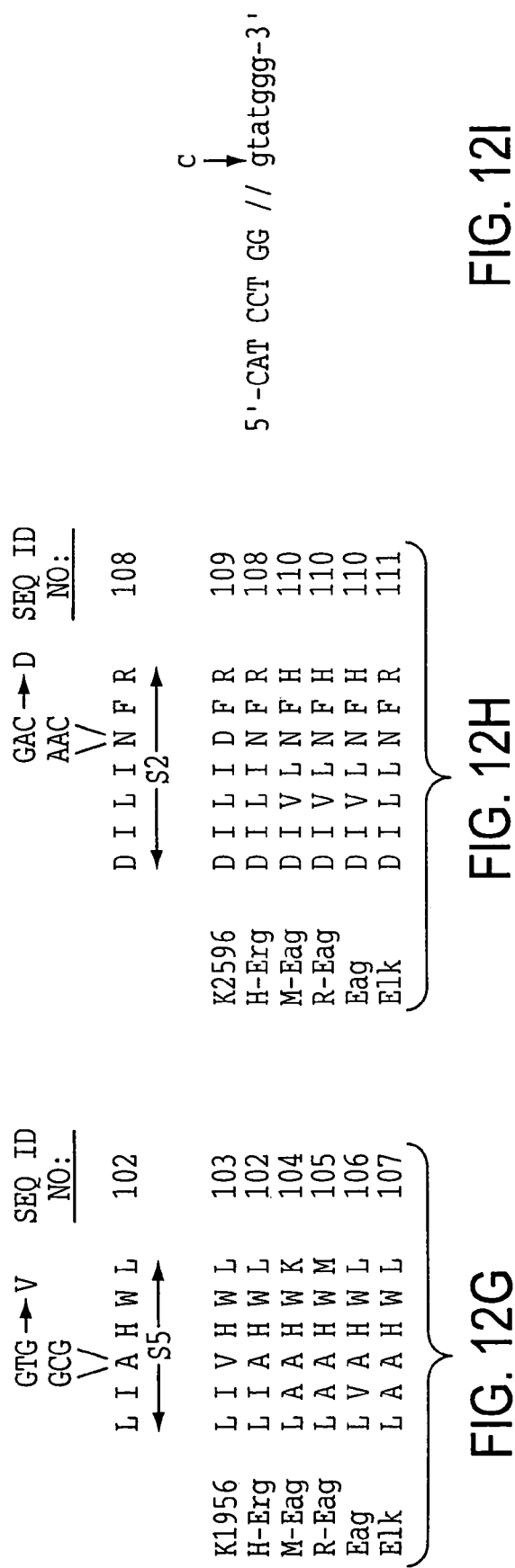

FIGS. 12A-12I. HERG point mutations identified in three LQT kindreds. Pedigree structure of K1956 (FIG. 12A), K2596 (FIG. 12C) and K2015 (FIG. 12E) are shown. Below each pedigree, the results of SSCP analyses with primer pair 5-11 (K1956) (FIG. 12B), primer pair 1-9 (K2596) (FIG. 12D) and primer pair 4-12 (K2015) (FIG. 12F) are shown. Aberran SSCP conformers cosegregate with the disease in each kindred. DNA sequence analyses of the normal and aberrant conformers reveals a C to T substitution at position 1682 in K1956. This mutation results in substitution of valine for a highly conserved alanine residue at codon 561 (A561V) (FIG. 12G). Analyses of K2596 reveals an A to G substitution at position 1408 (T to C substitution on the anti-sense strand is shown) (FIG. 12D). This mutation results in substitution of aspartic acid for a conserved asparagine in the second transmembrane domain (N470D) (FIG. 12H). Analyses of K2015 reveals a G to C substitution (C to G substitution on the anti-sense strand is shown) (FIG. 12F). This mutation occurs in the splice-donor sequence of intron III (see Curran et al., 1995) (intron 9 here) (FIG. 12I: SEQ ID NO:43). Coding sequences are upper case and intronic sequences are lower case. Note that the G to C substitution disrupts the splice-donor site. (HERG, M-eag, elk, Warmke and Ganetzky, 1994; R-eag; Ludwig et al., 1994).

FIGS. 13A-13E. HERG missense mutations associated with LQT. Results from SSCP analyses and the mutation effect on amino acid sequence are shown below each pedigree. Note that aberrant SSCP conformers (indicated by an arrow) cosegregate with the disease phenotype.

FIGS. 14A-14C. De novo mutation of HERG in a sporadic case of LQT. Pedigree structure of K2269 (FIG. 14A) and SSCP analyses (primer pair 14-16) (FIG. 14A) showing an aberrant conformer in a sporadic case of LQT. DNA sequence analyses identified a G to A substitution at position 1882 of the cDNA sequence (C to T substitution on the antisense-strand is shown) (FIG. 14B). Note that this mutation results in the substitution of a serine for a highly conserved glycine residue at codon 628 (G628S) (FIG. 14C). This amino acid sequence is known to be critical for potassium ion selectivity.

Figure 15:
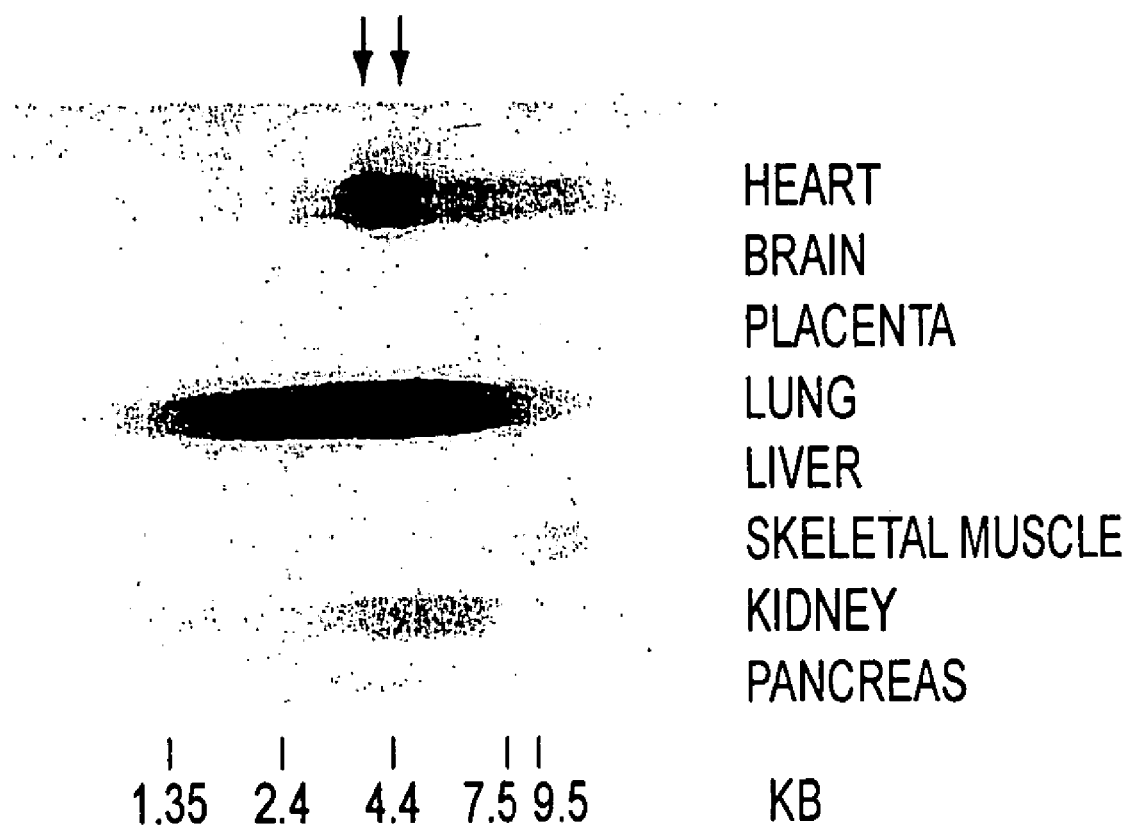

FIG. 15. Northern blot analysis of HERG mRNA showing strong expression in the heart. A Northern blot (Clonetech, poly A$^+$ RNA, 2 mg/lane) was probed using an HERG cDNA containing nucleotides 679 to 2239 of the coding sequence. Two cardiac mRNAs of ~4.1 and 4.4 kb are indicated. Background in mRNA extracted from lung was high, but no specific bands were identified.

SUMMARY OF SEQUENCE LISTING

SEQ ID NO:1 is the nucleic acid coding region only of HERG cDNA.

SEQ ID NO:2 is the HERG protein encoded by SEQ ID NO:1.

SEQ ID NO:3 is the nucleic acid of HERG cDNA and includes the complete coding region as well as some 5' and 3' untranslated regions.

SEQ ID NO:4 is the HERG protein encoded by SEQ ID NO:3.

SEQ ID NOs:5 and 6 are hypothetical nucleic acids used to demonstrate the calculation of percent homology.

SEQ ID NOs:7 and 8 are primers for amplifying the 3' UTR of HERG.

SEQ ID NOs:9-25 are primer pairs for SSCP analysis (Table 3).

SEQ ID NOs:26-55 are the intron/exon boundaries of HERG (Table 4).

SEQ ID NOs:56-95 are primers to amplify HERG exons (Table 5).

SEQ ID NOs:96-97 show the deletion of K2287 (FIG. 10C).

SEQ ID NOs:98-101 show the effect of the deletion in K2595 (FIG. 11C).

SEQ ID NOs:102-116 are a comparison of regions of HERG from humans, mouse, rat and Drosophila (FIGS. 12G-H and 14C).

DETAILED DESCRIPTION OF THE INVENTION

The present invention is directed to the genomic structure of HERG and to newly found mutations in HERG associated with LQT. The present invention is further directed to methods of screening humans for the presence of HERG gene variants which cause LQT. Since LQT can now be detected earlier (i.e., before symptoms appear) and more definitively, better treatment options will be available in those individuals identified as having hereditary LQT.

The present invention provides methods of screening the HERG gene to identify mutations. Such methods may further comprise the step of amplifying a portion of the HERG gene, and may further include a step of providing a set of polynucleotides which are primers for amplification of said portion of the HERG gene. The method is useful for identifying mutations for use in either diagnosis of LQT or prognosis of LQT.

Long QT syndrome is an inherited or an acquired disorder that causes sudden death from cardiac arrhythmias, specifically torsade de pointes and ventricular fibrillation. LQT was previously mapped to four loci: KVLQT1 on chromosome 11p15.5, HERG on 7q35-36, SCN5A on 3p21-24 and KCNE1 on chromosome 21q22.1-22.2.

Proof that the HERG gene is involved in causing hereditary LQT is obtained by finding sequences in DNA extracted from affected kindred members which create abnormal HERG gene products or abnormal levels of the gene products. Such LQT susceptibility alleles will co-segregate with the disease in large kindreds. They will also be present at a much higher frequency in non-kindred individuals with LQT than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type HERG gene is detected. In addition, the method can be performed by detecting the wild-type HERG gene and confirming the lack of a cause of LQT as a result of a mutation at this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the HERG gene product, or to a decrease in mRNA stability or translation efficiency.

The presence of hereditary LQT may be ascertained by testing any tissue of a human for mutations of the HERG gene. For example, a person who has inherited a germline HERG mutation would be prone to develop LQT. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the HERG gene. Alteration of a wild-type HERG allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the HERG locus) indicate a possible mutation. If restriction enzymes which produce very large restriction fragments are used, then pulsed field gel electrophoresis (PFGE) is employed.

Detection of point mutations may be accomplished by molecular cloning of the HERG alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. Coli mutS protein (Modrich, 1991); and 6) allele-specific PCR (Ruano and Kidd, 1989). For allele-specific PCR, primers are used which hybridize at their 3' ends to a particular HERG mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type HERG gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the HERG gene can also be detected using Southern hybridization, especially if the changes are gross rearrangements, such as deletions and insertions.

DNA sequences of the HERG gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified HERG sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCAI (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic HERG sequences from patients with those from a control population. Alternatively, one could sequence messenger RNA after amplification, e.g., by PCR, thereby eliminating the necessity of determining the exon structure of the candidate gene.

Mutations from patients falling outside the coding region of HERG can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of HERG mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type HERG protein. For example, monoclonal antibodies immunoreactive with HERG can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered HERG protein can be used to detect alteration of wild-type HERG genes. Functional assays, such as protein binding determinations, can be used. In addition, assays can be used which detect HERG biochemical function. Finding a mutant HERG gene product indicates alteration of a wild-type HERG gene.

Mutant HERG genes or gene products can also be detected in other human body samples, such as serum, stool, urine and sputum. The same techniques discussed above for detection of mutant genes or gene products in tissues can be applied to other body samples. By screening such body samples, a simple early diagnosis can be achieved for hereditary LQT.

The primer pairs of the present invention are useful for determination of the nucleotide sequence of a particular HERG allele using PCR. The pairs of single-stranded DNA primers can be annealed to sequences within or surrounding the HERG gene on chromosome 7 in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular HERG mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from HERG sequences or sequences adjacent to HERG, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the cDNA sequence of HERG (Warmke and Ganetzky, 1994), design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the HERG gene or mRNA using other techniques.

It has been discovered that individuals with the wild-type HERG gene do not have hereditary LQT. However, mutations which interfere with the function of the HERG gene product are involved in the pathogenesis of LQT. Thus, the presence of an altered (or a mutant) HERG gene which produces a protein having a loss of function, or altered function, directly causes LQT which increases the risk of cardiac arrhythmias. In order to detect a HERG gene mutation, a biological sample is prepared and analyzed for a difference between the sequence of the allele being analyzed and the sequence of the wild-type allele. Mutant HERG alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention., The present invention also provides methods of treating patients with $K^+$ to decrease the chances of developing LQT and/or torsade de pointes. The modulation of HERG by extracellular $K^+$ ($[K^+]_e$) may have physiologic importance. During rapid heart rates, or ischemia, $K^+$ accumulates within intracellular clefts (Gintant et al., 1992). This elevation in $[K^+]_e$ would increase the contribution of HERG to net repolarizing current. HERG may be even more important, therefore, in modulation of action potential duration at high heart rates, or during the initial phase of ischemia.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the HERG region are preferably complementary to, and hybridize specifically to sequences in the HERG region or in regions that flank a target region therein. HERG sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the HERG polypeptide and fragments thereof or to polynucleotide sequences from the HERG region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the HERG polypeptide or fragment. Monoclonal antibodies may be made by injecting mice with the protein polypeptides, fusion proteins or fragments thereof. Monoclonal antibodies will be screened by ELISA and tested for specific immunoreactivity with HERG polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"HERG Allele" refers to normal alleles of the HERG locus as well as alleles of HERG carrying variations that cause LQT.

"HERG Locus", "HERG Gene", "HERG Nucleic Acids" or "HERG Polynucleotide" each refer to polynucleotides, all of which are in the HERG region, that are likely to be expressed in normal tissue, certain alleles of which result in LQT. The HERG locus is intended to include coding sequences, intervening sequences and regulatory elements controlling transcription and/or translation. The HERG locus is intended to include all allelic variations of the DNA sequence.

These terms, when applied to a nucleic acid, refer to a nucleic acid which encodes a human HERG polypeptide, fragment, homolog or variant, including, e.g., protein fusions or deletions. The nucleic acids of the present invention will possess a sequence which is either derived from, or substantially similar to a natural HERG-encoding gene or one having substantial homology with a natural HERG-encoding gene or a portion thereof.

The HERG gene or nucleic acid includes normal alleles of the HERG gene, including silent alleles having no effect on the amino acid sequence of the HERG polypeptide as well as alleles leading to amino acid sequence variants of the HERG polypeptide that do not substantially affect its function. These terms also include alleles having one or more mutations which adversely affect the function of the HERG polypeptide. A mutation may be a change in the HERG nucleic acid sequence which produces a deleterious change in the amino acid sequence of the HERG polypeptide, resulting in partial or complete loss of HERG function, or may be a change in the nucleic acid sequence which results in the loss of effective HERG expression or the production of aberrant forms of the HERG polypeptide.

The HERG nucleic acid may be that shown in SEQ ID NO:1 (coding region of HERG cDNA) or SEQ ID NO:3 (cDNA including 5' UTR and 3' UTR) or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NOs:1 and 3 yet encode a polypeptide with the same amino acid sequence as shown in SEQ ID NOs:2 and 4. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NOs:2 and 4. Nucleic acid encoding a polypeptide which is an amino acid sequence variant, derivative or allele of the amino acid sequence shown in SEQ ID NOs:2 and 4 is also provided by the present invention.

The HERG gene also refers to (a) any DNA sequence that (i) hybridizes to the complement of the DNA sequences that encode the amino acid sequence set forth in SEQ ID NO:2 or SEQ ID NO:4 under highly stringent conditions (Ausubel et al., 1992) and (ii) encodes a gene product functionally equivalent to HERG, or (b) any DNA sequence that (i) hybridizes to the complement of the DNA sequences that encode the amino acid sequence set forth in SEQ ID NO:2 or SEQ ID NO:4 under less stringent conditions, such as moderately stringent conditions (Ausubel et al., 1992) and (ii) encodes a gene product functionally equivalent to HERG. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the HERG region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7-15 codons, and most preferably, at least about 35 codons. One or more introns may also be present. This number of nucleotides is usually about the minimal length required for a successful probe that would hybridize specifically with a HERG-encoding sequence. In this context, oligomers of as low as 8 nucleotides, more generally 8-17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the HERG locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8-40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1 or SEQ ID NO:3, its complement or functionally equivalent nucleic acid sequences. The present invention does not include nucleic acids which exist in the prior art. That is, the present invention includes all nucleic acids having at least 8 nucleotides derived from SEQ ID NO:1 or SEQ ID NO:3 with the proviso that it does not include nucleic acids existing in the prior art.

"HERG protein" or "HERG polypeptide" refers to a protein or polypeptide encoded by the HERG locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native HERG sequence, preferably in excess of about 90%, and more preferably at least about 95% homologous. Also included are proteins encoded by DNA which hybridize under high or low stringency conditions, to HERG-encoding nucleic acids and closely related polypeptides or proteins retrieved by antisera to the HERG protein(s).

The HERG polypeptide may be that shown in SEQ ID NO:2 or SEQ ID NO:4 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the HERG polypeptide. Such polypeptides may have an amino acid sequence which differs from that set forth in SEQ ID NO:2 or SEQ ID NO:4 by one or more of addition, substitution, deletion or insertion of one or more amino acids. Preferred such polypeptides have HERG function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the HERG polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of thehydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the HERG polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural HERG polypeptide.

"Probes". Polynucleotide polymorphisms associated with HERG alleles which predispose to LQT are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a HERG susceptibility allele.

Probes for HERG alleles may be derived from the sequences of the HERG region, its cDNA, functionally equivalent sequences, or the complements thereof. The probes may be of any suitable length, which span all or a portion of the HERG region, and which allow specific hybridization to the region. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding HERG are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding HERG is present in a cell or tissue. The present invention includes all novel probes having at least 8 nucleotides derived from SEQ ID NO:1 or SEQ ID NO:3, its complement or functionally equivalent nucleic acid sequences. The present invention does not include probes which exist in the prior art. That is, the present invention includes all probes having at least 8 nucleotides derived from SEQ ID NO:1 or SEQ ID NO:3 with the proviso that they do not include probes existing in the prior art.

Similar considerations and nucleotide lengths are also applicable to primers which may be used for the amplification of all or part of the HERG gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding HERG is present in a cell or tissue. The present invention includes all novel primers having at least 8 nucleotides derived from the HERG locus for amplifying the HERG gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for HERG polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of HERG polypeptides. Immunological activities include both immunogenic function in a target immune system, as well as sharing of immunological epitopes for binding, serving as either a competitor or substitute antigen for an epitope of the HERG protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8-10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for HERG polypeptides or fragments thereof is described below.

The present invention also provides for fusion polypeptides, comprising HERG polypeptides and fragments. Homologous polypeptides may be fusions between two or more HERG polypeptide sequences or between the sequences of HERG and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the HERG polypeptides from other biological material, such as from cells transformed with recombinant nucleic acids encoding HERG, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A HERG protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/bl2.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs:5 and 6.

parameters may show an even higher homology for SEQ ID NOs:5 and 6, but for brevity not all the possible results are shown.

TABLE 1

| | Parameter Values | | | | |
|---|---|---|---|---|---|
| Match | Mismatch | Open Gap | Extension Gap | Regions of identity (%) | Homology |
| 1 | −2 | 5 | 1 | 4-29 of 5 and 5-31 of 6 (92%) | 39-59 of 5 and 71-91 of 6 (100%) | 71.3 |
| 1 | −2 | 2 | 1 | 4-29 of 5 and 5-31 of 6 (92%) | 33-63 of 5 and 64-96 of 6 (93%) | 83.7 |
| 1 | −1 | 5 | 1 | — | 30-59 of 5 and 61-91 of 6 (93%) | 44.3 |
| 1 | −1 | 2 | 1 | 4-29 of 5 and 5-31 of 6 (92%) | 30-63 of 5 and 61-96 of 6 (91%) | 87.1 |

(SEQ ID NO:5)
5'-ACCGTAGCTACGTACGTATATAGAAAGGGCGCGATCGTCGTCGCGTA

TGACGACTTAGCATGC-3'

(SEQ ID NO:6)
5'-ACCGGTAGCTACGTACGTTATTTAGAAAGGGGTGTGTGTGTGTGTGT

AAACCGGGGTTTTCGGGATCGTCCGTCGCGTATGACGACTTAGCCATGCA

CGGTATATCGTATTAGGACTAGCGATTGACTAG-3'

The program "BLAST 2 Sequences" shows differing alignments of these two nucleic acids depending upon the parameters which are selected. As examples, four sets of parameters were selected for comparing SEQ ID NOs:5 and 6 (gap x_dropoff was 50 for all cases), with the results shown in Table 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO:5 is the short sequence (63 bases), and two regions of identity are shown, the first encompassing bases 4-29 (26 bases) of SEQ ID NO:5 with 92% identity to SEQ ID NO:6 and the second encompassing bases 39-59 (21 bases) of SEQ ID NO:5 with 100% identity to SEQ ID NO:6. Bases 1-3, 30-38 and 60-63 (16 bases) are not shown as having any identity with SEQ ID NO:6. Percent homology is calculated as: (26/63)(92)+(21/63)(100)+(16/63)(0)=71.3% homology. The percents of homology calculated using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to be used, based solely on these four sets of parameters one would state that SEQ ID NOs:5 and 6 have 87.1% homology. Again it is to be noted that use of other Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, arid preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type HERG nucleic acid or wild-type HERG polypeptide. The modified polypeptide will be substantially homologous to the wild-type HERG polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type HERG polypeptide. Alternatively, the similarity of function (activity) of the modified polypeptide may be higher than the activity of the wild-type HERG polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type HERG gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with HERG genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing HERG nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of HERG polypeptides.

The probes and primers based on the HERG gene sequences disclosed herein are used to identify homologous HERG gene sequences and proteins in other species. These gene sequences and proteins are used in the diagnostic/prognostic, therapeutic and drug screening methods described herein for the species from which they have been isolated.

Methods of Use: Drug Screening

This invention is particularly useful for screening compounds by using the HERG polypeptide or binding fragment thereof in any of a variety of drug screening techniques.

The HERG polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a HERG polypeptide or fragment and the agent being tested, or examine the degree to which the formation of a complex between a HERG polypeptide or fragment and a known ligand is interfered with by the agent being tested.

Thus, the present invention provides methods of screening for drugs comprising contacting such an agent with a HERG polypeptide or fragment thereof and assaying (i) for the presence of a complex between the agent and the HERG polypeptide or fragment, or (ii) for the presence of a complex between the HERG polypeptide or fragment and a ligand, by methods well known in the art. In such competitive binding assays the HERG polypeptide or fragment is typically labeled. Free HERG polypeptide or fragment is separated from that present in a protein:protein complex, and the amount of free (i.e., uncomplexed) label is a measure of the binding of the agent being tested to HERG or its interference with HERG:ligand binding, respectively. One may also measure the amount of bound, rather than free, HERG. It is also possible to label the ligand rather than the HERG and to measure the amount of ligand binding to HERG in the presence and in the absence of the drug being tested.

Another technique for drug screening provides high throughput screening for compounds having suitable binding affinity to the HERG polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with HERG polypeptide and washed. Bound HERG polypeptide is then detected by methods well known in the art.

Purified HERG can be coated directly onto plates for use in the aforementioned drug screening techniques. However, non-neutralizing antibodies to the polypeptide can be used to capture antibodies to immobilize the HERG polypeptide on the solid phase.

This invention also contemplates the use of competitive drug screening assays in which neutralizing antibodies capable of specifically binding the HERG polypeptide compete with a test compound for binding to the HERG polypeptide or fragments thereof. In this manner, the antibodies can be used to detect the presence of any peptide which shares one or more antigenic determinants of the HERG polypeptide.

The above screening methods are not limited to assays employing only HERG but are also applicable to studying HERG-protein complexes. The effect of drugs on the activity of this complex is analyzed.

In accordance with these methods, the following assays are examples of assays which can be used for screening for drug candidates.

A mutant HERG (per se or as part of a fusion protein) is mixed with a wild-type protein (per se or as part of a fusion protein) to which wild-type HERG binds. This mixing is performed in both the presence of a drug and the absence of the drug, and the amount of binding of the mutant HERG with the wild-type protein is measured. If the amount of the binding is more in the presence of said drug than in the absence of said drug, the drug is a drug candidate for treating LQT resulting from a mutation in HERG.

A wild-type HERG (per se or as part of a fusion protein) is mixed with a wild-type protein (per se or as part of a fusion protein) to which wild-type HERG binds. This mixing is performed in both the presence of a drug and the absence of the drug, and the amount of binding of the wild-type HERG with the wild-type protein is measured. If the amount of the binding is more in the presence of said drug than in the absence of said drug, the drug is a drug candidate for treating LQT resulting from a mutation in HERG.

A mutant protein, which as a wild-type protein binds to HERG (per se or as part of a fusion protein) is mixed with a wild-type HERG (per se or as part of a fusion protein). This mixing is performed in both the presence of a drug and the absence of the drug, and the amount of binding of the mutant protein with the wild-type HERG is measured. If the amount of the binding is more in the presence of said drug than in the absence of said drug, the drug is a drug candidate for treating LQT resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an HERG specific binding partner, such as myosin, actinin or dystrophin, or to find mimetics of the HERG polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of LQT, use of such a substance in the manufacture of a composition for administration, e.g., for treatment of LQT, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of a HERG allele predisposing an individual to LQT, a biological sample such as blood is prepared and analyzed for the presence or absence of susceptibility alleles of HERG. In order to detect the presence of LQT or as a prognostic indicator, a biological sample is prepared and analyzed for the presence or absence of mutant alleles of HERG. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant HERG sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 7. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$-$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding HERG. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting HERG. Thus, in one example to detect the presence of HERG in a cell sample, more than one probe complementary to the gene is employed and in particular the number of different probes is alternatively two, three, or five different nucleic acid probe sequences. In another example, to detect the presence of mutations in the HERG gene sequence in a patient, more than one probe complementary to these genes is employed where the cocktail includes probes capable of binding to the allele-specific mutations identified in populations of patients with alterations in HERG. In this embodiment, any number of probes can be used, and will preferably include probes corresponding to the major gene mutations identified as predisposing an individual to LQT.

Methods of Use: Peptide Diagnosis and Diagnostic Kits

The presence of LQT can also be detected on the basis of the alteration of wild-type HERG polypeptide. Such alterations can be determined by sequence analysis in accordance with conventional techniques. More preferably, antibodies (polyclonal or monoclonal) are used to detect differences in, or the absence of HERG peptides. Techniques for raising and purifying antibodies are well known in the art and any such techniques may be chosen to achieve the preparations claimed in this invention. In a preferred embodiment of the invention, antibodies will immunoprecipitate HERG proteins from solution as well as react with these proteins on Western or immunoblots of polyacrylamide gels. In another preferred embodiment, antibodies will detect HERG proteins in paraffin or frozen tissue sections, using immunocytochemical techniques.

Preferred embodiments relating to methods for detecting HERG or their mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., HERG polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., HERG polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved HERG polypeptide activity or stability or which act as inhibitors, agonists, antagonists, etc. of HERG polypeptide activity. By virtue of the availability of cloned HERG sequences, sufficient amounts of the HERG polypeptide may be made available to perform such analytical studies as x-ray crystallography. In addition, the knowledge of the HERG protein sequences provided herein will guide those employing computer modeling techniques in place of, or in addition to x-ray crystallography.

Methods of Use: Gene Therapy

According to the present invention, a method is also provided of supplying wild-type HERG function to a cell which carries mutant HERG alleles. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the HERG gene or fragment, where applicable, may be employed in gene therapy methods in order to increase the amount of the expression products of such genes in cells. It may also be useful to increase the level of expression of a given LQT gene even in those heart cells in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of HERG polypeptide in the cells. A virus or plasmid vector (see further details below), containing a copy of the HERG gene linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and published PCT application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for preparing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes HERG, expression will produce HERG. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to heart tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a HERG susceptibility allele are treated with a gene delivery vehicle such that some or all of their heart precursor cells receive at least one additional copy of a functional normal HERG allele. In this step, the treated individuals have reduced risk of LQT to the extent that the effect of the susceptible allele has been countered by the presence of the normal allele.

Methods of Use: Peptide Therapy

Peptides which have HERG activity can be supplied to cells which carry a mutant or missing HERG allele. Protein can be produced by expression of the cDNA sequence in bacteria, for example, using known expression vectors. Alternatively, HERG polypeptide can be extracted from HERG-producing mammalian cells. In addition, the techniques of synthetic chemistry can be employed to synthesize HERG protein. Any of such techniques can provide the preparation of the present invention which comprises the HERG protein. The preparation is substantially free of other human proteins. This is most readily accomplished by synthesis in a microorganism or in vitro.

Active HERG molecules can be introduced into cells by microinjection or by use of liposomes, for example. Alternatively, some active molecules may be taken up by cells, actively or by diffusion. Supply of molecules with HERG activity should lead to partial reversal of LQT. Other molecules with HERG activity (for example, peptides, drugs or organic compounds) may also be used to effect such a reversal. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant HERG alleles, usually from a second animal species, as well as insertion of disrupted homologous genes. Alternatively, the endogenous HERG gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of LQT must be assessed. If the test substance prevents or suppresses the appearance of LQT, then the test substance is a candidate therapeutic agent for treatment of LQT. These animal models provide an extremely important testing vehicle for potential therapeutic products.

The identification of the association between the HERG gene mutations and LQT permits the early presymptomatic screening of individuals to identify those at risk for developing LQT. To identify such individuals, HERG alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal HERG gene or appropriate fragment (coding sequence or genomic sequence) are determined and then compared, or (2) the RNA transcripts of the HERG gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the HERG gene in an individual to be tested are cloned using conventional techniques. For example, a blood sample is obtained from the individual. The genomic DNA isolated from the cells in this sample is partially digested to an average fragment size of approximately 20 kb. Fragments in the range from 18-21 kb are isolated. The resulting fragments are ligated into an appropriate vector. The sequences of the clones are then determined and compared to the normal HERG gene.

Alternatively, polymerase chain reactions (PCRs) are performed with primer pairs for the 5' region or the exons of the HERG gene. PCRs can also be performed with primer pairs based on any sequence of the normal HERG gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common HERG gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal HERG gene and defective genes. This comparison is performed in steps using small (~500 bp) restriction fragments of the HERG gene as the probe. First, the HERG gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the HERG gene fragments are transcribed in vitro using the SP6 transcription system, well known in the art, in the presence of [$\alpha$-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the HERG fragment and the HERG allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the HERG gene and the consequent presence of LQT. These variants can take a number of forms. The most severe forms would be frame shift mutations or large deletions which would cause the gene to code for an abnormal protein or one which would significantly alter protein expression. Less severe disruptive mutations would include small in-frame deletions and non-conservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Pharmaceutical Compositions and Routes of Administration

The HERG polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,73 IA and WO 90/07936.

Methods of Preventing LQT and Torsade de Pointes

There is a variety of ways for LQT to develop. Mutations in specific genes, e.g. HERG, can cause LQT. Treatment with any of a variety of drugs can also cause LQT. These drugs include those being taken to treat cardiac arrhythmias and also other drugs including antihistamines and some antibiotics such as erythromycin. Regardless of whether the LQT is a result of mutations (hereditary or familial LQT) or drug induced (acquired LQT), it is due to an effect on an ion channel. The drugs interact with the $K^+$ channel $I_{Kr}$, the major subunit of which is encoded by HERG, thereby affecting $K^+$ flow in cardiac cells. Mutations in HERG also can affect $K^+$ flow through this channel. This can result in long QT syndrome and may lead to torsade de pointes. It has been found that elevation of extracellular $K^+$ causes an increase in outward HERG current. This is a paradoxical effect, since an increase of extracellular $K^+$ lowers the chemical driving force for outward $K^+$ flux and therefore, would be expected to decrease, rather than increase, outward current. This observation indicates that increasing extracellular $K^+$ will activate this $K^+$ channel. This activation can prevent LQT which could otherwise develop from at least partial inactivation of the channel as a result of a mutation in HERG or a result of drug treatment. A normal extracellular physiological $K^+$ concentration, as measured in serum, in humans is in the range of about 3.5-4.5 mM. Values in the range of 3-5 mM are frequently seen, less frequently values in the range 2-3 or 5-7 mM are seen. Occasionally values lower than 2 mM or higher than 7 mM are seen. It was found that the HERG current at an extracellular $K^+$ concentration of 5 mM is 40% greater than the current seen at 2 mM. Potentiation of this $K^+$ channel by increasing extracellular $K^+$ levels is beneficial. During rapid heart rates, or ischemia, $K^+$ accumulates within intracellular clefts. Raising extracellular $K^+$ should increase the outward current thereby reducing this intracellular accumulation. Monitoring extracellular $K^+$ levels in persons with hereditary forms of LQT or those on medications which can cause acquired LQT, will allow physicians to prescribe added $K^+$ to those patients with lower than normal or even at normal extracellular $K^+$ levels. By increasing these extracellular $K^+$ levels to at least normal levels of 3.5-4.5 mM, preferably above normal levels to 4.5-5.5 mM, most preferably to about 5 mM $K^+$, the development of LQT and/or torsade de pointes will be inhibited. This new knowledge of the causes of LQT will lead to a system of monitoring extracellular $K^+$ levels in patients at risk of developing LQT, either hereditary or acquired, and administering $K^+$ to those with low or even normal extracellular $K^+$ levels. Such treatment will lead to the prevention of LQT and/or torsade de pointes.

In theory, mutations in a cardiac sodium channel gene could cause LQT. Voltage-gated sodium channels mediate rapid depolarization in ventricular myocytes, and also conduct a small current during the plateau phase of the action potential (Attwell et al., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI-DIV), each of which contains six putative membrane spanning segments (S1-S6). SCN5A was mapped to chromosome 3p21, making it an excellent candidate gene for LQT3 (George et al., 1995) and, later, mutations in SCN5A were shown to be associated with LQT (Wang et al., 1995).

The mutations in HERG, a cardiac potassium channel gene, cause the chromosome 7-linked form of hereditary LQT (details provided in Examples). The mutations identified in HERG, and the biophysics of potassium channel alpha subunits, suggest that chromosome 7-linked hereditary LQT results from dominant-negative mutations and a resultant reduction in functional channels.

Presymptomatic diagnosis of LQT has depended on identification of QT prolongation on electrocardiograms. Unfortunately, electrocardiograms are rarely performed in young, healthy individuals. In addition, many LQT gene carriers have relatively normal QT intervals, and the first sign of disease can be a fatal cardiac arrhythmia (Vincent et al., 1992). Now that four LQT genes have been identified, genetic testing for this disorder can be contemplated. This will require continued mutational analyses and identification of additional LQT genes. With more detailed phenotypic analyses, phenotypic differences between the varied forms of LQT may be discovered. These differences may be useful for diagnosis and treatment.

The identification of the association between the HERG, KVLQT1, SCN5A and KCNE1 gene mutations and hereditary LQT permits the early presymptomatic screening of individuals to identify those at risk for developing LQT. To identify such individuals, the alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO) dot blot analysis and PCR-SSCP analysis. For example, either (1) the nucleotide sequence of both the cloned alleles and normal HERG gene or appropriate fragment (coding sequence or genomic sequence) are determined and then compared, or (2) the RNA transcripts of the HERG gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the HERG gene in an individual to be tested are cloned using conventional techniques. For example, a blood sample is obtained from the individual. The genomic DNA isolated from the cells in this sample is partially digested to an average fragment size of approximately 20 kb. Fragments in the range from 18-21 kb are isolated. The resulting fragments are ligated into an appropriate vector. The sequences of the clones are then determined and compared to the normal HERG gene.

Alternatively, polymerase chain reactions (PCRs) are performed with primer pairs for the 5' region or the exons of the HERG gene. PCRs can also be performed with primer pairs based on any sequence of the normal HERG gene. For example, primer pairs for one of the introns can be prepared and utilized. Finally, PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common HERG gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal HERG gene and defective genes. This comparison is performed in steps using small (~500 bp) restriction fragments of the HERG gene as the probe. First, the HERG gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the HERG gene fragments are transcribed in vitro using the SP6 transcription system, well known in the art, in the presence of [$\alpha$-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the HERG fragment and the HERG allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the HERG gene and the consequent presence of long QT syndrome. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for hereditary LQT at, or even before, birth. Presymptomatic diagnosis of LQT will enable prevention of these disorders. Existing medical therapies, including beta adrenergic blocking agents, may prevent and delay the onset of problems associated with the disease. Finally, this invention changes our understanding of the cause and treatment of common heart disease like cardiac arrhythmias which account for 11% of all natural deaths. Existing diagnosis has focused on measuring the QT interval from electrocardiograms. This method is not a fully accurate indicator of the presence of long QT syndrome. The present invention is a more accurate indicator of the presence of the disease.

The Association between HERG and Acquired LQT

Figure 1B:
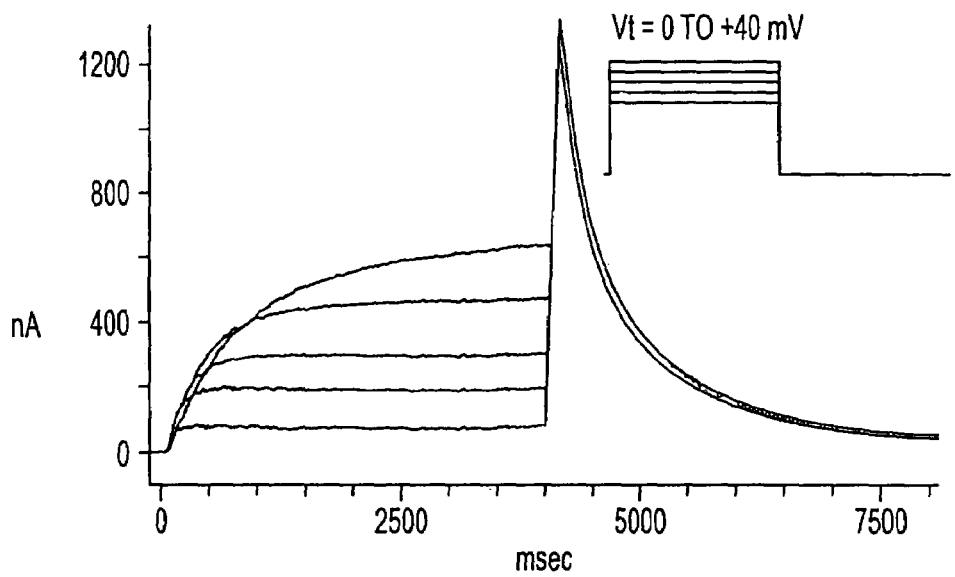

HERG Encodes a K$^+$ Channel with Inward Rectification Properties Similar to $I_{Kr}$. To determine the physiologic properties of HERG, a full-length cDNA was cloned and characterized. This was prepared for expression in *Xenopus* oocytes. The characteristics of the expressed channel were studied in oocytes 2-6 days after cRNA injection using standard two-microelectrode voltage clamp techniques. HERG current was activated in response to test potentials >−50 mV. The magnitude of HERG current increased progressively with test potentials up to −10 mV (FIG. 1A), then progressively decreased with test potentials ≧0 mV (FIG. 1B). Deactivation of current (tail current) was assessed after return of the membrane to the holding potential of −70 mV. The amplitude of the tail currents progressively increased after depolarization and saturated at +10 mV. The HERG current-voltage (I-V) relationship determined for 10 oocytes is shown in FIG. 1C. Peak outward current decreased with incremental depolarization, indicating that HERG is an inward rectifier. The voltage-dependence of channel activation was assessed by plotting the relative amplitude of tail currents as a function of test potential (FIG. 1D). HERG reached half-maximal activation at a potential of −15.1 mV. These data define HERG as a delayed rectifier K$^+$ channel with a voltage-dependence of activation and rectification properties nearly identical to $I_{Kr}$ (Sanguinetti and Jurkiewicz, 1990; Shibasaki, 1987; Yang et al., 1994). These properties are unlike any other cardiac current.

Figure 2A:
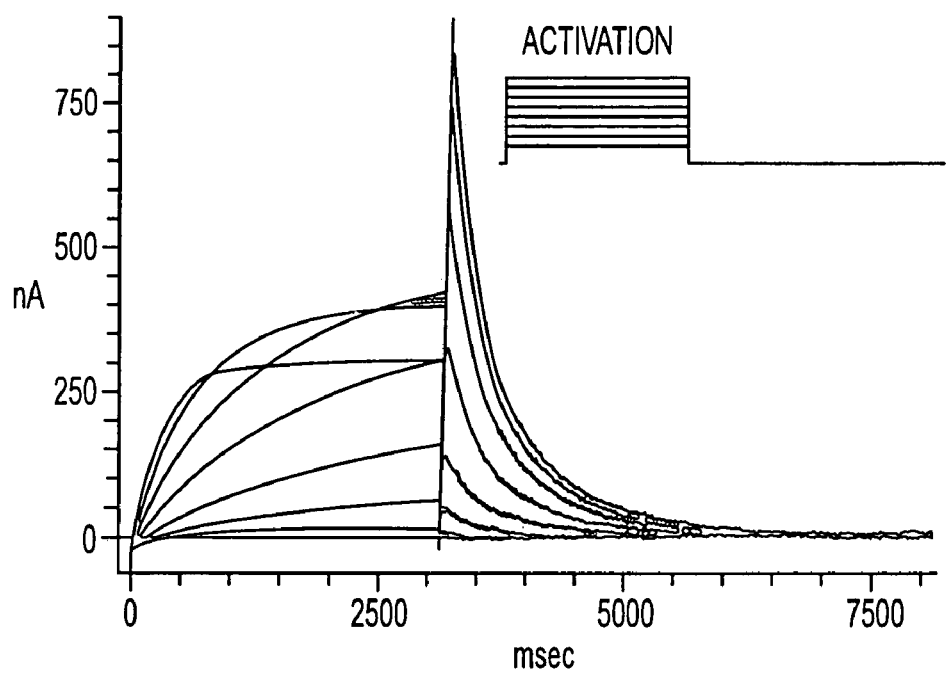
Figure 2B:
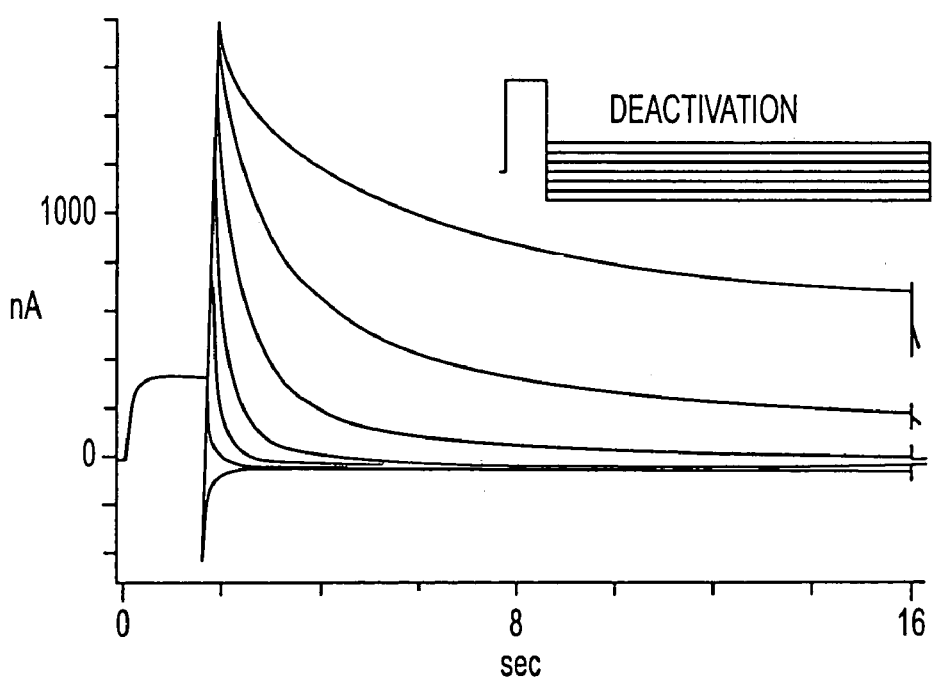

To further characterize HERG, the time-course of current activation and deactivation was determined. The time-course for the onset of current (activation) was best fit with a single exponential function (FIG. 2A). The rate of activation increased with incremental changes in test potentials from −40 to +50 mV. Deactivating currents were best fit with a biexponential function (FIG. 2B), similar to $I_{Kr}$ (Chinn, 1993; Yang et al., 1994). The time constants for HERG current activation, and the fast phase of deactivation, were a bell-shaped function of test potential (FIG. 2C). The relative amplitude of the fast component of deactivation varied from 0.77 at −30 mV to 0.2 at −120 mV (FIG. 2D). The kinetics of HERG current are slower than $I_{Kr}$ (Sanguinetti and Jurkiewicz, 1990; Shibasaki, 1987; Yang et al., 1994), but exhibit an identical voltage-dependence.

Figure 3A:
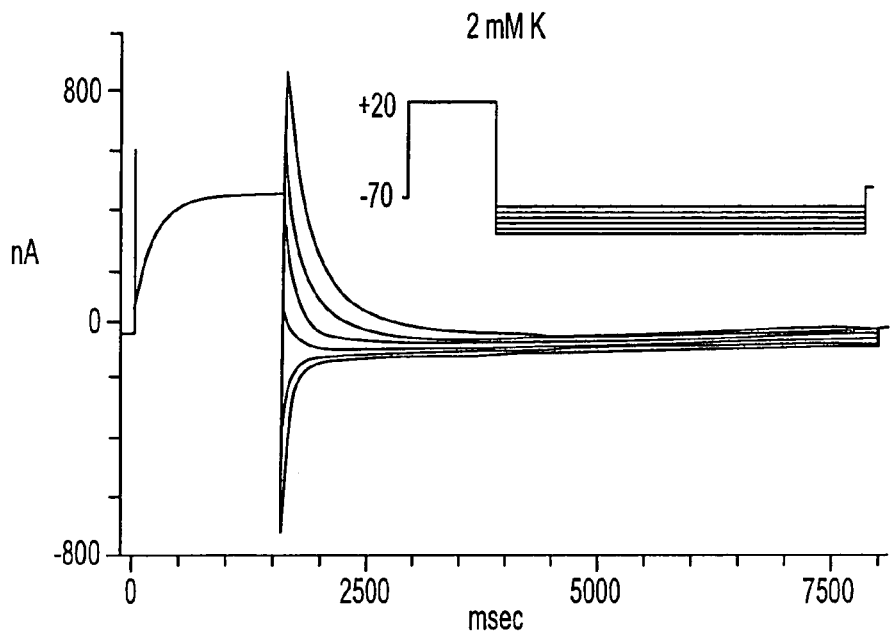
FIGS. 3A-3C. Reversal potential of HERG current varies with $[K^+]_e$ as expected for a $K^+$-selective channel.
Figure 3B:
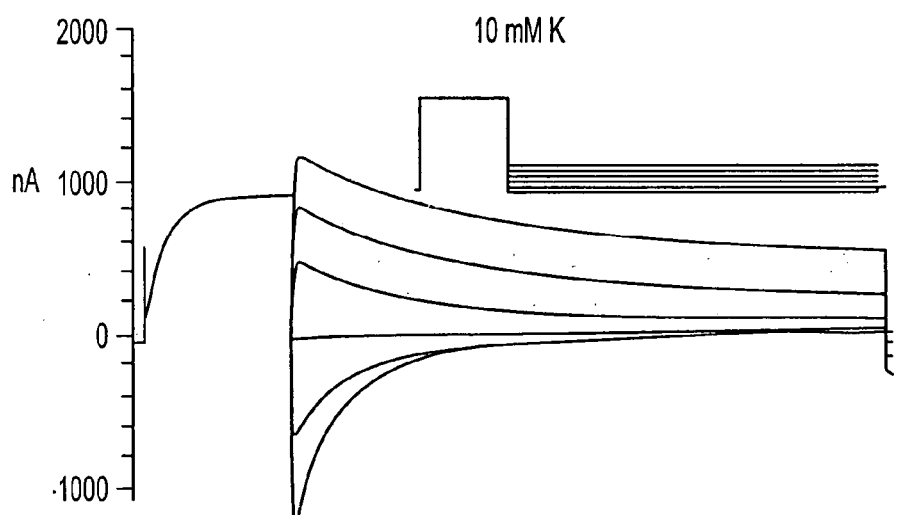
Figure 3C:
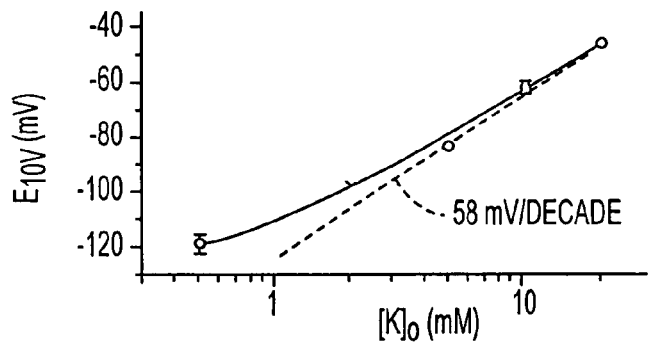

HERG Current is Activated by Extracellular $K^+$. The $K^+$-selectivity of HERG was determined by measuring the reversal potential of currents in oocytes bathed in ND96 solution containing different concentrations of KCl (0.5-20 mM). Tail currents were measured at a variable test potential after current activation by a pulse to +20 mV (FIGS. 3A and 3B). The voltage at which the tail current reversed from an inward to an outward current was defined as the reversal potential, $E_{rev}$. This varied with extracellular $K^+$ concentration ($[K^+]_e$), as predicted by the Nernst equation (58 mV change for a 10-fold increase in $[K^+]_e$) for $[K^+]_e$>5 mM. $E_{rev}$ varied over the entire range of $[K^+]_e$ in a manner well-described by the Goldman-Hodgkin-Katz current equation (FIG. 3C). These data indicate that HERG is selectively permeable to $K^+$ over $Na^+$ by a factor of 143.

Figure 4A:
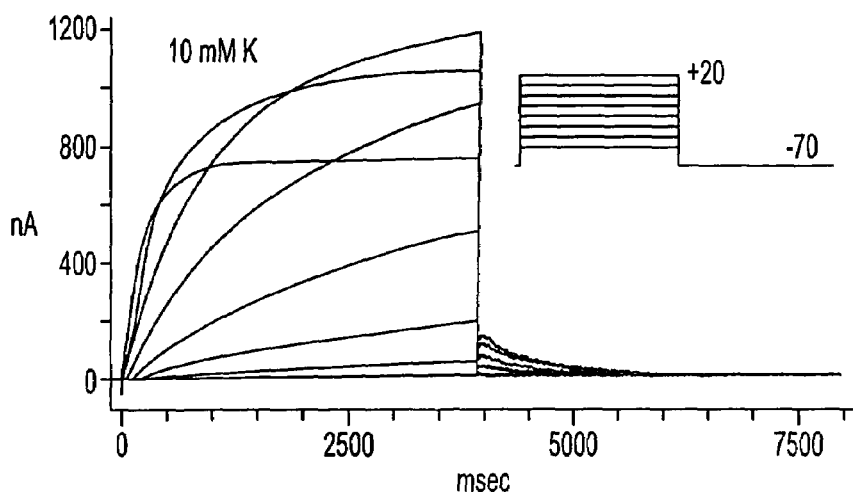
FIGS. 4A-4E. Activation of HERG current by extracellular $K^+$.
Figure 4B:
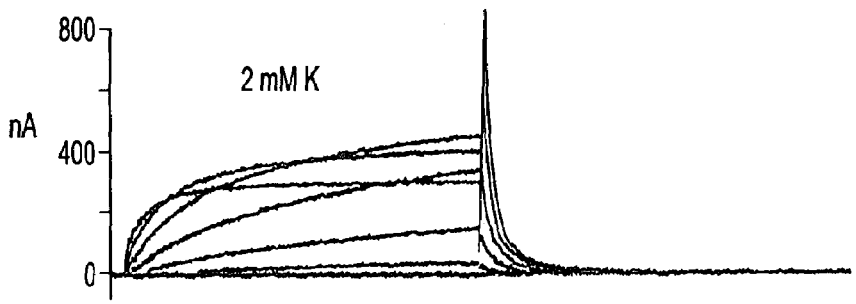
Figure 4C:
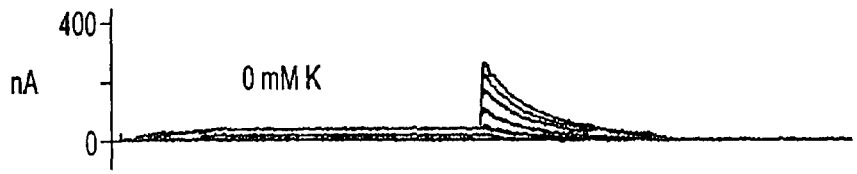
Figure 4D:
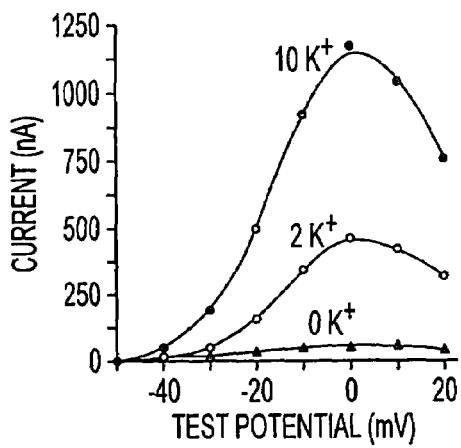
Figure 4E:
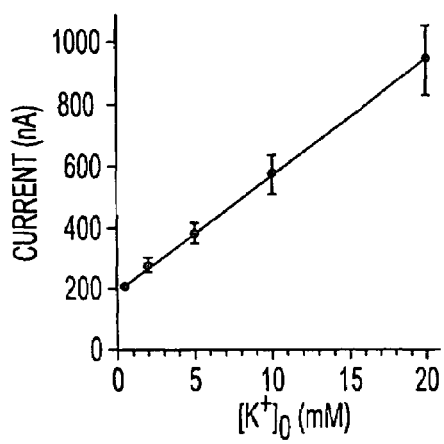

A hallmark feature of cardiac $I_{Kr}$ is its modulation by $[K+]_e$ (Sanguinetti and Jurkiewicz, 1992). The effect of $[K^+]_e$ on the magnitude of HERG current is shown in FIGS. 4A-C. HERG current increased in direct proportion to $[K^+]_e$, although the shape of the I-V relationship was not altered (FIG. 4D). The $[K^+]_e$-dependence of HERG current was determined by comparing the peak outward current at +20 mV in oocytes bathed in solutions containing 0.5 to 20 mM KCl. Over this range, HERG current amplitude varied as a linear function of $[K^+]_e$ (FIG. 4E). Unlike most other $K^+$ currents, the magnitude of outward HERG current is paradoxically reduced upon removal of extracellular $K^+$.

Rectification of HERG Current Results from Rapid Channel Inactivation. Inward rectification of $I_{Kr}$ is hypothesized to result from voltage-dependent inactivation that is more rapid than activation (Sanguinetti and Jurkiewicz, 1990; Shibasaki, 1987). The net result of these two competing processes is a reduced current magnitude relative to that predicted from the steady-state activation variable and the electrochemical driving force for outward $K^+$ flux. It is hypothesized that peak tail currents do not exhibit similar rectification after strong depolarizations (see FIG. 1) because the channels recover from fast inactivation much more rapidly than the time-course of deactivation. If this interpretation is correct, it should be possible to measure the time-course of recovery from fast inactivation during the onset of tail current. FIG. 5 shows the results of this experiment. Tail currents were recorded at several test potentials, each preceded by a prepulse to +40 mV (FIG. 5A). The voltage-dependence of the time constant for recovery from fast inactivation is plotted in FIG. 5B. Recovery was slowest at −30 mV (t=18.6 msec) and became faster with incremental increases or decreases in test potential. The bell-shaped relationship between the time constant for recovery from inactivation and membrane potential peaked at the same voltage (−30 mV) as the relationship describing the voltage-dependence of HERG current activation and deactivation (FIG. 2C). Although the onset of fast inactivation could not be quantified (because it occurred much faster than activation), it is likely that the descending limb of the curve in FIG. 4B (from −20 to +20 mV) also describes the voltage-dependence of rapid inactivation. These data indicate that inward rectification of HERG current results from an inactivation process that is much more rapid than the time course of activation.

The voltage-dependence of channel rectification was determined by comparison of the fully-activated I-V relationship for HERG current (FIG. 5C) with the I-V relationship expected for an ohmic conductor. The dotted line in FIG. 5C was extrapolated from a linear fit of current amplitudes measured at −90 to −120 mV, and described the I-V relationship that would occur in the absence of inward rectification (ohmic conduction). The, slope of this line defined the maximal conductance of HERG in this oocyte (118 µS), and was used to calculate the voltage-dependence of channel rectification (FIG. 5D). Rectification was half-maximal at −49 mV, and the relationship had a slope factor of 28 mV. The half-point was very similar to $I_{Kr}$ in rabbit nodal cells and the slope factor was nearly identical to $I_{Kr}$ in guinea pig myocytes (Table 2).

TABLE 2

Comparison of the properties of HERG and $I_{Kr}$

| | | Current-voltage relation | | Activation | | |
|---|---|---|---|---|---|---|
| Current | Inward Rectification | peak (mV) | full rectification (mV) | threshold (mV) | half-point (mV) | slope factor (mV) |
| HERG[1] | + | 0 | +60 | −50 | −15 | 7.9 |
| $I_{Kr}$ (guinea pig heart)[2] | + | 0 | +60 | −50 | −22 | 7.5 |
| $I_{Kr}$ (rabbit heart)[3] | + | n.d. | n.d. | −50 | −25 | 7.4 |
| $I_{Kr}$ (mouse AT-1 cells)[4] | + | 10 | +55 | −50 | +1 | n.d. |

| | Inactivation | | | Blockers | | |
|---|---|---|---|---|---|---|
| | half-point (mV) | slope factor (mV) | Modulation of current by $[K^+]_e$ | $La^{3+}$, $Co^{2+}$ | methanesulfonanilides | | |
| | | | | | E-4031 | MK-499 | dofetilide |
| HERG | −49 | +28 | + | + | (1 µM - no effect) | | n.d. |

TABLE 2-continued

Comparison of the properties of HERG and $I_{Kr}$

| $I_{Kr}$ (guinea pig) | −9 | +22 | + | + | $IC_{50}$ = 397 nM | 44 nM | 32 nM |
|---|---|---|---|---|---|---|---|
| $I_{Kr}$ (rabbit) | −68 | n.d. | n.d. | n.d. | $IC_{50}$ = <1 μM | n.d. | 4 nM |
| $I_{Kr}$ (AT-1 cells) | n.d. | n.d. | n.d. | + | $IC_{50}$ = n.d. | n.d. | 12 nM | n.d. = not determined
References:
[1] This study;
[2] (Jurkiewicz and Sanguinetti, 1993; Lynch et al., 1994; Sanguinetti and Jurkiewicz, 1990; Sanguinetti and Jurkiewicz, 1991);
[3] (Carmeliet, 1992; Shibasaki, 1987);
[4] (Yang et al., 1994)

Steady-state HERG current at any given test potential ($V_t$) can be defined:

$$I_{HERG} = G \cdot n \cdot R \cdot (V_t - E_{rev})$$

where: G=maximal conductance of HERG current; n=activation variable; R=rectification variable; $E_{rev}$=reversal potential.

HERG Current Is Blocked by Lanthanum and Cobalt, but Not Affected by Methanesulfonanilides or Cyclic Nucleotides. $I_{Kr}$ of cardiac myocytes is blocked by 10-100 μM lanthanum ($La^{3+}$), 2 mM cobalt ($Co^{2+}$) (Balser et al., 1990; Sanguinetti and Jurkiewicz, 1990), and nM concentrations of several methanesulfonanilide antiarrhythmic drugs, such as E-4031 (Sanguinetti and Jurkiewicz, 1990) and MK-499 (Lynch et al., 1994). It was determined whether HERG current is also blocked by these cations and drugs. At a test potential of 0 mV, 10 μM $La^{3+}$ reduced HERG current by 92±3% (n=4, FIG. 6). At least part of the blocking effect of $La^{3+}$ resulted from screening of negative membrane surface charge (Sanguinetti and Jurkiewicz, 1990), as indicated by the 40 mV positive shift in both the peak of the I-V relationship (FIG. 6C) and the isochronal activation curve (FIG. 6D). HERG was also partially blocked (52%) by 2 mM $Co^{2+}$ (n=2). However, neither E-4031 nor MK-499 at a concentration of 1 μM blocked HERG current, even after incubating the oocytes for up to 4 hours in these drugs.

The HERG channel contains a segment homologous to a cyclic nucleotide binding domain near its carboxyl terminus (Warmke and Ganetzky, 1994). To determine if HERG was sensitive to cyclic nucleotides, the effects of 8-Br-cAMP and 8-Br-cGMP on expressed HERG current were tested. These membrane permeant analogs of endogenous cyclic nucleotides have been shown to increase the magnitude of other channels expressed in *Xenopus* oocytes (Blumenthal and Kaczmarek, 1992; Bruggemann et al., 1993). Neither compound had a significant effect on current magnitude or voltage-dependence of channel activation at a concentration of 1 mM within 30 min of application (data not shown).

HERG Encodes Subunits of Cardiac $I_{Kr}$ Channels. The above results show that HERG encodes the major subunit of the cardiac $I_{Kr}$ channel. HERG expressed in oocytes induces a current that shares most of the distinguishing characteristics defining $I_{Kr}$ in cardiac myocytes (Table 2). These include: 1) inward rectification of the I-V relationship, with a peak near 0 mV; 2) voltage dependence of activation; 3) paradoxical modulation of current by [$K^+$]e; and 4) block by $La^{3+}$ and $Co^{2+}$. The kinetics of activation and deactivation of HERG current are much slower than $I_{Kr}$ in mouse AT-1 cells measured at room temperature (Yang, et al., 1994). This difference may indicate that some other endogenous factor, or an additional channel subunit modulates the gating of $I_{Kr}$ channels in cardiac cells. In addition, HERG is not activated by 8-Br-cAMP, consistent with the finding that isoproterenol does not increase $I_{Kr}$ in cardiac myocytes (Sanguinetti et al., 1991). Co-assembly of HERG subunits in oocytes, presumedly as homotetramers (MacKinnon, 1991), therefore, can reconstitute the major biophysical properties of cardiac $I_{Kr}$. No other channel shares all these characteristics.

The only major difference between HERG current and $I_{Kr}$ is that HERG is not blocked by methanesulfonanilide drugs (E-4031, MK-499), potent and specific blockers of $I_{Kr}$ in isolated cardiac myocytes (Lynch et al., 1994; Sanguinetti and Jurkiewicz, 1990). This suggests that the $I_{Kr}$ channel and the methanesulfonanilide receptor are separate, but interacting, proteins. A similar phenomenon has been described for the $K_{ATP}$ channel, recently isolated from mammalian heart (Ashford et al., 1994). When this channel (rc$K_{ATP}$-1) is expressed in HEK293 cells, it has all the biophysical characteristics of the native channel (Ashford et al., 1994), including modulation by intracellular nucleotides. However, the channel is not blocked by glibenclamide, a drug that inhibits $K_{ATP}$ channels in cardiac myocytes (Ashford et al., 1994). It may be possible to isolate the methanesulfonanilide receptor biochemically using known high affinity probes such as dofetilide or MK-499. Co-expression of HERG channels with the methanesulfonanilide receptor will enable detailed studies of the interaction between these two molecules.

The Mechanism of HERG Rectification Is Rapid Channel Inactivation. A unique feature of $I_{Kr}$ is inward rectification of the I-V relationship. The cardiac inward rectifier, $I_{K1}$, also exhibits intense inward rectification, but this occurs over a much more negative voltage range. Under normal physiologic conditions, peak outward $I_{K1}$ occurs at −60 mV, whereas $I_{Kr}$ peaks at 0 mV. The mechanism of $I_{K1}$ rectification results from both a voltage-dependent gating mechanism and block of outward current by intracellular $Mg^{2+}$ (Vandenberg, 1987) and spermine (Fakler et al., 1995). In contrast, it was postulated that inward rectification of $I_{Kr}$ results from voltage-dependent inactivation that occurs much faster than activation (Shibasaki, 1987). The kinetics of fast inactivation are difficult to resolve in macroscopic current recordings of myocytes and, therefore, were calculated based on kinetics of single channel activity (Shibasaki, 1987). In this study, it was possible to resolve the time-course for recovery from inactivation of macroscopic HERG current because of the large signal-to-noise ratio and the relatively slow channel gating kinetics at room temperature. The rapid onset of, and recovery from, fast inactivation explains the marked inward rectification of the I-V relationship for HERG. For example, at a test potential of +20 mV, HERG activates with a time constant of 230 msec, but simultaneously inactivates with a time constant of 12 msec. Thus, inactivation is complete before activation of current has reached a significant level, resulting in a much reduced current amplitude. Recovery from inactivation occurs so fast, relative to deactivation, that tail current amplitudes are not significantly affected after repolarization. Our findings support Shibasaki's hypothesis that the mechanism of rectification for $I_{Kr}$ (and HERG) is rapid, voltage-dependent inactivation.

Rectification of HERG current was half-maximal ($V_{1/2}$) at −49 mV, and had a slope factor of 28 mV. The slope factor of HERG rectification was similar to $I_{Kr}$ measured in guinea pig myocytes (22 mV). The $V_{1/2}$ of HERG rectification was more negative than that estimated in guinea pig (Table 2). However, the voltage-dependence of $I_{Kr}$ rectification in guinea pig myocytes was difficult to measure because of overlap with a much larger $I_{K1}$ at negative test potentials. The absence of overlapping current in rabbit nodal cells, and in oocytes expressing HERG, allowed more accurate measure of the voltage-dependence of channel rectification, and these determinations were similar (Table 2). Single channel analyses of expressed HERG will enable a more detailed description of voltage-dependent gating and fast inactivation.

The $[K^{30}]_e$-Dependence of HERG Current May Modulate Duration of Cardiac Action Potentials. Elevation of $[K^+]_e$ caused an increase in outward HERG current. This is a paradoxical effect, since an increase of $[K^+]_e$ lowers the chemical driving force for outward $K^+$ flux and therefore, would be expected to decrease, rather than increase, outward current. The same phenomenon has been described for $I_{Kr}$ (Sanguinetti and Jurkiewicz, 1992; Scamps and Carmeliet, 1989), but not for any other cardiac channel, except $I_{K1}$. However, $I_{K1}$ is activated almost instantly with hyperpolarization, whereas HERG, like $I_{Kr}$, is relatively slowly activated by depolarization, and not activated by hyperpolarization.

The modulation of HERG (and $I_{Kr}$) by $[K^+]_e$ may have physiologic importance. During rapid heart rates, or ischemia, $K^+$ accumulates within intracellular clefts (Gintant et al., 1992). This elevation in $[K^+]_e$ would increase the contribution of HERG ($I_{Kr}$) to net repolarizing current. HERG ($I_{Kr}$) may be even more important, therefore, in modulation of action potential duration at high heart rates, or during the initial phase of ischemia.

The mechanism of HERG modulation by $[K^+]_e$ is not yet known, but may be similar to that described for another cloned $K^+$ channel, RCK4. The amplitude of RCK4 is also increased with elevation of $[K^+]_e$ (Pardo et al., 1992). Single channel analyses revealed that elevation of $[K^+]_e$ increased the number of channels available to open, but had no effect on single-channel conductance, mean open time, or gating charge (Pardo et al., 1992). Moreover, it was demonstrated that substitution of a single lysine, located near the pore of the channel, to a tyrosine residue (K533Y) eliminated this effect. A similar $[K^+]_e$-dependent increase in current was created by substitution of a single amino acid near the pore domain of Shaker B channels (Lopez-Barneo et al., 1993). Future experiments will determine if $K^+$ modulates single HERG channels by a similar mechanism.

Mutation of HERG and Drug-induced Block of $I_{Kr}$: A Mechanistic Link Between Inherited and Acquired LQT. Inherited LQT, and the more common (drug-induced) acquired form of the disorder, are associated with torsade depointes, a polymorphic ventricular tachyarrhythmia. It was recently shown that mutations in HERG cause chromosome 7-linked LQT, likely by a dominant-negative inhibition of HERG function (Curran et al., 1995). It should be noted that there are likely to be several different mechanisms that account for acquired and inherited LQT. For example, it was recently demonstrated that mutations in SCN5A, the cardiac sodium channel gene, cause chromosome 3-linked LQT (Wang et al., 1995). The discovery that HERG forms the $I_{Kr}$ channel provides a logical explanation for the observation that block of $I_{Kr}$ by certain drugs can provoke the same arrhythmia (torsade de pointes) as observed in familial LQT.

The present findings may have important clinical implications. It was found that changes in $[K^+]_e$ over a physiologic range significantly modulated the amplitude of HERG current. For example, elevation of $[K^+]_e$ from a level of 2 mM to a new level of 5 mM increased HERG current by 40%. Modest hypokalemia, a common clinical problem, would have a significant effect on HERG current. This may explain the association between hypokalemia and acquired LQT (Roden, 1988). Furthermore, hypokalemia per se has been associated with ventricular arrhythmias (Curry et al., 1976). Medications (e.g., sotalol, dofetilide) that decrease $I_{Kr}$ can be effective antiarrhythmic agents because they modestly lengthen cardiac action potentials, thereby inhibiting re-entrant arrhythmias. In the setting of hypokalemia, however, this effect would be exaggerated, leading to excessive action potential prolongation and induction of torsade de pointes. Modest elevation of serum $[K^+]$ in patients given these antiarrhythmic medications, or in patients given other drugs which can cause acquired LQT (e.g., antihistamines or antibiotics such as erythromycin) or in individuals with chromosome 7-linked LQT, should help prevent LQT and torsade de pointes.

In summary, it has been demonstrated that HERG encodes the major subunit forming $I_{Kr}$ channels. This discovery suggests that the molecular mechanism of chromosome 7-linked LQT, and certain acquired forms of the disorder, can result from dysfunction of the same ion channel.

The present invention is further detailed in the following Examples, which are offered by way of illustration and are not intended to limit the invention in any manner. Standard techniques well known in the art or the techniques specifically described below are utilized.

EXAMPLE 1

Methods for Phenotypic Evaluation

LQT kindreds were ascertained from medical clinics throughout North America. Phenotypic criteria were identical to those used in previous studies (Keating et al., 1991 a; Keating et al., 1991b; Keating, 1992). Individuals were evaluated for LQT based on the QT interval corrected for heart rate (QTc; Bazette, 1920), and the presence of syncope, seizures, and aborted sudden death. Informed consent was obtained from each individual, or their guardians, in accordance with local institutional review board guidelines. Phenotypic data were interpreted without knowledge of genotype. Symptomatic individuals with a corrected QT interval (QTc) of 0.45 seconds or greater and asymptomatic individuals with a QTc of 0.47 seconds or greater were classified as affected. Asymptomatic individuals with a QTc of 0.41 seconds or less were classified as unaffected. Asymptomatic individuals with QTc between 0.41 and 0.47 seconds and symptomatic individuals with QTc of 0.44 seconds or less were classified as uncertain.

EXAMPLE 2

Linkage Analysis

Pairwise linkage analysis was performed using MLINK in LINKAGE v5.1 (Lathrop et al., 1985). Assumed values of 0.90 for penetrance and 0.001 for LQT gene frequency were used. Gene frequency was assumed to be equal between males and females.

EXAMPLE 3

Isolation of HERG Genomic and cDNA Clones

HERG probes were generated using the products of PCR reactions with human genomic DNA and primer pairs 1-10, 6-13 and 15-17 (Table 3). These products were cloned, radiolabeled to high specific activity and used to screen a human genomic P1 library (Stemberg, 1990). Positive clones were purified, characterized and used for FISH and DNA sequence analyses. A HERG genomic clone containing domains S 1-S3 and intron I (Curran et al., 1995) (intron 6 here) was used to screen ~$10^6$ recombinants of a human hippocampal cDNA library (Stratagene, library #936205). A single, partially processed cDNA clone that contained nucleotides 32-2398 of HERG coding sequence was identified. A second screen of this library was performed using the coding portion of this cDNA. This screen produced a second clone containing HERG coding sequence from nucleotides 1216 through the 3' untranslated region (UTR), and included a poly-$A^+$ region. These two cDNAs were ligated using an XhoI site at position 2089. To recover the 5' region of HERG, ~$10^6$ clones of a human heart cDNA library (Stratagene, library #936207) were screened with the composite hippocampal cDNA. A single clone containing the 5'-UTR through nucleotide 2133 was isolated. This clone was combined with the hippocampal composite at a BglII site (nucleotide 1913) to produce a full-length HERG cDNA.

EXAMPLE 4

YAC-Based Mapping of HERG

A PCR assay specific for the 3' untranslated region of HERG (employing primers 5'GCTGGGCCGCTCCCCT-TGGA3' (SEQ ID NO:7) and 5'GCATCTTCATTAATTAT-TCA3' (SEQ ID NO:8) and yielding a 309-bp product) was used to screen a collection of YAC clones highly enriched for human chromosome 7 (Green et al., in press). Two positive YAC clones were identified (yWSS2193 and yWSS1759), both were contained within a larger contig that includes YACs positive for the genetic marker D7S505 (Green et al., 1994).

EXAMPLE 5

Fluorescent In Situ Hybridization

Metaphase chromosome spreads were prepared from normal cultured lymphocytes (46x,Y) by standard procedures of colcemid arrest, hypotonic treatment and acetic acid-methanol fixation. HERG P1 clone 16B4 was labeled by incorporation of biotin-14-dATP (BioNick System, Gibco-BRL), hybridized to metaphase spreads and detected with streptavidin-Cy3 according to standard methods (Lichter et al., 1988). To identify chromosome 7, a digoxigenin-labeled centromere-specific α-satellite probe (Oncor) was co-hybridized and detected with antidigoxigenin-FITC. Chromosomes were counterstained with DAPI and visualized directly on the photomicroscope.

EXAMPLE 6

SSCP Analysis

Genomic DNA samples were amplified by PCR and used in SSCP analyses as described (Orita et al., 1989; Ptacek et al., 1991). Primer pairs used for this study are shown in Table 3. Annealing temperature was 58° C. for all PCR reactions. Reactions (10 μL) were diluted with 40 μl of 0.1% SDS/1 mM EDTA and 30 μl of 95% formamide dye. Diluted products were denatured by heating at 94° C. or 100° C. for 5 or 10 minutes, and 3-5 μl of each sample were separated by electrophoresis on either 7.5% or 10% non-denaturing polyacrylamide gels (50 acrylamide: 1 Bis-acrylamide) at 4° C. Electrophoresis was carried out at 40-50 watts for 2 to 5 hours. Gels were transferred to 3MM filter paper, dried and exposed to X-ray film at −80° C. for 12-36 hours.

TABLE 3

HERG PCR Primers

| Name | Position | Sequence | SEQ ID NO: |
|---|---|---|---|
| 1 L | 1147-1166 | GACGTGCTGCCTGAGTACAA | 9 |
| 2 L | 1291-1312 | TTCCTGCTGAAGGAGACGGAAG | 10 |
| 3 L | 1417-1437 | ACCACCTACGTCAATGCCAAC | 11 |
| 4 L | INTRON I (intron 6) | TGCCCCATCAACGGAATGTGC | 12 |
| 5 L | 1618-1636 | GATCGCTACTCAGAGTACG | 13 |
| 6 L | 1802-1823 | GCCTGGGCGGCCCCTCCATCAA | 14 |
| 7 R | 1446-1426 | CACCTCCTCGTTGGCATTGAC | 15 |
| 8 R | 1527-1503 | GTCGAAGGGGATGGCGGCCACCATG | 16 |
| 9 R | INTRON I (intron 6) | TACACCACCTGCCTCCTTGCTGA | 17 |
| 10 R | 1643-1623 | GCCGCGCCGTACTCTGAGTAG | 18 |
| 11 R | 1758-1736 | CAGCCAGCCGATGCGTGAGTCCA | 19 |
| 12 R | INTRON II (intron 7) | GCCCGCCCCTGGGCACACTCA | 20 |
| 13 R | 2034-2016 | CAGCATCTGTGTGTGGTAG | 21 |
| 14 R | INTRON III (intron 9) | GGCATTTCCAGTCCAGTGC | 22 |
| 15 L | 2259-2278 | CCTGGCCATGAAGTTCAAGA | 23 |
| 16 L | 2214-2233 | GCACTGCAAACCCTTCCGAG | 24 |
| 17 R | 2550-2529 | GTCGGAGAACTCAGGGTACATG | 25 |

All primers are shown in 5' to 3' direction. Sense-strand oligonucleotides are indicated with an "L" and anti-sense oligonucleotides are indicated with an "R". cDNA sequence was obtained from the Genbank database, nucleotide numbering begins with the initiator methionine. The phrases "INTRON I", "INTRON II" and "INTRON III" are from Curran et al. (1995) and correspond to introns 6, 7 and 9, respectively.

The phrases "INTRON I", "INTRON II" and "INTRON III" are from Curran et al. (1995) and correspond to introns 6, 7 and 9, respectively.

EXAMPLE 7

Sequence Analysis of SSCP Conformers

Normal and aberrant SSCP conformers were cut directly from dried gels and eluted in 75-100 µl of distilled water at either 37° C. or 65° C. for 30 minutes. Ten µl of the eluted DNA was used as template for a second PCR reaction using the original primer pair. Products were fractionated in 2% low-melting temperature agarose gels (FMC), and DNA fragments were purified and sequenced directly by cycle sequencing (Wang and Keating, 1994). Alternatively, purified PCR products were cloned into pBluescript II SK+ (Stratagene) using the T-vector method as described (Marchuk et al., 1990). Plasmid DNA samples were purified and sequenced by the dideoxy chain termination method using SequiTherm Polymerase (Epicentre Technologies) or as previously described (Curran et al., 1993a).

EXAMPLE 8

Exon/Intron Boundary Determination

Screening of a human cosmid library yielded two cosmids spanning approximately 55 kb and encompassing all exons (FIG. 7). All genomic clones were sequenced using primers designed to the cDNA sequences. The HERG cosmids were sequenced by the dideoxy chain termination method on an Applied Biosystems model 373A DNA sequencer. The exact exon/intron boundaries were determined by comparison of cDNA, genomic sequences, and known splice site consensus sequences.

Exon/intron boundaries were determined by sequencing the cosmids with primers designed to the cDNA. Sequencing revealed the presence of 15 exons (FIG. 8) with sizes ranging from 100 bp (exon 11) to 553 bp (exon 15) (see Table 4). Intron donor and acceptor splice sites did not diverge from the invariant GT and AG. A single pair of primers was designed for most exons and two pairs with overlapping products were designed for exons 4, 6 and 7 (Table 5). Due to repetitive DNA sequences in flanking introns, nested PCR was used to amplify exons 1 and 11. This set of primers can be used to screen the entire coding sequence of HERG for mutations.

TABLE 4

Intron-Exon boundaries in HERG

| Exon Number | Intron (SEQ ID NO:) | Exon Size (bp) | Intron (SEQ ID NO:) |
|---|---|---|---|
| 1 | .5'-UTR...ATGCCGGTGC (26) | 76+ | GAGGGCCAGAgtgagtgggg (27) |
| 2 | gcccccctagGCCGTAAGTT (28) | 231 | CGGAAAGATGgtaggagcgg (29) |
| 3 | cactctgcagGGAGCTGCTT (30) | 165 | CTGGCCCCAGgtaagtgtac (31) |
| 4 | tctcccgcagGCCGCGCCAA (32) | 444 | GCCAGCACCGgtgagggcgc (33) |
| 5 | ctccacctagGGGCCATGCA (34) | 212 | GGTCACCCAGgtaggcgccc (35) |
| 6 | ccgggtgcagGTCCTGTCCC (36) | 429 | CTCTGAGGAGgtggggtcag (37) |
| 7 | tgtcccccagCTGATCGGGC (38) | 388 | CTCATTGGCTgtgagtgtgc (39) |
| 8 | acgccccagCCCTCATGTA (40) | 200 | CATGAACGCGgtgaggccac (41) |
| 9 | ctgccccagGTGCTGAAGG (42) | 253 | GCCATCCTGGgtatggggtg (43) |
| 10 | tggcctccagGGAAGAATGA (44) | 194 | CCTGCGAGATgtgagttggc (45) |
| 11 | ttggttccagACCAACATGA (46) | 100 | ACGGACAAGGgtgaggcggg (47) |
| 12 | tttcccacagACACGGAGCA (48) | 273 | CCCCTGTCAGgtatcccggg (49) |
| 13 | ctggctgcagGCGCCTTCTC (50) | 187 | AGCTCAACAGgtgagggagt (51) |
| 14 | cctgccccagGCTGGAGACC (52) | 178 | GCTTTCTCAGgtaagctcca (53) |
| 15 | tgtattgcagGTTTCCCAGT (54) | 150+ | GGGCAGTTAG...3' UTR (55) |

Intron donor and acceptor splice sites are shown in boldface type.

Intron sequence is shown in lower case letters and exon sequence is shown in upper case letters.

TABLE 5

Primers Used to Amplify HERG Exons

| Exon No.[a] | Forward Primer | (SEQ ID NO:) | Reverse Primer | (SEQ ID NO:) | Size (bp) | C[b] |
|---|---|---|---|---|---|---|
| 1 (o) | GGGCCACCCGAAGCCTAGT | (56) | CCGTCCCCTCGCCAAAGC | (57) | 298 | 2 |
| 1 (i) | CCGCCCATGGGCTCAGG | (58) | CATCCACACTCGGAAGAGCT | (59) | 162 | 2 |
| 2 | GGTCCCGTCACGCGCACTCT | (60) | TTGACCCCGCCCCTGGTCGT | (61) | 312 | 2 |
| 3 | GGGCTATGTCCTCCCACTCT | (62) | AGCCTGCCCTAAAGCAAGTACA | (63) | 213 | 2 |
| 4 | CTCCGGGGCTGCTCGGGAT | (64) | CACCAGCGCACGCCGCTCCT | (65) | 284 | 2 |
| 4 | GCCATGGACAACCACGTGGCA | (66) | CCCAGAATGCAGCAAGCCTG | (67) | 339 | 2 |
| 5 | GGCCTGACCACGCTGCCTCT | (68) | CCCTCTCCAAGCTCCTCCAA | (69) | 293 | 2 |
| 6 | CAGAGATGTCATCGCTCCTG | (70) | CAGGCGTAGCCACACTCGGTAG | (71) | 295 | 1 |
| 6 | TTCCTGCTGAAGGAGACGGAAG | (72) | TACACCACCTGCCTCCTTGCTGA | (73) | 296 | 1 |
| 7 | TGCCCCATCAACGGAATGTGC | (74) | GAAGTAGAGCGCCGTCACATAC | (75) | 333 | 1 |
| 7 | GCCTGGGCGGCCCCTCCATCAA | (76) | AGTTTCCTCCAACTTGGGTTC | (77) | 210 | 1 |
| 8 | GCAGAGGCTGACGGCCCCA | (78) | ACTTGTTTGCTGTGCCAAGAG | (79) | 321 | 2 |
| 9 | ATGGTGGAGTGGAGTGTGGGTT | (80) | AGAAGGCTCGCACCTCTTGAG | (81) | 390 | 2 |
| 10 | GAGAGGTGCCTGCTGCCTGG | (82) | ACAGCTGGAAGCAGGAGGATG | (83) | 307 | 2 |
| 11 (o) | GGGCCCTGATACTGATTTTG | (84) | GCCCTGTGAAGTCCAAAAAGC | (85) | 372 | 2 |
| 11 (i) | CCCTGATACTGATTTTGGTT | (86) | CACCCCGCCTTCCAGCTCC | (87) | 193 | 2 |
| 12 | TGAGGCCCATTCTCTGTTTCC | (88) | GTAGACGCACCACCGCTGCCA | (89) | 358 | 2 |
| 13 | CTCACCCAGCTCTGCTCTCTG | (90) | CACCAGGACCTGGACCAGACT | (91) | 273 | 2 |
| 14 | GTGGAGGCTGTCACTGGTGT | (92) | GAGGAAGCAGGGCTGGAGCTT | (93) | 258 | 2 |
| 15 | TGCCCATGCTCTGTGTGTATTG | (94) | CGGCCCAGCAGCGCCTTGATC | (95) | 232 | 2 |

[a]Nested PCR was used to amplify exons 1 and 11 due to repetitive DNA sequence (o-outer and i-inner pair of primers).
[b]Conditions of the PCR (details in Example 9)

EXAMPLE 9

Design of PCR Primers and PCR Reaction Conditions

Primers to amplify exons of the HERG gene were designed empirically or using OLIGO 4.0 (NBI). Amplification conditions were:

(1) 94° C. for 3 minutes followed by 30 cycles of 94° C. for 10 seconds, 58° C. for 20 seconds and 72° C. for 20 seconds and a 5 minute extension at 72° C.

(2) Same conditions as (1) but reactions had a final concentration of 10% glycerol and 4% formamide and were overlaid with mineral oil.

(3) 94° C. for 3 minutes followed by 5 cycles of 94° C. for 10 seconds, 64° C. for 20 seconds and 72° C. for 20 seconds and 30 cycles of 94° C. for 10 seconds, 62° C. for 20 second and 72° for 20 seconds and a 5 minute extension at 72° C.

In the nested PCR for exons 1 and 11 of HERG, a 2 µL aliquot from the initial reaction was used in the second reaction.

EXAMPLE 10

Northern Analysis

A multiple tissue Northern blot containing ~2 µg/lane of poly-A$^+$ mRNA was purchased from Clonetech (Human MTN blot 1). A high specific activity (>1.5×10$^9$ cpm/µg DNA), radiolabeled HERG cDNA fragment containing nucleotides 679-2239 of the coding sequence was prepared by random hexamer priming as described (Feinberg and Vogelstein, 1983). Probe was added to the hybridization solution at final concentration of 5×10$^6$ cpm/ml. Hybridization was carried out at 42° C. for 24 hours in 20 ml of Quickhyb solution (Stratagene). Final washes were carried out at 65° C. for 30 minutes in a solution of 0.1% SDS/0.1×SSC.

EXAMPLE 11

Linkage Analysis of HERG

LQT2 is linked to markers on chromosome 7q35-36. To determine the relative frequency of the three known LQT loci (LQT1, LQT2, LQT3), linkage analyses were, performed in families with this disorder. Five LQT families were identified and phenotypically characterized (FIG. 13). These families were unrelated and of varying descent, including Mexican (Spanish), German, English, and Danish. In each case, an autosomal dominant pattern of inheritance was suggested by inspection of the pedigree. Affected individuals were identified by the presence of QT prolongation on electrocardiograms and, in some cases, a history of syncope or aborted sudden death. No patients had signs of congenital neural hearing loss, a finding associated with the rare, autosomal recessive form of LQT, or other phenotypic abnormalities. Genotype analyses with polymorphic markers linked to the known LQT loci suggested that the disease phenotype in these families was linked to polymorphic markers on chromosome 7q35-36 (FIG. 14). The maximum combined two-point lod score for these five families was 5.13 at D7S636 ($\theta$=0.0; Table 6). When combined with a previous study (Jiang et al., 1994; Wang et al., 1995), the maximum combined two-point lod score for the fourteen chromosome 7-linked families was 26.14, also at D7S636 ($\theta$=0.0; Table 6). Haplotype analyses were consistent with previous studies, placing LQT2 between D7S505 and D7S483 (FIG. 14; Wang et al., 1995), localizing this gene to chromosome 7q35-36.

HERG maps to chromosome 7q35-36. HERG was previously mapped to chromosome 7 (Warmke and Ganetzky, 1994). To test the candidacy of this gene, the localization of HERG was refined using two physical mapping techniques. First, HERG was mapped on a set of yeast artificial chromosome (YAC) contigs constructed for chromosome 7 (Green et al., 1994). HERG was localized to the same YAC as D7S505, a polymorphic marker that was tightly linked to LQT2 (Table 6). Second, HERG was mapped to chromosome 7q35-36 using fluorescent in situ hybridization (FISH) with a P1 genomic clone containing HERG.

To determine if HERG was genetically linked to the LQT locus, SSCP analyses were used to identify polymorphisms within HERG, and linkage analyses were performed in the chromosome 7-linked families. Two aberrant SSCP conformers were identified in DNA samples from patients and controls using primer pairs 5-11, and 3-8. These conformers were cloned and sequenced. One abnormal conformer resulted from a C to T substitution at position 3 of codon 489 (cDNA nucleotide 1467, observed heterozygosity=0.37). The second abnormal conformer resulted from an A to G substitution at position 3 of codon 564 (cDNA nucleotide 1692, observed heterozygosity=0.44). Neither substitution affected the predicted amino acid sequence of HERG. HERG polymorphisms were used for genotypic analyses in chromosome 7-linked families (FIG. 9). No recombination events between HERG and LQT were identified in any of these families. The maximum combined lod score for the 14 families was 9.64 ($\theta$=0.0; Table 6). These data indicate that HERG is completely linked to LQT2.

TABLE 6

Maximum Pairwise Lod Scores and Recombination Fractions for Linkage of LQT2 with HERG, and Polymorphic Markers on Chromosome 7

| Locus | Families From Present Study | | Families Studied To Date | |
|---|---|---|---|---|
| | $Z_{max}$ | $\theta$ | $Z_{max}$ | $\theta$ |
| D7S505 | 4.40 | 0.0 | 22.91 | 0.009 |
| D7S636 | 5.13 | 0.0 | 26.14 | 0.00 |

TABLE 6-continued

Maximum Pairwise Lod Scores and Recombination Fractions for Linkage of LQT2 with HERG, and Polymorphic Markers on Chromosome 7

| Locus | Families From Present Study | | Families Studied To Date | |
|---|---|---|---|---|
| | $Z_{max}$ | $\theta$ | $Z_{max}$ | $\theta$ |
| HERG 3-8 | 0.11 | 0.0 | 6.34 | 0.00 |
| HERG 5-11 | 3.55 | 0.0 | 9.64 | 0.00 |
| D7S483 | 2.48 | 0.0 | 22.42 | 0.00 |

Markers are shown in chromosomal order (centromere to telomere, Gyapay et al., 1994). The first column (families from present study) indicates combined lod scores for the five families described in this study. The second column (families studied to date) indicates combined log scores from the five families studied here, and nine families from previous study (Jiang et al., 1994). $Z_{max}$ indicates maximum lod score. $\theta$ indicates estimated recombination fraction at $Z_{max}$.

HERG intragenic deletions associated with LQT in two families: To test the hypothesis that HERG is LQT2, SSCP analyses were used to screen for mutations in affected individuals. Since the genomic structure of HERG was unknown (this portion of the work being performed prior to determining the complete intron/exon structure for the gene), oligonucleotide primer pairs were designed from published (Warmke and Ganetzky, 1994) HERG cDNA sequences (Table 3). In most cases, single products of expected size were generated. For primer pairs 1-10, 6-13, and 15-17, however, products of greater than expected size were obtained, suggesting the presence of intronic sequences. To examine this possibility, these larger products were cloned and sequenced. DNA sequence analyses identified three introns at positions 1557/1558, 1945/1946, and 2398/2399 of the cDNA sequence SEQ ID NO:1 (FIG. 15). These boundaries were confirmed by direct DNA sequencing of HERG genomic clones containing HERG (data not shown). To facilitate SSCP analyses, additional primers were designed to intronic sequences.

As indicated previously, SSCP analyses using primer pair 3-8 identified an A to G polymorphism within HERG (cDNA nucleotide 1692). Analysis of kindred 2287 (K2287) using this SSCP polymorphism defined a pattern of genotypes consistent with a null allele (FIG. 13). Possible explanations for these findings included multiple misinheritances, a possibility not supported by previous genotypic analyses, DNA sample errors, base-pair substitutions, or a deletion. To test the hypothesis that the genotypic data were due to a small deletion, PCR analyses of K2287 were repeated using a new primer pair (3-9) flanking the previous set of primers. These experiments identified two products of 170 bp and 143 bp in affected members of K2287 (FIGS. 10A and 10B). By contrast, only a single product of 170 bp was observed in unaffected members of this kindred. Furthermore, only the 170 bp band was seen in DNA samples from more than 200 unaffected individuals. The 143 bp and 170 bp products were cloned from affected individual II-2. Direct sequence analyses of the aberrant PCR product revealed the presence of a 27 bp deletion beginning at position 1498 ($\Delta$I500-F508). This deletion disrupts the third membrane spanning domain (S3) of HERG.

To further test the hypothesis that HERG is LQT2, more SSCP analyses were performed in additional kindreds. SSCP using the primer pair 1-9 identified an aberrant conformer in affected individuals of K2595 (FIG. 11A). Analyses of more than 200 unaffected individuals failed to show this anomaly.

The normal and aberrant conformers were cloned and sequenced, revealing a single base deletion at position 1261 (Δ1261). This deletion results in a frameshift in sequences encoding the first membrane spanning domain (S1), leading to a new stop codon within 12 amino acids (FIG. 11B). The identification of intragenic deletions of HERG in two LQT families suggests that HERG mutations can cause LQT.

Seven HERG point mutations associated with LQT. To identify additional HERG mutations, further SSCP analyses were performed in linked kindreds and sporadic cases. Three aberrant SSCP conformers were identified in affected members of K1956, K2596 and K2015 (FIGS. 12A, 12C and 12E) and five other kindreds (K1663, K2548, K2554, K1697 and K1789) also showed anomalous bands (FIGS. 13A-E). In each case, the normal and aberrant conformers were cloned and sequenced. In K1956, a C to T substitution at position 1682 (with the start codon beginning with base 1 for all the data in this paragraph) was identified. This mutation results in substitution of valine for a highly conserved alanine at codon 561 (A561V), altering the fifth membrane spanning domain (S5) of the HERG protein (FIG. 12B). In K2596, an A to G substitution was identified at position 1408. This mutation results in substitution of aspartic acid for a conserved asparagine at codon 470 (N470D), located in the second membrane spanning domain (S2; FIG. 12D). In K2015, a G to C substitution was identified. This substitution disrupts the splice-donor sequence of intron III (intron 9), affecting the cyclic nucleotide binding domain (FIG. 12F). K1663 has a G1714T mutation resulting in G572C, K2548 has an A1762G mutation resulting in N588D, K2554 and K1697 both have a C1841T mutation yielding A614V, and K1789 has a T1889C mutation resulting in V630A. None of the aberrant conformers was identified in DNA samples from more than 200 unaffected individuals.

Following the above studies, further studies revealed several more mutations of HERG which were seen in persons diagnosed with LQT but not seen in 200 unaffected persons. These additional mutations are shown in Table 7.

TABLE 7

Mutations in HERG in Persons with LQT

| Nucleotide Change in SEQ ID NO: 1 | Coding Effect | Position | Exon | Kindred |
|---|---|---|---|---|
| C87A | Phe29Leu | N-terminal | 2 | 2228 |
| A98C | Asn33Thr | N-terminal | 2 | 2254 |
| A98C | Asn33Thr | N-terminal | 2 | 3378 |
| C132A | Cys44Stop | N-terminal | 2 | 2751 |
| G140T | Gly47Val | N-terminal | 2 | 2544 |
| G157C | Gly53Arg | N-terminal | 2 | 1789 |
| G167A | Arg56Gln | N-terminal | 2 | 2553 |
| T196G | Cys66Gly | N-terminal | 2 | 2755 |
| A209G | His70Arg | N-terminal | 2 | 2796 |
| A209G | His70Arg | N-terminal | 2 | 2971 |
| C215A | Pro72Gln | N-terminal | 2 | 2551 |
| C215A | Pro72Gln | N-terminal | 2 | 2822 |
| Δ221-251 | Arg73frameshift | N-terminal | 2 | 2840 |
| G232C | Ala78Pro | N-terminal | 2 | 2920 |
| duplicate 234-250 | Ala83frameshift | N-terminal | 2 | 1778 |
| C241T | Gln81Stop | N-terminal | 2 | 2711 |
| T257G | Leu86Arg | N-terminal | 2 | 1756 |
| insert C422-423 | Pro141frameshift | N-terminal | 3 | 1740 |
| insert C453-454 | Pro151frameshift | N-terminal | 3 | 2988 |
| insert C724-725 | Pro241frameshift | N-terminal | 4 | 2172 |
| ΔG885 | Val295frameshift | N-terminal | 4 | 2547 |
| C934T | Arg312Cys | N-terminal | 5 | 2622 |
| C1039T | Pro347Ser | N-terminal | 5 | 2796 |
| G1128A | splice | N-terminal | 5 | 3332 |
| A1129-2G | splice | N-terminal | intron 5 | 2941 |
| G1592A | Arg531Gln | S4 | 7 | 1697 |
| T1655C | Leu552Ser | S5 | 7 | 1816 |
| G1681A | Ala561Thr | S5 | 7 | 2985 |
| G1681A | Ala561Thr | S5 | 7 | 3414 |
| G1681A | Ala561Thr | S5 | 7 | 3985 |
| G1750A | Gly584Ser | S5/Pore | 7 | 3651 |
| G1755T | Trp585Cys | S5/Pore | 7 | 1789 |
| T1778C | Ile593Thr | S5/Pore | 7 | 3851 |
| G1810A | Gly604Ser | S5/Pore | 7 | 2750 |
| G1825A | Asp609Asn | S5/Pore | 7 | 1761 |
| C1838T | Thr613Met | Pore | 7 | 1789 |
| C1838T | Thr613Met | Pore | 7 | 1789 |
| C1838T | Thr613Met | Pore | 7 | 1989 |
| C1843G | Leu615Val | Pore | 7 | FamT |
| G1876A | Gly626Ser | Pore | 7 | 2672 |
| C1881G | Phe627Leu | Pore | 7 | 2925 |
| C1894T | Pro632Ser | Pore | 7 | 2740 |
| A1912G | Lys638Glu | S6 | 7 | 2814 |
| Δ1913-1915 | ΔLys638 | S6 | 7 | 3459 |
| A1933T | Met645Leu | S6 | 7 | 3376 |
| G2044T | Glu682Stop | S6/cNBD* | 8 | 1758 |
| insert T2218-2219 | His739frameshift | S6/cNBD | 9 | 2602 |
| C2254T | Arg752Trp | S6/cNBD | 9 | 2974 |
| ΔC2395 | Ile798frameshift | cNBD | 9 | 2961 |
| G2398 + 1C | splice | cNBD | intron 9 | 2015 |
| G2398 + 1C | splice | cNBD | intron 9 | 2027 |
| T2414C | Phe805Ser | cNBD | 10 | 3354 |
| T2414G | Phe805Cys | cNBD | 10 | 1977 |
| C2467T | Arg823Trp | cNBD | 10 | 2103 |
| C2467T | Arg823Trp | cNBD | 10 | 2723 |
| A2582T | Asn861Ile | C-terminal | 10 | 1815 |
| G2592 + 1A | splice | C-terminal | intron 10 | 1805 |
| ΔG2660 | Lys886frameshift | C-terminal | 11 | 3351 |
| C2750T | Pro917Leu | C-terminal | 12 | 1789 |
| ΔG2762 | Arg920frameshift | C-terminal | 12 | 3452 |
| C2764T | Arg922Trp | C-terminal | 12 | 1754 |
| insert G2775-2776 | Gly925frameshift | C-terminal | 12 | 2913 |
| ΔG2906 | Pro968frameshift | C-terminal | 12 | 2627 |
| Δ2959-2960 | Pro986frameshift | C-terminal | 12 | 2997 |
| G3003A | Trp1001Stop | C-terminal | 13 | 2808 |
| C3040T | Arg1014Stop | C-terminal | 13 | 2662 |
| C3040T | Arg1014Stop | C-terminal | 13 | 2754 |
| ΔC3094 | Gly1031frameshift | C-terminal | 13 | 2600 |
| insert C3303-3304 | Pro1101frameshift | C-terminal | 14 | 1789 |

*cNBD - cyclic nucleotide binding domain

De novo mutations of HERG in sporadic cases of LQT. To substantiate that HERG mutations cause LQT, SSCP was used to screen for mutations in sporadic cases. Primer pair 4-12 identified an aberrant conformer in affected individual II-1 of K2269 (FIG. 14A). This conformer was not identified in either parent or in more than 200 unaffected individuals. Direct DNA sequencing of the aberrant conformer identified a G to A substitution at position 1882. This mutation results in substitution of serine for a highly conserved glycine at codon 628 (G628S) (FIG. 14B), altering the pore forming domain. Genotype analysis of this kindred using nine informative STR polymorphisms confirmed maternity and paternity. The identification of a de novo mutation in a sporadic case demonstrates that HERG is LQT2. The mutations in K1697 and K1789 also arose de novo. Highly polymorphic short tandem repeats were used to confirm maternity and paternity in both cases (data not shown).

HERG is expressed in the heart. HERG was originally identified from a hippocampal cDNA library (Warmke and Ganetzky, 1994). To determine the tissue distribution of HERG mRNA, partial cDNA clones were isolated and used in Northern analyses. Northern analyses showed strongest hybridization to heart mRNAs, with faint signals in brain, liver, and pancreas (FIG. 15). Non-specific hybridization was also seen in lung, possibly due to genomic DNA contamination. The size of the bands observed in cardiac mRNA was consistent with the predicted size of HERG. Two bands, of ~4.1 and 4.4 kb were identified, possibly due to alternative splicing or the presence of a second related mRNA. These data indicate that HERG is strongly expressed in the heart, consistent with its involvement in LQT.

Mutations in HERG are one cause of LQT. It can be concluded that mutations in HERG cause the chromosome 7-linked form of LQT. Several lines of evidence support this conclusion. First, linkage analyses were used to map an LQT locus (LQT2) to chromosome 7q35-36 in 14 families. Second, physical and genetic mapping were used to place HERG in the same chromosomal region as LQT2. Third, it was demonstrated that HERG is expressed in the heart. Fourth, intragenic deletions of HERG associated with LQT in two families were identified. Fifth, four HERG point mutations in LQT patients were identified. Finally, three of the point mutations arose de novo and occurs within a highly conserved region encoding the potassium-selective pore domain.

The data suggest a likely molecular mechanism for chromosome 7-linked LQT. Although the function of HERG was not known, analyses of its predicted amino acid sequence indicated that it encodes a potassium channel α-subunit. Potassium channels are formed from four α-subunits (MacKinnon, 1991), either as homo- or hetero-tetramers (Covarrubias et al., 1991). These biophysical observations suggest that combination of normal and mutant HERG α-subunits could form abnormal HERG channels. This raises the possibility that HERG mutations have a dominant-negative effect on potassium channel function.

The mutations that were identified are consistent with a dominant-negative mechanism. Two mutations result in premature stop codons and truncated proteins (Δ1261 and the splice-donor mutation). In the first case, only the amino terminus and a portion of the first membrane spanning domain (S1) remain. In the second, the carboxyl end of the protein is truncated, leaving all membrane spanning domains intact. HERG contains a cyclic nucleotide binding domain near the carboxyl terminus, and in both mutations this domain is deleted. In another mutation, an in-frame deletion of nine amino acids disrupts the third membrane spanning domain (ΔI500-F508). Two missense mutations also affect membrane spanning domains, A561V in the S5 domain and N470D in S2. Both mutations affect amino acids conserved in the eag family of potassium channels and likely alter the protein's secondary structure. The de novo missense mutation, G628S, occurs in the pore-forming domain. This domain is highly conserved in all potassium channel α-subunits. This mutation affects a conserved amino acid that is of known importance for ion selectivity. When this substitution was introduced into Shaker H4, potassium ion selectivity was lost (Heginbotham et al., 1994). As discussed above, these mutations could induce the loss of HERG function.

The data have implications for the mechanism of arrhythmias in LQT. Two hypotheses for LQT have previously been proposed (Schwartz et al., 1994). One suggests that a predominance of left autonomic innervation causes abnormal cardiac repolarization and arrhythmias. This hypothesis is supported by the finding that arrhythmias can be induced in dogs by removal of the right stellate ganglion. In addition, anecdotal evidence suggests that some LQT patients are effectively treated by β-adrenergic blocking agents and by left stellate ganglionectomy (Schwartz et al., 1994). The second hypothesis for LQT-related arrhythmias suggests that mutations in cardiac-specific ion channel genes, or genes that modulate cardiac ion channels, cause delayed myocellular repolarization. Delayed myocellular repolarization could promote reactivation of L-type calcium channels, resulting in secondary depolarizations (January and Riddle, 1989). These secondary depolarizations are the likely cellular mechanism of torsade de pointes arrhythmias (Surawicz, 1989). This hypothesis is supported by the observation that pharmacologic block of potassium channels can induce QT prolongation and repolarization-related arrhythmias in humans and animal models (Antzelevitch and Sicouri, 1994). The discovery that one form of LQT results from mutations in a cardiac potassium channel gene supports the myocellular hypothesis.

The presence of a cyclic nucleotide binding domain in HERG suggests a mechanism for the link between altered autonomic nervous activity and arrhythmias in LQT. β-adrenergic receptor activation increases intracellular cAMP and enhances L-type $Ca^{2+}$ channel function. Cyclic AMP may also activate HERG, thereby increasing net outward current and accelerating the rate of myocellular repolarization. Dominant-negative mutations of HERG might interrupt the normal modulation of HERG function by cAMP, thereby permitting a predominant effect on L-type $Ca^{2+}$ channel function. The resulting imbalance would increase the likelihood that enhanced sympathetic tone could induce $Ca^{2+}$ channel-dependent secondary depolarizations, the probable cellular mechanism of torsade de pointes. β-adrenergic blocking agents could act by interrupting the effect of cAMP on L-type $Ca^{2+}$ channels, possibly explaining the beneficial effects of β-blockers in some LQT patients.

This work may have important clinical implications. Recently, presymptomatic diagnosis has been possible in large families using linkage analysis. Most cases of LQT are sporadic and therefore genetic testing using linkage analysis is not feasible. Continued mutational analyses of will facilitate genetic testing for LQT. Identification and characterization of genes responsible for other forms of LQT will be necessary for the development of generalized diagnostic tests. Improved diagnostic capacity may enable rational therapy. For example, chromosome 7-linked LQT patients may respond to potassium channel activators, like pinacidil.

EXAMPLE 12

Generation of Polyclonal Antibody Against HERG

Segments of HERG coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of HERG coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the HERG fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the HERG gene. These antibodies, in conjunction with antibodies to wild type HERG, are used to detect the presence and the relative level of the mutant forms in various tissues and biological fluids.

EXAMPLE 13

Generation of Monoclonal Antibodies Specific for HERG

Monoclonal antibodies are generated according to the following protocol. Mice are immunized with immunogen comprising intact HERG or HERG peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of HERG specific antibodies by ELISA or RIA using wild type or mutant HERG target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 14

Sandwich Assay for HERG

Monoclonal antibody is attached to a solid surface such as a plate, tube, bead, or particle. Preferably, the antibody is attached to the well surface of a 96-well ELISA plate. 100 µl sample (e.g., serum, urine, tissue cytosol) containing the HERG peptide/protein (wild-type or mutants) is added to the solid phase antibody. The sample is incubated for 2 hrs at room temperature. Next the sample fluid is decanted, and the solid phase is washed with buffer to remove unbound material. 100 µl of a second monoclonal antibody (to a different determinant on the HERG peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of HERG peptide/protein present in the sample, is quantified. Separate assays are performed using monoclonal antibodies which are specific for the wild-type HERG as well as monoclonal antibodies specific for each of the mutations identified in HERG.

EXAMPLE 15

Construction of an HERG Expression Plasmid and Transcription of cRNA

To facilitate HERG expression in Xenopus oocytes, the HERG cDNA was subcloned into a poly-A$^+$ expression vector and the 5' and 3' UTRs reduced to minimal lengths. The final HERG expression construct contains cDNA sequence from nucleotides −6 through 3513 in the pSP64 plasmid vector (Promega). Before use in expression experiments, the HERG construct was characterized by restriction mapping and DNA sequence analyses. Complementary RNAs for injection into oocytes were prepared with the mCAP RNA Capping Kit (Stratagene) following linearization of the expression construct with EcoRI.

EXAMPLE 16

Isolation of Oocytes and Injection of RNA

Xenopus frogs were anesthetized by immersion in 0.2% tricaine for 15-30 min. Ovarian lobes were digested with 2 mg/ml Type 1A collagenase (Sigma) in Ca$^{2+}$-free ND96 solution for 1.5 hours to remove follicle cells. Stage 1V and V oocytes (Dumont, 1972) were injected with HERG cRNA (0.05 mg/ml, 50 nl), then cultured in Barth's solution supplemented with 50 µg/ml gentamycin and 1 mM pyruvate at 18° C. Barth's solution contained (in mM): 88 NaCl, 1 KCl, 0.4 CaCl$_2$, 0.33 Ca(NO$_3$)$_2$, 1 MgSO$_4$, 2.4 NaHCO$_3$, 10 HEPES; pH 7.4.

EXAMPLE 17

Two-Microelectrode Voltage Clamp of Oocytes

Unless indicated, oocytes were bathed in ND96 solution. This solution contained (in mM): 96 NaCl, 2 KCl, 1 MgCl$_2$, 1.8 CaCl$_2$, 5 HEPES; pH 7.6. In some experiments, KCl was varied by equimolar substitution with NaCl. Currents were recorded at room temperature (21-23° C.) using standard two-microelectrode voltage clamp techniques. Glass microelectrodes were filled with 3 M KCl and their tips broken to obtain tip resistances of 1-3 MΩ for the voltage-recording electrode and 0.6-1 MΩ for the current-passing electrode. Oocytes were voltage-clamped with a Dagan TEV-200 amplifier. Voltage commands were generated using pClamp software (ver. 6, Axon Instruments), a 486DX2 personal computer and a TL-1 D/A interface (Axon Instruments). Current signals were digitally sampled at a rate equal to 2-4 times the low-pass cut-off frequency (−3 db) of a 4-pole Bessel filter. Unless indicated, currents were corrected for leak and capacitance using standard, on-line P/3 leak subtraction. The oocyte membrane potential was held at −70 mV between test pulses, applied at a rate of 1-3 pulses/min. Data analyses, including exponential fitting of current traces, were performed using pCLAMP. Fits of appropriate data to a Boltzmann function, or Goldman-Hodgkin-Katz constant field equation (Goldman, 1943; Hodgkin and Katz, 1949) were performed using (Synergy Software). Data are expressed as the mean±SEM (n=number of oocytes).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul, S. F., et al. (1997). Nucl. Acids Res. 25, 3389-3402.
Anand, R. (1992). *Techniques for the Analysis of Complex Genomes*, (Academic Press).
Anderson, W. F., et al. (1980). Proc. Natl. Acad. Sci. USA 77, 5399-5403.
Antzelevitch, C. and Sicouri, S. (1994). J. Am. Col. Card. 23, 259-277.
Ashford, M. L. J., et al. (1994). Nature 370, 456-459.
Attwell, D., et al. (1979). Pflugers Arch. 379, 137-142.
Ausubel, F. M., et al. (1992). *Current Protocols in Molecular Biology*, (John Wiley and Sons, New York, N.Y.)
Balser, J. R., et al. (1990). J. Gen. Physiol. 96, 835-863.
Bandyopadhyay, P. K. and Temin, H. M. (1984). Mol. Cell. Biol. 4, 749-754.
Bartel, P. L., et al. (1993). "Using the 2-hybrid system to detect protein-protein interactions." In *Cellular Interactions in Development: A Practical Approach*, Oxford University Press, pp. 153-179.
Bazette, H. C. (1920). Heart 7, 353-370.
Beaucage, S. L. and Caruthers, M. H. (1981). Tetra. Letts. 22, 1859-1862.
Benhorin, J., et al. (1993). Science 260, 1960-1962.
Berglund, P., et al. (1993). Biotechnology 11, 916-920.
Berkner, K. L., et al. (1988). BioTechniques 6, 616-629.
Berkner, K. L. (1992). Curr. Top. Microbiol. Immunol. 158, 39-66.
Blumenthal, E. M. and Kaczmarek, L. K. (1992). J. Neuroscience 12, 290-296.
Borman, S. (1996). Chemical & Engineering News, December 9 issue, pp. 42-43.
Breakefield, X. O. and Geller, A. I. (1987). Mol. Neurobiol. 1, 337-371.
Brinster, R. L., et al. (1981). Cell 27, 223-231.
Bruggemann, A., et al. (1993). Nature 365, 445-448.
Buchschacher, G. L. and Panganiban, A. T. (1992). J. Virol. 66, 2731-2739.
Capecchi, M. R. (1989). Science 244, 1288.
Cariello, N. F. (1988). Am. J. Human Genetics 42, 726-734.
Carmeliet, E. (1992). J. Pharm. Exp. Ther. 262, 809-817.
Chee M, et al. (1996). Science 274, 610-614.
Chevray, P. M. and Nathans, D. N. (1992). Proc. Natl. Acad. Sci. USA 89, 5789-5793.
Chinn, K. (1993). J. Pharmacol. Exp. Therap. 264, 553-560.
Compton, J. (1991). Nature 350, 91-92.
Conner, B. J., et al. (1983). Proc. Natl. Acad. Sci. USA 80, 278-282.
Costantini, F. and Lacy, E. (1981). Nature 294, 92-94.
Cotten, M., et al. (1990). Proc. Natl. Acad. Sci. USA 87, 4033-4037.
Cotton, R. G., et al. (1988). Proc. Natl. Acad. Sci. USA 85, 4397-4401.
Covarrubias, M., et al. (1991). Neuron 7, 763-773.
Culver, K. W., et al. (1992). Science 256, 1550-1552.
Culver, K. (1996). *Gene Therapy: A Primer for Physicians*, 2nd Ed., Mary Ann Liebert.
Curiel, D. T., et al. (1991). Proc. Natl. Acad. Sci. USA 88, 8850-8854.
Curiel, D. T., et al. (1992). Hum. Gene Ther. 3, 147-154.
Curran, M. E., et al. (1993a). Cell 73, 159-168.
Curran, M. E., et al. (1993b). J. Clin. Invest. 92, 799-803.
Curran, M. E., et al. (1995). Cell 80, 795-804.
Curry, P., et al. (1976). Lancet II, 231-233.
DeRisi, J., et al. (1996). Nat. Genet. 14, 457-460.
Deutscher, M. (1990). Meth. Enzymology 182, 83-89 (Academic Press, San Diego, Cal.).
Donehower, L. A., et al. (1992). Nature 356, 215.
Duggal, P. (1998). Circulation 97, 142-146.
Dumont, J. N. (1972). J. Morphol. 136, 153-180.
Editorial (1996). Nature Genetics 14, 367-370.
Elghanian, R., et al. (1997). Science 277, 1078-1081.
*Enhancers and Eukaryotic Gene Expression*, Cold Spring Harbor Press, Cold Spring Harbor, N.Y. (1983).
Erickson, J., et al. (1990). Science 249, 527-533.
Fahy, E., et al. (1991). PCR Methods Appl. 1, 25-33.
Fakler, B., et al. (1995). Cell 80, 149-154.
Feinberg, A. P. and Vogelstein, B. A. (1983). Anal. Biochem. 132, 6-13.
Felgner, P. L., et al. (1987). Proc. Natl. Acad. Sci. USA 84, 7413-7417.
Fields, S. and Song, O-K. (1989). Nature 340, 245-246.
Fiers, W., et al. (1978). Nature 273, 113-120.
Fink, D. J., et al. (1992). Hum. Gene Ther. 3, 11-19.
Fink, D. J., et al. (1996). Ann. Rev. Neurosci. 19, 265-287.
Finkelstein, J., et al. (1990). Genomics 7, 167-172.
Fodor, S. P. A. (1997). Science 277, 393-395.
Follmer, C. H., et al. (1992). Am. J. Physiol. 262, C75-C83.
Freese, A., et al. (1990). Biochem. Pharmacol. 40, 2189-2199.
Friedman, T. (1991). In *Therapy for Genetic Diseases*, T. Friedman, ed., Oxford University Press, pp. 105-121.
Gellens, M., et al. (1992). Proc. Natl. Acad. Sci. USA 89, 554-558.
George, A. L., et al. (1995). Cytogenet. Cell. Genet. 68, 67-70.
Gintant, G. A., et al. (1992). Time-dependent Outward Currents in the Heart. In *The Heart and Cardiovascular System*, H. A. Fozzard, R. B. Jennings, E. Haber, A. M. Katz and H. E. Morgan (eds.). New York, Raven Press, pp. 1121-1169.
Glover, D. (1985). DNA Cloning, I and II (Oxford Press).
Goding (1986). *Monoclonal Antibodies: Principles and Practice*, 2d ed. (Academic Press, N.Y.).
Godowski, P. J., et al. (1988). Science 241, 812-816.
Goldman, D. E. (1943). J. Gen. Physiol. 27, 37-60.
Gordon, J. W., et al. (1980). Proc. Natl. Acad. Sci. USA 77, 7380-7384.
Gorziglia, M. and Kapikian, A. Z. (1992). J. Virol. 66, 4407-4412.
Graham, F. L. and van der Eb, A. J. (1973). Virology 52, 456-467.
Green, E. D., et al. (1994). Hum. Mol. Genet. 3, 489-501.
Green, E. D., et al. (1995). Genomics 25, 170-183.
Grompe, M. (1993). Nature Genetics 5, 111-117.
Grompe, M., et al., (1989). Proc. Natl. Acad. Sci. USA 86, 5855-5892.
Guthrie, G., and Fink, G. R. (1991). *Guide to Yeast Genetics and Molecular Biology* (Academic Press).
Gyapay, G., et al. (1994). Nat. Genet. 7, 246-339.
Hacia, J. G., et al. (1996). Nature Genetics 14, 441-447.
Harlow, E. and Lane, D. (1988). Antibodies: A Laboratory Manual (Cold Spring Harbor Laboratory, Cold Spring Harbor, N.Y.).

Hasty, P. K., et al. (1991). Nature 350, 243.
Heginbotham, L., et al. (1994). Biophys. J. 66, 1061-1067
Helseth, E., et al. (1990). J. Virol. 64, 2416-2420.
Hodgkin, A. L. and Katz, B. (1949). J. Physiol (Lond.) 108, 37-77.
Hodgson, J. (1991). Bio/Technology 9, 19-21.
Huse, W. D., et al. (1989). Science 246, 1275-1281.
Innis, M. A., et al. (1990). *PCR Protocols: A Guide to Methods and Applications* (Academic Press, San Diego).
Jablonski, E., et al. (1986). Nucl. Acids Res. 14, 6115-6128.
Jakoby, W. B. and Pastan, I. H. (eds.) (1979). Cell Culture. Methods in Enzymology, volume 58 (Academic Press, Inc., Harcourt Brace Jovanovich (New York)).
January, C. T. and Riddle, J. M. (1989). Circ. Res. 64, 977-990.
Jervell, A. and Lange-Nielsen, F. (1957). Am. Heart J. 54, 59-78.
Jiang, C., et al. (1994). Nat. Genet. 8, 141-147.
Johnson, P. A., et al. (1992). J. Virol. 66, 2952-2965.
Johnson, et al. (1993). "Peptide Turn Mimetics" in *Biotechnology and Pharmacy*, Pezzuto et al., eds., Chapman and Hall, New York.
Jurkiewicz, N. K. and Sanguinetti, M. C. (1993). Circ. Res. 72, 75-83.
Kaneda, Y., et al. (1989). J. Biol. Chem. 264, 12126-12129.
Kanehisa, M. (1984). Nucl. Acids Res. 12, 203-213.
Kannel, W. B., et al. (1987). Am. Heart J. 113, 799-804.
Keating, M. T., et al. (1991a). Science 252, 704-706.
Keating, M. T., et al. (1991b). Am. J. Hum. Genet. 49, 1335-1339.
Keating, M. T. (1992). Circulation 85, 1973-1986.
Kinszler, K. W., et al. (1991). Science 251, 1366-1370.
Kohler, G. and Milstein, C. (1975). Nature 256, 495-497.
Kraemer, F. B., et al. (1993). J. Lipid Res. 34, 663-672.
Kubo, T., et al. (1988). FEBS Lett. 241, 119.
Kyte, J. and Doolittle, R. F. (1982). J. Mol. Biol. 157, 105-132.
Landegren, U., et al. (1988). Science 242, 229-237.
Lathrop, G. M., et al. (1985). Am. J. Hum. Genet. 37, 482-498.
Lee, J. E., et al. (1995). Science 268, 836-844.
Lichter, P., et al. (1988). Hum. Genet. 80, 224-234.
Lim, C. S., et al. (1991). Circulation 83, 2007-2011.
Lipshutz, R. J., et al. (1995). Biotechniques 19, 442-447.
Lockhart, D. J., et al. (1996). Nature Biotechnology 14, 1675-1680.
Lopez-Bameo, J., et al. (1993). Receptors and Channels 1, 61-71.
Ludwig, J., et al. (1994). EMBO J. 13, 4451-4458.
Lynch, J. J., et al. (1994). J. Pharmacol. Exp. Ther. 269, 541-554.
MacKinnon, R. (1991). Nature 350, 232-235.
Madzak, C., et al. (1992). J. Gen. Virol. 73, 1533-1536.
Maniatis, T. et al. (1982). *Molecular Cloning: A Laboratory Manual* (Cold Spring Harbor Laboratory, Cold Spring Harbor, N.Y.).
Mann, R. and Baltimore, D. (1985). J. Virol. 54, 401-407.
Marchuk, D., et al. (1990). Nucl. Acids Res. 19, 1154.
Margolskee, R. F. (1992). Curr. Top. Microbiol. Immunol. 158, 67-95.
Martin, R., et al. (1990). BioTechniques 9, 762-768.
Matteucci, M. D. and Caruthers, M. H. (1981). J. Am. Chem. Soc. 103, 3185.
Matthews, J. A. and Kricka, L. J. (1988). Anal. Biochem. 169, 1.
Merrifield, B. (1963). J. Am. Chem. Soc. 85, 2149-2156.
Metzger, D., et al. (1988). Nature 334, 31-36.
Mifflin, T. E. (1989). Clinical Chem. 35, 1819-1825.
Miller, A. D. (1992). Curr. Top. Microbiol. Immunol. 158, 1-24.
Miller, A. D., et al. (1985). Mol. Cell. Biol. 5, 431-437.
Miller, A. D., et al. (1988). J. Virol. 62, 4337-4345.
Modrich, P. (1991). Ann. Rev. Genet. 25, 229-253.
Mombaerts, P., et al. (1992). Cell 68, 869.
Moss, A. J., et al. (1991). Circulation 84, 1136-1144.
Moss, B. (1992). Curr. Top. Microbiol. Immunol. 158, 25-38.
Moss, B. (1996). Proc. Natl. Acad. Sci. USA 93, 11341-11348.
Muzyczka, N. (1992). Curr. Top. Microbiol. Immunol. 158, 97-129.
Nabel, E. G., et al. (1990). Science 249, 1285-1288.
Nabel (1992). Hum. Gene Ther. 3, 399-410.
Naldini, L., et al. (1996). Science 272, 263-267.
Newton, C. R., et al. (1989). Nucl. Acids Res. 17, 2503-2516.
Neyroud, N., et al. (1997). Nat. Genet. 15, 186-189.
Nguyen, Q., et al. (1992). BioTechniques 13, 116-123.
Novack, D. F., et al. (1986). Proc. Natl. Acad. Sci. USA 83, 586-590.
Ohi, S., et al. (1990). Gene 89, 279-282.
Orita, M., et al. (1989). Proc. Natl. Acad. Sci. USA 86, 2766-2770.
Page, K. A., et al. (1990). J. Virol. 64, 5270-5276.
Pardo, L. A., et al. (1992). Proc. Natl. Acad. Sci. USA 89, 2466-2470.
Pellicer, A., et al. (1980). Science 209, 1414-1422.
Petropoulos, C. J., et al. (1992). J. Virol. 66, 3391-3397.
Philpott, K. L., et al. (1992). Science 256, 1448.
Ptacek, L. J., et al. (1991). Cell 67, 1021-1027.
Quantin, B., et al. (1992). Proc. Natl. Acad. Sci. USA 89, 2581-2584. *Remington's Pharmaceutical Sciences*, 18th Ed. (1990, Mack Publishing Co., Easton, Pa.).
Rigby, P. W. J., et al. (1977). J. Mol. Biol. 113, 237-251.
Roden, D. M. (1988). Arrhythmogenic Potential of Class III Antiarrhythmic Agents: Comparison with Class I Agents. In *Control of Cardiac Arrhythmias by Lengthening Repolarization*, B. N. Singh (ed.). Mt. Kisco, N.Y., Futura Publishing Co., pp. 559-576.
Romano, C. (1965). Congenital cardiac arrhythmia. Lancet 1658-659.
Rosenfeld, M. A., et al. (1992). Cell 68, 143-155.
Ruano, G. and Kidd, K. K. (1989). Nucl. Acids Res. 17, 8392.
Russell, D. and Hirata, R. (1998). Nature Genetics 18, 323-328.
Sambrook, J., et al. (1989). *Molecular Cloning: A Laboratory Manual*, 2nd Ed. (Cold Spring Harbor Laboratory, Cold Spring Harbor, N.Y.).
Sanguinetti, M. C. and Jurkiewicz, N. K. (1990). Am. J. Physiol. 259, H1881-H1889.
Sanguinetti, M. C. and Jurkiewicz, N. K. (1990). J. Gen. Physiol. 96, 195-215.
Sanguinetti, M. C. and Jurkiewicz, N. K. (1991). Am. J. Physiol. 260, H393-H399.
Sanguinetti, M. C. and Jurkiewicz, N. K. (1992). Pflugers Archiv 420, 180-186.
Sanguinetti, M. C., et al. (1991). Circ. Res. 68, 77-84.
Scamps, F. and Carmeliet, E. (1989). Am. J. Physiol. 257, C1086-C1092.
Scharf, S. J., et al. (1986). Science 233, 1076-1078.
Schneider, G., et al. (1998). Nature Genetics 18, 180-183.
Schultze-Bahr, E., et al. (1997). Nat. Genet. 17, 267-268.
Schwartz, P. J., et al. (1975). Am. Heart J. 109, 378-390.
Schwartz, P. J., et al. (1994). The long QT syndrome. In Cardiac Electrophysiology: from cell to bedside. D. P. Zipes and J. Jalife eds. (W. B. Sanders Company) pp.788-811.

Scopes, R. (1982). *Protein Purification: Principles and Practice*, (Springer-Verlag, N.Y.).
Sheffield, V. C., et al. (1989). Proc. Natl. Acad. Sci. USA 86, 232-236.
Sheffield, V. C., et al., 1991. Am. J. Hum. Genet. 49, 699-706.
Shenk, T. E., et al. (1975). Proc. Natl. Acad. Sci. USA 72, 989-993.
Shibasaki, T. (1987). J. Physiol. 387, 227-250.
Shimada, T., et al. (1991). J. Clin. Invest. 88, 1043-1047.
Shinkai, Y., et al. (1992). Cell 68, 855.
Shoemaker, D. D., et al. (1996). Nature Genetics 14, 450-456.
Snouwaert, J. N., et al. (1992). Science 257, 1083.
Sorge, J., et al. (1984). Mol. Cell. Biol. 4, 1730-1737.
Spargo, C. A., et al. (1996). Mol. Cell. Probes 10, 247-256.
Splawski, I., et al. (1997). Nat. Genet. 17, 338-340.
Stemberg, N. (1990). Proc. Natl. Acad. Sci. USA 87, 103-107.
Stewart, M. J., et al. (1992). Hum. Gene Ther. 3, 267-275.
Stratford-Perricaudet, L. D., et al. (1990). Hum. Gene Ther. 1, 241-256.
Surawicz, B. (1989). J. Am. Coll. Cardiol. 14, 172-184.
Towbin, J. A., et al. (1994). Circulation 90, 2635-2644.
Tyson, J., et al. (1997). Hum. Mol. Genet. 6, 2179-2185.
Valancius, V. and Smithies, 0. (1991). Mol. Cell Biol. 11, 1402.
Vetter, D. E., et al. (1996). Neuron 17, 1251-1264.
Vandenberg, C. A. (1987). Proc. Natl. Acad. Sci. USA 84, 2560-2564.
Vincent, G. M., et al. (1992). N. Engl. J. Med. 327, 846-852.
Wagner, E., et al. (1991). Proc. Natl. Acad. Sci. USA 88, 4255-4259.
Wagner, E., et al. (1990). Proc. Natl. Acad. Sci. USA 87, 3410-3414. Walker, G. T., et al., (1992). Nucl. Acids Res. 20, 1691-1696.
Wang, C. Y. and Huang, L. (1989). Biochemistry 28, 9508-9514.
Wang, Q. and Keating, M. T. (1994). BioTechniques 17, 282-284.
Wang, Q., et al. (1995). Cell 80, 805-811.
Wang, Q., et al. (1996). Nat. Genet. 12, 17-23.
Ward, 0. C. (1964). J. Ir. Med. Assoc. 54, 103-106.
Warmke, J. E. and Ganetzky, B. (1994). Proc. Natl. Acad. Sci. 91, 3438-3442.
Wartell, R. M., et al. (1990). Nucl. Acids Res. 18, 2699-2705.
Wells, J. A. (1991). Methods Enzymol. 202, 390-411.
Wetmur, J. G. and Davidson, N. (1968). J. Mol. Biol. 31, 349-370.
White, M. B., et al. (1992). Genomics 12, 301-306.
White, R. and Lalouel, J. M. (1988). Annu. Rev. Genet. 22, 259-279.
Wilkinson, G. W. and Akrigg, A. (1992). Nucleic Acids Res. 20, 2233-2239.
Willich, S. N., et al. (1987). Am. J. Cardiol. 60, 801-806.
Wolff, J. A., et al. (1990). Science 247, 1465-1468.
Wolff, J. A., et al. (1991). BioTechniques 11, 474-485.
Wu, D. Y. and Wallace, R. B. (1989). Genomics 4, 560-569.
Wu, C. H., et al. (1989). J. Biol. Chem. 264, 16985-16987.
Wu, G. Y., et al. (1991). J. Biol. Chem. 266, 14338-14342.
Yang, N., et al. (1994). Proc. Natl. Acad. Sci. USA 91, 12785-12789.
Yang, T., et al. (1994). Circ. Res. 75, 870-878.
Zenke, M., et al. (1990). Proc. Natl. Acad. Sci. USA 87, 3655-3659.
Zipes, D. P. (1987). Am. J. Cardiol. 59, 26E-31E.

Patents and Patent Applications:
European Patent Application Publication No. 0332435.
EPO Publication No. 225,807.
Hitzeman et al., EP 73,675A.
EP 425,731A.
WO 84/03564.
WO 90/07936.
WO 92/19195.
WO 93/07282.
WO 94/25503.
WO 95/01203.
WO 95/05452.
WO 96/02286.
WO 96/02646.
WO 96/11698.
WO 96/40871.
WO 96/40959.
WO 97/02048.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,554,101.
U.S. Pat. No. 4,683,195.
U.S. Pat. No. 4,683,202.
U.S. Pat. No. 4,816,567.
U.S. Pat. No. 4,868,105.
U.S. Pat. No. 5,252,479.
U.S. Pat. No. 5,270,184.
U.S. Pat. No. 5,409,818.
U.S. Pat. No. 5,436,146.
U.S. Pat. No. 5,455,166.
U.S. Pat. No. 5,550,050.
U.S. Pat. No. 5,599,673.
U.S. Pat. No. 5,691,198.
U.S. Pat. No. 5,735,500.
U.S. Pat. No. 5,747,469.

What is claimed is:

1. A method for detecting a mutation which causes or is associated with long QT syndrome comprising amplifying any one of exons 1-15 of HERG with a pair of primers such that the entire exon, and no other exon or portion thereof, is amplified, and analyzing the amplified exon for a mutation which causes or is associated with long QT syndrome, wherein the pair of primers is selected from the group consisting of:
   a) SEQ ID NOs:56 and 57;
   b) SEQ ID NOs:58 and 59;
   c) SEQ ID NOs:60 and 61;
   d) SEQ ID NOs:62 and 63;
   e) SEQ ID NQs:64 and 65;
   f) SEQ ID NOs:66 and 67;
   g) SEQ ID NOs:68 and 69;
   h) SEQ ID NOs:70 and 71;
   i) SEQ ID NOs:76 and 77;
   j) SEQ ID NOs:78 and 79;
   k) SEQ ID NOs:80 and 81;
   l) SEQ ID NOs:82 and 83;
   m) SEQ ID NOs:84 and 85;
   n) SEQ ID NOs:86 and 87;
   o) SEQ ID NOs:88 and 89;
   p) SEQ ID NOs:90 and 91;
   q) SEQ ID NOs:92 and 93; and
   r) SEQ ID NOs:94 and 95.

2. The method of claim 1, wherein the analyzing step is performed by singe-stranded conformation polymorphism technique.

3. The method of claim 1, wherein the analyzing step is performed by sequencing the amplified exon.

4. A method for detecting a mutation which causes or is associated with long QT syndrome comprising amplifying any two or more of exons 1-15 of HERG with a pair of primers for each exon such that the entire exon, and no other exon or portion thereof, is amplified for each of the two or more exons, and analyzing the amplified exons for a mutation which causes or is associated with long QT syndrome, wherein the pairs of primers is selected from the group consisting of:
   a) SEQ ID NOs:56 and 57;
   b) SEQ ID NOs:58 and 59;
   c) SEQ ID NOs:60 and 61;
   d) SEQ ID NOs:62 and 63;
   e) SEQ ID NOs:64 and 65;
   f) SEQ ID NOs:66 and 67;
   g) SEQ ID NOs:68 and 69;
   h) SEQ ID NOs:70 and 71;
   i) SEQ ID NOs:76 and 77;
   j) SEQ ID NOs:78 and 79;
   k) SEQ ID NOs:80 and 81;
   l) SEQ ID NOs:82 and 83;
   m) SEQ ID NOs:84 and 85;
   n) SEQ ID NOs:86 and 87;
   o) SEQ ID NOs:88 and 89;
   p) SEQ ID NOs:90 and 91;
   q) SEQ ID NOs:92 and 93; and
   r) SEQ ID NOs:94 and 95.

5. The method of claim 4 wherein the analyzing step is performed by singe-stranded conformation polymorphism technique.

6. The method of claim 4 wherein the analyzing step is performed by sequencing the amplified exon.

7. The method of claim 4 wherein all 15 exons of HERG are amplified.

* * * * *

SEQUENCE LISTING

<160> NUMBER OF SEQ ID NOS: 116

<210> SEQ ID NO 1
<211> LENGTH: 3480
<212> TYPE: DNA

```
<213> ORGANISM: Homo sapiens
<220> FEATURE:
<221> NAME/KEY: CDS
<222> LOCATION: (1)..(3477)

<400> SEQUENCE: 1 atg ccg gtg cgg agg ggc cac gtc gcg ccg cag aac acc ttc ctg gac      48
Met Pro Val Arg Arg Gly His Val Ala Pro Gln Asn Thr Phe Leu Asp
 1               5                  10                  15 acc atc atc cgc aag ttt gag ggc cag agc cgt aag ttc atc atc gcc      96
Thr Ile Ile Arg Lys Phe Glu Gly Gln Ser Arg Lys Phe Ile Ile Ala
             20                  25                  30 aac gct cgg gtg gag aac tgc gcc gtc atc tac tgc aac gac ggc ttc     144
Asn Ala Arg Val Glu Asn Cys Ala Val Ile Tyr Cys Asn Asp Gly Phe
         35                  40                  45 tgc gag ctg tgc ggc tac tcg cgg gcc gag gtg atg cag cga ccc tgc     192
Cys Glu Leu Cys Gly Tyr Ser Arg Ala Glu Val Met Gln Arg Pro Cys
     50                  55                  60 acc tgc gac ttc ctg cac ggg ccg cgc acg cag cgc cgc gct gcc gcg     240
Thr Cys Asp Phe Leu His Gly Pro Arg Thr Gln Arg Arg Ala Ala Ala
 65                  70                  75                  80 cag atc gcg cag gca ctg ctg ggc gcc gag gag cgc aaa gtg gaa atc     288
Gln Ile Ala Gln Ala Leu Leu Gly Ala Glu Glu Arg Lys Val Glu Ile
                 85                  90                  95 gcc ttc tac cgg aaa gat ggg agc tgc ttc cta tgt ctg gtg gat gtg     336
Ala Phe Tyr Arg Lys Asp Gly Ser Cys Phe Leu Cys Leu Val Asp Val
            100                 105                 110 gtg ccc gtg aag aac gag gat ggg gct gtc atc atg ttc atc ctc aat     384
Val Pro Val Lys Asn Glu Asp Gly Ala Val Ile Met Phe Ile Leu Asn
        115                 120                 125 ttc gag gtg gtg atg gag aag gac atg gtg ggg tcc ccg gct cat gac     432
Phe Glu Val Val Met Glu Lys Asp Met Val Gly Ser Pro Ala His Asp
    130                 135                 140 acc aac cac cgg ggc ccc ccc acc agc tgg ctg gcc cca ggc cgc gcc     480
Thr Asn His Arg Gly Pro Pro Thr Ser Trp Leu Ala Pro Gly Arg Ala
145                 150                 155                 160 aag acc ttc cgc ctg aag ctg ccc gcg ctg ctg gcg ctg acg gcc cgg     528
Lys Thr Phe Arg Leu Lys Leu Pro Ala Leu Leu Ala Leu Thr Ala Arg
                165                 170                 175 gag tcg tcg gtg cgg tcg ggc ggc gcg ggc ggc gcg ggc gcc ccg ggg     576
Glu Ser Ser Val Arg Ser Gly Gly Ala Gly Gly Ala Gly Ala Pro Gly
            180                 185                 190 gcc gtg gtg gtg gac gtg gac ctg acg ccc gcg gca ccc agc agc gag     624
Ala Val Val Val Asp Val Asp Leu Thr Pro Ala Ala Pro Ser Ser Glu
        195                 200                 205 tcg ctg gcc ctg gac gaa gtg aca gcc atg gac aac cac gtg gca ggg     672
Ser Leu Ala Leu Asp Glu Val Thr Ala Met Asp Asn His Val Ala Gly
    210                 215                 220 ctc ggg ccc gcg gag gag cgg cgt gcg ctg gtg ggt ccc ggc tct ccg     720
Leu Gly Pro Ala Glu Glu Arg Arg Ala Leu Val Gly Pro Gly Ser Pro
225                 230                 235                 240 ccc cgc agc gcg ccc ggc cag ctc cca tcg ccc cgg gcg cac agc ctc     768
Pro Arg Ser Ala Pro Gly Gln Leu Pro Ser Pro Arg Ala His Ser Leu
                245                 250                 255 aac ccc gac gcc tcg ggc tcc agc tgc agc ctg gcc cgg acg cgc tcc     816
Asn Pro Asp Ala Ser Gly Ser Ser Cys Ser Leu Ala Arg Thr Arg Ser
            260                 265                 270 cga gaa agc tgc gcc agc gtg cgc cgc gcc tcg tcg gcc gac gac atc     864
Arg Glu Ser Cys Ala Ser Val Arg Arg Ala Ser Ser Ala Asp Asp Ile
        275                 280                 285
```

-continued

| | |
|---|---|
| gag gcc atg cgc gcc ggg gtg ctg ccc ccg cca ccg cgc cac gcc agc<br>Glu Ala Met Arg Ala Gly Val Leu Pro Pro Pro Pro Arg His Ala Ser<br>290                                      295                             300 | 912 |
| acc ggg gcc atg cac cca ctg cgc agc ggc ttg ctc aac tcc acc tcg<br>Thr Gly Ala Met His Pro Leu Arg Ser Gly Leu Leu Asn Ser Thr Ser<br>305                                 310                           315                  320 | 960 |
| gac tcc gac ctc gtg cgc tac cgc acc att agc aag att ccc caa atc<br>Asp Ser Asp Leu Val Arg Tyr Arg Thr Ile Ser Lys Ile Pro Gln Ile<br>                        325                               330                          335 | 1008 |
| acc ctc aac ttt gtg gac ctc aag ggc gac ccc ttc ttg gct tcg ccc<br>Thr Leu Asn Phe Val Asp Leu Lys Gly Asp Pro Phe Leu Ala Ser Pro<br>                340                           345                           350 | 1056 |
| acc agt gac cgt gag atc ata gca cct aag ata aag gag cga acc cac<br>Thr Ser Asp Arg Glu Ile Ile Ala Pro Lys Ile Lys Glu Arg Thr His<br>355                                      360                           365 | 1104 |
| aat gtc act gag aag gtc acc cag gtc ctg tcc ctg ggc gcc gac gtg<br>Asn Val Thr Glu Lys Val Thr Gln Val Leu Ser Leu Gly Ala Asp Val<br>    370                           375                           380 | 1152 |
| ctg cct gag tac aag ctg cag gca ccg cgc atc cac cgc tgg acc atc<br>Leu Pro Glu Tyr Lys Leu Gln Ala Pro Arg Ile His Arg Trp Thr Ile<br>385                                    390                           395                  400 | 1200 |
| ctg cat tac agc ccc ttc aag gcc gtg tgg gac tgg ctc atc ctg ctg<br>Leu His Tyr Ser Pro Phe Lys Ala Val Trp Asp Trp Leu Ile Leu Leu<br>                        405                               410                          415 | 1248 |
| ctg gtc atc tac acg gct gtc ttc aca ccc tac tcg gct gcc ttc ctg<br>Leu Val Ile Tyr Thr Ala Val Phe Thr Pro Tyr Ser Ala Ala Phe Leu<br>                420                           425                           430 | 1296 |
| ctg aag gag acg gaa gaa ggc ccg cct gct acc gag tgt ggc tac gcc<br>Leu Lys Glu Thr Glu Glu Gly Pro Pro Ala Thr Glu Cys Gly Tyr Ala<br>                            435                             440                           445 | 1344 |
| tgc cag ccg ctg gct gtg gtg gac ctc atc gtg gac atc atg ttc att<br>Cys Gln Pro Leu Ala Val Val Asp Leu Ile Val Asp Ile Met Phe Ile<br>450                                      455                           460 | 1392 |
| gtg gac atc ctc atc aac ttc cgc acc acc tac gtc aat gcc aac gag<br>Val Asp Ile Leu Ile Asn Phe Arg Thr Thr Tyr Val Asn Ala Asn Glu<br>465                                      470                           475                  480 | 1440 |
| gag gtg gtc agc cac ccc ggc cgc atc gcc gtc cac tac ttc aag ggc<br>Glu Val Val Ser His Pro Gly Arg Ile Ala Val His Tyr Phe Lys Gly<br>                        485                               490                          495 | 1488 |
| tgg ttc ctc atc gac atg gtg gcc gcc atc ccc ttc gac ctg ctc atc<br>Trp Phe Leu Ile Asp Met Val Ala Ala Ile Pro Phe Asp Leu Leu Ile<br>                500                           505                           510 | 1536 |
| ttc ggc tct ggc tct gag gag ctg atc ggg ctg ctg aag act gcg cgg<br>Phe Gly Ser Gly Ser Glu Glu Leu Ile Gly Leu Leu Lys Thr Ala Arg<br>              515                           520                           525 | 1584 |
| ctg ctg cgg ctg gtg cgc gtg gcg cgg aag ctg gat cgc tac tca gag<br>Leu Leu Arg Leu Val Arg Val Ala Arg Lys Leu Asp Arg Tyr Ser Glu<br>530                                      535                           540 | 1632 |
| tac ggc gcg gcc gtg ctg ttc ttg ctc atg tgc acc ttt gcg ctc atc<br>Tyr Gly Ala Ala Val Leu Phe Leu Leu Met Cys Thr Phe Ala Leu Ile<br>545                                      550                           555                  560 | 1680 |
| gcg cac tgg cta gcc tgc atc tgg tac gcc atc ggc aac atg gag cag<br>Ala His Trp Leu Ala Cys Ile Trp Tyr Ala Ile Gly Asn Met Glu Gln<br>                        565                               570                          575 | 1728 |
| cca cac atg gac tca cgc atc ggc tgg ctg cac aac ctg ggc gac cag<br>Pro His Met Asp Ser Arg Ile Gly Trp Leu His Asn Leu Gly Asp Gln<br>                580                           585                           590 | 1776 |
| ata ggc aaa ccc tac aac agc agc ggc ctg ggc ggc ccc tcc atc aag<br>Ile Gly Lys Pro Tyr Asn Ser Ser Gly Leu Gly Gly Pro Ser Ile Lys<br>                        595                               600                          605 | 1824 |

-continued

```
gac aag tat gtg acg gcg ctc tac ttc acc ttc agc agc ctc acc agt    1872
Asp Lys Tyr Val Thr Ala Leu Tyr Phe Thr Phe Ser Ser Leu Thr Ser
610                 615                 620 gtg ggc ttc ggc aac gtc tct ccc aac acc aac tca gag aag atc ttc    1920
Val Gly Phe Gly Asn Val Ser Pro Asn Thr Asn Ser Glu Lys Ile Phe
625                 630                 635                 640 tcc atc tgc gtc atg ctc att ggc tcc ctc atg tat gct agc atc ttc    1968
Ser Ile Cys Val Met Leu Ile Gly Ser Leu Met Tyr Ala Ser Ile Phe
                645                 650                 655 ggc aac gtg tcg gcc atc atc cag cgg ctg tac tcg ggc aca gcc cgc    2016
Gly Asn Val Ser Ala Ile Ile Gln Arg Leu Tyr Ser Gly Thr Ala Arg
            660                 665                 670 tac cac aca cag atg ctg cgg gtg cgg gag ttc atc cgc ttc cac cag    2064
Tyr His Thr Gln Met Leu Arg Val Arg Glu Phe Ile Arg Phe His Gln
        675                 680                 685 atc ccc aat ccc ctg cgc cag cgc ctc gag gag tac ttc cag cac gcc    2112
Ile Pro Asn Pro Leu Arg Gln Arg Leu Glu Glu Tyr Phe Gln His Ala
    690                 695                 700 tgg tcc tac acc aac ggc atc gac atg aac gcg gtg ctg aag ggc ttc    2160
Trp Ser Tyr Thr Asn Gly Ile Asp Met Asn Ala Val Leu Lys Gly Phe
705                 710                 715                 720 cct gag tgc ctg cag gct gac atc tgc ctg cac ctg aac cgc tca ctg    2208
Pro Glu Cys Leu Gln Ala Asp Ile Cys Leu His Leu Asn Arg Ser Leu
                725                 730                 735 ctg cag cac tgc aaa ccc ttc cga ggg gcc acc aag ggc tgc ctt cgg    2256
Leu Gln His Cys Lys Pro Phe Arg Gly Ala Thr Lys Gly Cys Leu Arg
            740                 745                 750 gcc ctg gcc atg aag ttc aag acc aca cat gca ccg cca ggg gac aca    2304
Ala Leu Ala Met Lys Phe Lys Thr Thr His Ala Pro Pro Gly Asp Thr
        755                 760                 765 ctg gtg cat gct ggg gac ctg ctc acc gcc ctg tac ttc atc tcc cgg    2352
Leu Val His Ala Gly Asp Leu Leu Thr Ala Leu Tyr Phe Ile Ser Arg
    770                 775                 780 ggc tcc atc gag atc ctg cgg ggc gac gtc gtc gtg gcc atc ctg ggg    2400
Gly Ser Ile Glu Ile Leu Arg Gly Asp Val Val Val Ala Ile Leu Gly
785                 790                 795                 800 aag aat gac atc ttt ggg gag cct ctg aac ctg tat gca agg cct ggc    2448
Lys Asn Asp Ile Phe Gly Glu Pro Leu Asn Leu Tyr Ala Arg Pro Gly
                805                 810                 815 aag tcg aac ggg gat gtg cgg gcc ctc acc tac tgt gac cta cac aag    2496
Lys Ser Asn Gly Asp Val Arg Ala Leu Thr Tyr Cys Asp Leu His Lys
            820                 825                 830 atc cat cgg gac gac ctg ctg gag gtg ctg gac atg tac cct gag ttc    2544
Ile His Arg Asp Asp Leu Leu Glu Val Leu Asp Met Tyr Pro Glu Phe
        835                 840                 845 tcc gac cac ttc tgg tcc agc ctg gag atc acc ttc aac ctg cga gat    2592
Ser Asp His Phe Trp Ser Ser Leu Glu Ile Thr Phe Asn Leu Arg Asp
    850                 855                 860 acc aac atg atc ccg ggc tcc ccc ggc agt acg gag tta gag ggt ggc    2640
Thr Asn Met Ile Pro Gly Ser Pro Gly Ser Thr Glu Leu Glu Gly Gly
865                 870                 875                 880 ttc agt cgg caa cgc aag cgc aag ttg tcc ttc cgc agg cgc acg gac    2688
Phe Ser Arg Gln Arg Lys Arg Lys Leu Ser Phe Arg Arg Arg Thr Asp
                885                 890                 895 aag gac acg gag cag cca ggg gag gtg tcg gcc ttg ggg ccg ggc cgg    2736
Lys Asp Thr Glu Gln Pro Gly Glu Val Ser Ala Leu Gly Pro Gly Arg
            900                 905                 910 gcg ggg gca ggg ccg agt agc cgg ggc cgg ccg ggg ggg ccg tgg ggg    2784
Ala Gly Ala Gly Pro Ser Ser Arg Gly Arg Pro Gly Gly Pro Trp Gly
```

```
                915                 920                 925
gag agc ccg tcc agt ggc ccc tcc agc cct gag agc agt gag gat gag    2832
Glu Ser Pro Ser Ser Gly Pro Ser Ser Pro Glu Ser Ser Glu Asp Glu
        930                 935                 940 ggc cca ggc cgc agc tcc agc ccc ctc cgc ctg gtg ccc ttc tcc agc    2880
Gly Pro Gly Arg Ser Ser Ser Pro Leu Arg Leu Val Pro Phe Ser Ser
945                 950                 955                 960 ccc agg ccc ccc gga gag ccg ccg ggt ggg gag ccc ctg atg gag gac    2928
Pro Arg Pro Pro Gly Glu Pro Pro Gly Gly Glu Pro Leu Met Glu Asp
                965                 970                 975 tgc gag aag agc agc gac act tgc aac ccc ctg tca ggc gcc ttc tca    2976
Cys Glu Lys Ser Ser Asp Thr Cys Asn Pro Leu Ser Gly Ala Phe Ser
        980                 985                 990 gga gtg tcc aac att ttc agc ttc tgg ggg gac agt cgg ggc cgc cag    3024
Gly Val Ser Asn Ile Phe Ser Phe Trp Gly Asp Ser Arg Gly Arg Gln
995                 1000                1005 tac cag gag ctc cct cga tgc ccc gcc ccc acc ccc agc ctc ctc aac    3072
Tyr Gln Glu Leu Pro Arg Cys Pro Ala Pro Thr Pro Ser Leu Leu Asn
        1010                1015                1020 atc ccc ctc tcc agc ccg ggt cgg cgg ccc cgg ggc gac gtg gag agc    3120
Ile Pro Leu Ser Ser Pro Gly Arg Arg Pro Arg Gly Asp Val Glu Ser
1025                1030                1035                1040 agg ctg gat gcc ctc cag cgc cag ctc aac agg ctg gag acc cgg ctg    3168
Arg Leu Asp Ala Leu Gln Arg Gln Leu Asn Arg Leu Glu Thr Arg Leu
                1045                1050                1055 agt gca gac atg gcc act gtc ctg cag ctg cta cag agg cag atg acg    3216
Ser Ala Asp Met Ala Thr Val Leu Gln Leu Leu Gln Arg Gln Met Thr
        1060                1065                1070 ctg gtc ccg ccc gcc tac agt gct gtg acc acc ccg ggg cct ggc ccc    3264
Leu Val Pro Pro Ala Tyr Ser Ala Val Thr Thr Pro Gly Pro Gly Pro
1075                1080                1085 act tcc aca tcc ccg ctg ttg ccc gtc agc ccc ctc ccc acc ctc acc    3312
Thr Ser Thr Ser Pro Leu Leu Pro Val Ser Pro Leu Pro Thr Leu Thr
        1090                1095                1100 ttg gac tcg ctt tct cag gtt tcc cag ttc atg gcg tgt gag gag ctg    3360
Leu Asp Ser Leu Ser Gln Val Ser Gln Phe Met Ala Cys Glu Glu Leu
1105                1110                1115                1120 ccc ccg ggg gcc cca gag ctt ccc caa gaa ggc ccc aca cga cgc ctc    3408
Pro Pro Gly Ala Pro Glu Leu Pro Gln Glu Gly Pro Thr Arg Arg Leu
                1125                1130                1135 tcc cta ccg ggc cag ctg ggg gcc ctc acc tcc cag ccc ctg cac aga    3456
Ser Leu Pro Gly Gln Leu Gly Ala Leu Thr Ser Gln Pro Leu His Arg
        1140                1145                1150 cac ggc tcg gac ccg ggc agt tag                                    3480
His Gly Ser Asp Pro Gly Ser
        1155
```

<210> SEQ ID NO 2
<211> LENGTH: 1159
<212> TYPE: PRT
<213> ORGANISM: Homo sapiens

<400> SEQUENCE: 2

```
Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45
```

-continued

```
Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65              70                  75                          80

Gln Ile Ala Gln Ala Leu Leu Gly Ala Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Ala Gly Gly Ala Gly Ala Pro Gly
            180                 185                 190

Ala Val Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
            210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
            275                 280                 285

Glu Ala Met Arg Ala Gly Val Leu Pro Pro Pro Arg His Ala Ser
290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
            355                 360                 365

Asn Val Thr Glu Lys Val Thr Gln Val Leu Ser Leu Gly Ala Asp Val
370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
            435                 440                 445

Cys Gln Pro Leu Ala Val Val Asp Leu Ile Val Asp Ile Met Phe Ile
450                 455                 460

Val Asp Ile Leu Ile Asn Phe Arg Thr Thr Tyr Val Asn Ala Asn Glu
```

-continued

```
            465                 470                 475                 480
Glu Val Val Ser His Pro Gly Arg Ile Ala Val His Tyr Phe Lys Gly
                485                 490                 495
Trp Phe Leu Ile Asp Met Val Ala Ile Pro Phe Asp Leu Leu Ile
                500                 505                 510
Phe Gly Ser Gly Ser Glu Glu Leu Ile Gly Leu Leu Lys Thr Ala Arg
                515                 520                 525
Leu Leu Arg Leu Val Arg Val Ala Arg Lys Leu Asp Arg Tyr Ser Glu
            530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
                565                 570                 575
Pro His Met Asp Ser Arg Ile Gly Trp Leu His Asn Leu Gly Asp Gln
                580                 585                 590
Ile Gly Lys Pro Tyr Asn Ser Ser Gly Leu Gly Gly Pro Ser Ile Lys
                595                 600                 605
Asp Lys Tyr Val Thr Ala Leu Tyr Phe Thr Phe Ser Ser Leu Thr Ser
            610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
                660                 665                 670
Tyr His Thr Gln Met Leu Arg Val Arg Glu Phe Ile Arg Phe His Gln
            675                 680                 685
Ile Pro Asn Pro Leu Arg Gln Arg Leu Glu Glu Tyr Phe Gln His Ala
            690                 695                 700
Trp Ser Tyr Thr Asn Gly Ile Asp Met Asn Ala Val Leu Lys Gly Phe
705                 710                 715                 720
Pro Glu Cys Leu Gln Ala Asp Ile Cys Leu His Leu Asn Arg Ser Leu
                725                 730                 735
Leu Gln His Cys Lys Pro Phe Arg Gly Ala Thr Lys Gly Cys Leu Arg
                740                 745                 750
Ala Leu Ala Met Lys Phe Lys Thr Thr His Ala Pro Pro Gly Asp Thr
            755                 760                 765
Leu Val His Ala Gly Asp Leu Leu Thr Ala Leu Tyr Phe Ile Ser Arg
            770                 775                 780
Gly Ser Ile Glu Ile Leu Arg Gly Asp Val Val Ala Ile Leu Gly
785                 790                 795                 800
Lys Asn Asp Ile Phe Gly Glu Pro Leu Asn Leu Tyr Ala Arg Pro Gly
                805                 810                 815
Lys Ser Asn Gly Asp Val Arg Ala Leu Thr Tyr Cys Asp Leu His Lys
            820                 825                 830
Ile His Arg Asp Asp Leu Leu Glu Val Leu Asp Met Tyr Pro Glu Phe
            835                 840                 845
Ser Asp His Phe Trp Ser Ser Leu Glu Ile Thr Phe Asn Leu Arg Asp
            850                 855                 860
Thr Asn Met Ile Pro Gly Ser Pro Gly Ser Thr Glu Leu Glu Gly Gly
865                 870                 875                 880
Phe Ser Arg Gln Arg Lys Arg Lys Leu Ser Phe Arg Arg Thr Asp
                885                 890                 895
```

-continued

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
        915                 920                 925

Glu Ser Pro Ser Ser Gly Pro Ser Ser Pro Glu Ser Ser Glu Asp Glu
    930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
        995                 1000                1005

Tyr Gln Glu Leu Pro Arg Cys Pro Ala Pro Thr Pro Ser Leu Leu Asn
    1010                1015                1020

Ile Pro Leu Ser Ser Pro Gly Arg Arg Pro Arg Gly Asp Val Glu Ser
1025                1030                1035                1040

Arg Leu Asp Ala Leu Gln Arg Gln Leu Asn Arg Leu Glu Thr Arg Leu
                1045                1050                1055

Ser Ala Asp Met Ala Thr Val Leu Gln Leu Leu Gln Arg Gln Met Thr
            1060                1065                1070

Leu Val Pro Pro Ala Tyr Ser Ala Val Thr Thr Pro Gly Pro Gly Pro
        1075                1080                1085

Thr Ser Thr Ser Pro Leu Leu Pro Val Ser Pro Leu Pro Thr Leu Thr
    1090                1095                1100

Leu Asp Ser Leu Ser Gln Val Ser Gln Phe Met Ala Cys Glu Glu Leu
1105                1110                1115                1120

Pro Pro Gly Ala Pro Glu Leu Pro Gln Glu Gly Pro Thr Arg Arg Leu
                1125                1130                1135

Ser Leu Pro Gly Gln Leu Gly Ala Leu Thr Ser Gln Pro Leu His Arg
            1140                1145                1150

His Gly Ser Asp Pro Gly Ser
        1155

<210> SEQ ID NO 3
<211> LENGTH: 3950
<212> TYPE: DNA
<213> ORGANISM: Homo sapiens
<220> FEATURE:
<221> NAME/KEY: CDS
<222> LOCATION: (67)..(3543)

<400> SEQUENCE: 3
agcctagtgc tgggccgggc cgggccgggg tgggtggggg cccgcccggc cgcccatggg      60 ctcagg atg ccg gtg cgg agg ggc cac gtc gcg ccg cag aac acc ttc       108
       Met Pro Val Arg Arg Gly His Val Ala Pro Gln Asn Thr Phe
       1               5                  10 ctg gac acc atc atc cgc aag ttt gag ggc cag agc cgt aag ttc atc      156
Leu Asp Thr Ile Ile Arg Lys Phe Glu Gly Gln Ser Arg Lys Phe Ile
15                  20                  25                  30 atc gcc aac gct cgg gtg gag aac tgc gcc gtc atc tac tgc aac gac      204
Ile Ala Asn Ala Arg Val Glu Asn Cys Ala Val Ile Tyr Cys Asn Asp
                35                  40                  45 ggc ttc tgc gag ctg tgc ggc tac tcg cgg gcc gag gtg atg cag cga      252
Gly Phe Cys Glu Leu Cys Gly Tyr Ser Arg Ala Glu Val Met Gln Arg -continued

```
                50                      55                      60
ccc tgc acc tgc gac ttc ctg cac ggg ccg cgc acg cag cgc cgc gct     300
Pro Cys Thr Cys Asp Phe Leu His Gly Pro Arg Thr Gln Arg Arg Ala
             65                      70                      75 gcc gcg cag atc gcg cag gca ctg ctg ggc gcc gag gag cgc aaa gtg     348
Ala Ala Gln Ile Ala Gln Ala Leu Leu Gly Ala Glu Glu Arg Lys Val
         80                      85                      90 gaa atc gcc ttc tac cgg aaa gat ggg agc tgc ttc cta tgt ctg gtg     396
Glu Ile Ala Phe Tyr Arg Lys Asp Gly Ser Cys Phe Leu Cys Leu Val
 95                     100                     105                     110 gat gtg gtg ccc gtg aag aac gag gat ggg gct gtc atc atg ttc atc     444
Asp Val Val Pro Val Lys Asn Glu Asp Gly Ala Val Ile Met Phe Ile
                    115                     120                     125 ctc aat ttc gag gtg gtg atg gag aag gac atg gtg ggg tcc ccg gct     492
Leu Asn Phe Glu Val Val Met Glu Lys Asp Met Val Gly Ser Pro Ala
            130                     135                     140 cat gac acc aac cac cgg ggc ccc ccc acc agc tgg ctg gcc cca ggc     540
His Asp Thr Asn His Arg Gly Pro Pro Thr Ser Trp Leu Ala Pro Gly
        145                     150                     155 cgc gcc aag acc ttc cgc ctg aag ctg ccc gcg ctg ctg gcg ctg acg     588
Arg Ala Lys Thr Phe Arg Leu Lys Leu Pro Ala Leu Leu Ala Leu Thr
    160                     165                     170 gcc cgg gag tcg tcg gtg cgg tcg ggc ggc gcg ggc ggc gcg ggc gcc     636
Ala Arg Glu Ser Ser Val Arg Ser Gly Gly Ala Gly Gly Ala Gly Ala
175                     180                     185                     190 ccg ggg gcc gtg gtg gtg gac gtg gac ctg acg ccc gcg gca ccc agc     684
Pro Gly Ala Val Val Val Asp Val Asp Leu Thr Pro Ala Ala Pro Ser
                    195                     200                     205 agc gag tcg ctg gcc ctg gac gaa gtg aca gcc atg gac aac cac gtg     732
Ser Glu Ser Leu Ala Leu Asp Glu Val Thr Ala Met Asp Asn His Val
                210                     215                     220 gca ggg ctc ggg ccc gcg gag gag cgg cgt gcg ctg gtg ggt ccc ggc     780
Ala Gly Leu Gly Pro Ala Glu Glu Arg Arg Ala Leu Val Gly Pro Gly
            225                     230                     235 tct ccg ccc cgc agc gcg ccc ggc cag ctc cca tcg ccc cgg gcg cac     828
Ser Pro Pro Arg Ser Ala Pro Gly Gln Leu Pro Ser Pro Arg Ala His
        240                     245                     250 agc ctc aac ccc gac gcc tcg ggc tcc agc tgc agc ctg gcc cgg acg     876
Ser Leu Asn Pro Asp Ala Ser Gly Ser Ser Cys Ser Leu Ala Arg Thr
255                     260                     265                     270 cgc tcc cga gaa agc tgc gcc agc gtg cgc cgc gcc tcg tcg gcc gac     924
Arg Ser Arg Glu Ser Cys Ala Ser Val Arg Arg Ala Ser Ser Ala Asp
                    275                     280                     285 gac atc gag gcc atg cgc gcc ggg gtg ctg ccc ccg cca ccg cgc cac     972
Asp Ile Glu Ala Met Arg Ala Gly Val Leu Pro Pro Pro Pro Arg His
                290                     295                     300 gcc agc acc ggg gcc atg cac cca ctg cgc agc ggc ttg ctc aac tcc    1020
Ala Ser Thr Gly Ala Met His Pro Leu Arg Ser Gly Leu Leu Asn Ser
            305                     310                     315 acc tcg gac tcc gac ctc gtg cgc tac cgc acc att agc aag att ccc    1068
Thr Ser Asp Ser Asp Leu Val Arg Tyr Arg Thr Ile Ser Lys Ile Pro
        320                     325                     330 caa atc acc ctc aac ttt gtg gac ctc aag ggc gac ccc ttc ttg gct    1116
Gln Ile Thr Leu Asn Phe Val Asp Leu Lys Gly Asp Pro Phe Leu Ala
335                     340                     345                     350 tcg ccc acc agt gac cgt gag atc ata gca cct aag ata aag gag cga    1164
Ser Pro Thr Ser Asp Arg Glu Ile Ile Ala Pro Lys Ile Lys Glu Arg
                    355                     360                     365 acc cac aat gtc act gag aag gtc acc cag gtc ctg tcc ctg ggc gcc    1212
Thr His Asn Val Thr Glu Lys Val Thr Gln Val Leu Ser Leu Gly Ala
```

```
                Thr His Asn Val Thr Glu Lys Val Thr Gln Val Leu Ser Leu Gly Ala
                            370                 375                 380 gac gtg ctg cct gag tac aag ctg cag gca ccg cgc atc cac cgc tgg          1260
Asp Val Leu Pro Glu Tyr Lys Leu Gln Ala Pro Arg Ile His Arg Trp
        385                 390                 395 acc atc ctg cat tac agc ccc ttc aag gcc gtg tgg gac tgg ctc atc          1308
Thr Ile Leu His Tyr Ser Pro Phe Lys Ala Val Trp Asp Trp Leu Ile
    400                 405                 410 ctg ctg ctg gtc atc tac acg gct gtc ttc aca ccc tac tcg gct gcc          1356
Leu Leu Leu Val Ile Tyr Thr Ala Val Phe Thr Pro Tyr Ser Ala Ala
415                 420                 425                 430 ttc ctg ctg aag gag acg gaa gaa ggc ccg cct gct acc gag tgt ggc          1404
Phe Leu Leu Lys Glu Thr Glu Glu Gly Pro Pro Ala Thr Glu Cys Gly
                435                 440                 445 tac gcc tgc cag ccg ctg gct gtg gtg gac ctc atc gtg gac atc atg          1452
Tyr Ala Cys Gln Pro Leu Ala Val Val Asp Leu Ile Val Asp Ile Met
            450                 455                 460 ttc att gtg gac atc ctc atc aac ttc cgc acc acc tac gtc aat gcc          1500
Phe Ile Val Asp Ile Leu Ile Asn Phe Arg Thr Thr Tyr Val Asn Ala
        465                 470                 475 aac gag gag gtg gtc agc cac ccc ggc cgc atc gcc gtc cac tac ttc          1548
Asn Glu Glu Val Val Ser His Pro Gly Arg Ile Ala Val His Tyr Phe
    480                 485                 490 aag ggc tgg ttc ctc atc gac atg gtg gcc gcc atc ccc ttc gac ctg          1596
Lys Gly Trp Phe Leu Ile Asp Met Val Ala Ala Ile Pro Phe Asp Leu
495                 500                 505                 510 ctc atc ttc ggc tct ggc tct gag gag ctg atc ggg ctg ctg aag act          1644
Leu Ile Phe Gly Ser Gly Ser Glu Glu Leu Ile Gly Leu Leu Lys Thr
                515                 520                 525 gcg cgg ctg ctg cgg ctg gtg cgc gtg gcg cgg aag ctg gat cgc tac          1692
Ala Arg Leu Leu Arg Leu Val Arg Val Ala Arg Lys Leu Asp Arg Tyr
            530                 535                 540 tca gag tac ggc gcg gcc gtg ctg ttc ttg ctc atg tgc acc ttt gcg          1740
Ser Glu Tyr Gly Ala Ala Val Leu Phe Leu Leu Met Cys Thr Phe Ala
        545                 550                 555 ctc atc gcg cac tgg cta gcc tgc atc tgg tac gcc atc ggc aac atg          1788
Leu Ile Ala His Trp Leu Ala Cys Ile Trp Tyr Ala Ile Gly Asn Met
    560                 565                 570 gag cag cca cac atg gac tca cgc atc ggc tgg ctg cac aac ctg ggc          1836
Glu Gln Pro His Met Asp Ser Arg Ile Gly Trp Leu His Asn Leu Gly
575                 580                 585                 590 gac cag ata ggc aaa ccc tac aac agc agc ggc ctg ggc ggc ccc tcc          1884
Asp Gln Ile Gly Lys Pro Tyr Asn Ser Ser Gly Leu Gly Gly Pro Ser
                595                 600                 605 atc aag gac aag tat gtg acg gcg ctc tac ttc acc ttc agc agc ctc          1932
Ile Lys Asp Lys Tyr Val Thr Ala Leu Tyr Phe Thr Phe Ser Ser Leu
            610                 615                 620 acc agt gtg ggc ttc ggc aac gtc tct ccc aac acc aac tca gag aag          1980
Thr Ser Val Gly Phe Gly Asn Val Ser Pro Asn Thr Asn Ser Glu Lys
        625                 630                 635 atc ttc tcc atc tgc gtc atg ctc att ggc tcc ctc atg tat gct agc          2028
Ile Phe Ser Ile Cys Val Met Leu Ile Gly Ser Leu Met Tyr Ala Ser
    640                 645                 650 atc ttc ggc aac gtg tcg gcc atc atc cag cgg ctg tac tcg ggc aca          2076
Ile Phe Gly Asn Val Ser Ala Ile Ile Gln Arg Leu Tyr Ser Gly Thr
655                 660                 665                 670 gcc cgc tac cac aca cag atg ctg cgg gtg cgg gag ttc atc cgc ttc          2124
Ala Arg Tyr His Thr Gln Met Leu Arg Val Arg Glu Phe Ile Arg Phe
                675                 680                 685
```

```
cac cag atc ccc aat ccc ctg cgc cag cgc ctc gag gag tac ttc cag    2172
His Gln Ile Pro Asn Pro Leu Arg Gln Arg Leu Glu Glu Tyr Phe Gln
            690                 695                 700 cac gcc tgg tcc tac acc aac ggc atc gac atg aac gcg gtg ctg aag    2220
His Ala Trp Ser Tyr Thr Asn Gly Ile Asp Met Asn Ala Val Leu Lys
        705                 710                 715 ggc ttc cct gag tgc ctg cag gct gac atc tgc ctg cac ctg aac cgc    2268
Gly Phe Pro Glu Cys Leu Gln Ala Asp Ile Cys Leu His Leu Asn Arg
    720                 725                 730 tca ctg ctg cag cac tgc aaa ccc ttc cga ggg gcc acc aag ggc tgc    2316
Ser Leu Leu Gln His Cys Lys Pro Phe Arg Gly Ala Thr Lys Gly Cys
735                 740                 745                 750 ctt cgg gcc ctg gcc atg aag ttc aag acc aca cat gca ccg cca ggg    2364
Leu Arg Ala Leu Ala Met Lys Phe Lys Thr Thr His Ala Pro Pro Gly
                755                 760                 765 gac aca ctg gtg cat gct ggg gac ctc ctc acc gcc ctg tac ttc atc    2412
Asp Thr Leu Val His Ala Gly Asp Leu Leu Thr Ala Leu Tyr Phe Ile
            770                 775                 780 tcc cgg ggc tcc atc gag atc ctg cgg ggc gac gtc gtc gtg gcc atc    2460
Ser Arg Gly Ser Ile Glu Ile Leu Arg Gly Asp Val Val Val Ala Ile
        785                 790                 795 ctg ggg aag aat gac atc ttt ggg gag cct ctg aac ctg tat gca agg    2508
Leu Gly Lys Asn Asp Ile Phe Gly Glu Pro Leu Asn Leu Tyr Ala Arg
    800                 805                 810 cct ggc aag tcg aac ggg gat gtg cgg gcc ctc acc tac tgt gac cta    2556
Pro Gly Lys Ser Asn Gly Asp Val Arg Ala Leu Thr Tyr Cys Asp Leu
815                 820                 825                 830 cac aag atc cat cgg gac gac ctg ctg gag gtg ctg gac atg tac cct    2604
His Lys Ile His Arg Asp Asp Leu Leu Glu Val Leu Asp Met Tyr Pro
                835                 840                 845 gag ttc tcc gac cac ttc tgg tcc agc ctg gag atc acc ttc aac ctg    2652
Glu Phe Ser Asp His Phe Trp Ser Ser Leu Glu Ile Thr Phe Asn Leu
            850                 855                 860 cga gat acc aac atg atc ccg ggc tcc ccc ggc agt acg gag tta gag    2700
Arg Asp Thr Asn Met Ile Pro Gly Ser Pro Gly Ser Thr Glu Leu Glu
        865                 870                 875 ggt ggc ttc agt cgg caa cgc aag cgc aag ttg tcc ttc cgc agg cgc    2748
Gly Gly Phe Ser Arg Gln Arg Lys Arg Lys Leu Ser Phe Arg Arg Arg
    880                 885                 890 acg gac aag gac acg gag cag cca ggg gag gtg tcg gcc ttg ggg ccg    2796
Thr Asp Lys Asp Thr Glu Gln Pro Gly Glu Val Ser Ala Leu Gly Pro
895                 900                 905                 910 ggc cgg gcg ggg gca ggg ccg agt agc cgg ggc cgg ccg ggg ggg ccg    2844
Gly Arg Ala Gly Ala Gly Pro Ser Ser Arg Gly Arg Pro Gly Gly Pro
                915                 920                 925 tgg ggg gag agc ccg tcc agt ggc ccc tcc agc cct gag agc agt gag    2892
Trp Gly Glu Ser Pro Ser Ser Gly Pro Ser Ser Pro Glu Ser Ser Glu
            930                 935                 940 gat gag ggc cca ggc cgc agc tcc agc ccc ctc cgc ctg gtg ccc ttc    2940
Asp Glu Gly Pro Gly Arg Ser Ser Ser Pro Leu Arg Leu Val Pro Phe
        945                 950                 955 tcc agc ccc agg ccc ccc gga gag ccg ccg ggt ggg gag ccc ctg atg    2988
Ser Ser Pro Arg Pro Pro Gly Glu Pro Pro Gly Gly Glu Pro Leu Met
    960                 965                 970 gag gac tgc gag aag agc agc gac act tgc aac ccc ctg tca ggc gcc    3036
Glu Asp Cys Glu Lys Ser Ser Asp Thr Cys Asn Pro Leu Ser Gly Ala
975                 980                 985                 990 ttc tca gga gtg tcc aac att ttc agc ttc tgg ggg gac agt cgg ggc    3084
Phe Ser Gly Val Ser Asn Ile Phe Ser Phe Trp Gly Asp Ser Arg Gly
                995                 1000                1005
```

```
cgc cag tac cag gag ctc cct cga tgc ccc gcc ccc acc ccc agc ctc     3132
Arg Gln Tyr Gln Glu Leu Pro Arg Cys Pro Ala Pro Thr Pro Ser Leu
             1010                1015                1020 ctc aac atc ccc ctc tcc agc ccg ggt cgg cgg ccc cgg ggc gac gtg     3180
Leu Asn Ile Pro Leu Ser Ser Pro Gly Arg Arg Pro Arg Gly Asp Val
         1025                1030                1035 gag agc agg ctg gat gcc ctc cag cgc cag ctc aac agg ctg gag acc     3228
Glu Ser Arg Leu Asp Ala Leu Gln Arg Gln Leu Asn Arg Leu Glu Thr
     1040                1045                1050 cgg ctg agt gca gac atg gcc act gtc ctg cag ctg cta cag agg cag     3276
Arg Leu Ser Ala Asp Met Ala Thr Val Leu Gln Leu Leu Gln Arg Gln
1055                1060                1065                1070 atg acg ctg gtc ccg ccc gcc tac agt gct gtg acc acc ccg ggg cct     3324
Met Thr Leu Val Pro Pro Ala Tyr Ser Ala Val Thr Thr Pro Gly Pro
                 1075                1080                1085 ggc ccc act tcc aca tcc ccg ctg ttg ccc gtc agc ccc ctc ccc acc     3372
Gly Pro Thr Ser Thr Ser Pro Leu Leu Pro Val Ser Pro Leu Pro Thr
             1090                1095                1100 ctc acc ttg gac tcg ctt tct cag gtt tcc cag ttc atg gcg tgt gag     3420
Leu Thr Leu Asp Ser Leu Ser Gln Val Ser Gln Phe Met Ala Cys Glu
         1105                1110                1115 gag ctg ccc ccg ggg gcc cca gag ctt ccc caa gaa ggc ccc aca cga     3468
Glu Leu Pro Pro Gly Ala Pro Glu Leu Pro Gln Glu Gly Pro Thr Arg
     1120                1125                1130 cgc ctc tcc cta ccg ggc cag ctg ggg gcc ctc acc tcc cag ccc ctg     3516
Arg Leu Ser Leu Pro Gly Gln Leu Gly Ala Leu Thr Ser Gln Pro Leu
1135                1140                1145                1150 cac aga cac ggc tcg gac ccg ggc agt tagtggggct gcccagtgtg           3563
His Arg His Gly Ser Asp Pro Gly Ser
                 1155 gacacgtggc tcacccaggg atcaaggcgc tgctgggccg ctccccttgg aggccctgct   3623 caggaggccc tgaccgtgga aggggagagg aactcgaaag cacagctcct cccccagccc   3683 ttgggaccat cttctcctgc agtcccctgg gccccagtga gagggcagg ggcagggccg    3743 gcagtaggtg gggcctgtgg tcccccacact gccctgaggg cattagctgg tctaactgcc  3803 cggaggcacc cggccctggg ccttaggcac ctcaaggact tttctgctat ttactgctct   3863 tattgttaag gataataatt aaggatcata tgaataatta atgaagatgc tgatgactat   3923 gaataataaa taattatcct gaggaga                                       3950

<210> SEQ ID NO 4
<211> LENGTH: 1159
<212> TYPE: PRT
<213> ORGANISM: Homo sapiens

<400> SEQUENCE: 4

Met Pro Val Arg Arg Gly His Val Ala Pro Gln Asn Thr Phe Leu Asp
 1               5                  10                  15

Thr Ile Ile Arg Lys Phe Glu Gly Gln Ser Arg Lys Phe Ile Ile Ala
             20                  25                  30

Asn Ala Arg Val Glu Asn Cys Ala Val Ile Tyr Cys Asn Asp Gly Phe
         35                  40                  45

Cys Glu Leu Cys Gly Tyr Ser Arg Ala Glu Val Met Gln Arg Pro Cys
     50                  55                  60

Thr Cys Asp Phe Leu His Gly Pro Arg Thr Gln Arg Arg Ala Ala Ala
 65                  70                  75                  80

Gln Ile Ala Gln Ala Leu Leu Gly Ala Glu Glu Arg Lys Val Glu Ile
```

-continued

```
                85                  90                  95
Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
            130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Ala Gly Gly Ala Gly Ala Pro Gly
                180                 185                 190

Ala Val Val Asp Val Asp Leu Thr Pro Ala Ala Pro Ser Ser Glu
                195                 200                 205

Ser Leu Ala Leu Asp Glu Val Thr Ala Met Asp Asn His Val Ala Gly
            210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
                260                 265                 270

Arg Glu Ser Cys Ala Ser Val Arg Arg Ala Ser Ser Ala Asp Asp Ile
            275                 280                 285

Glu Ala Met Arg Ala Gly Val Leu Pro Pro Pro Arg His Ala Ser
290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
            355                 360                 365

Asn Val Thr Glu Lys Val Thr Gln Val Leu Ser Leu Gly Ala Asp Val
370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
            405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
            435                 440                 445

Cys Gln Pro Leu Ala Val Val Asp Leu Ile Val Asp Ile Met Phe Ile
450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
            500                 505                 510
```

-continued

```
Phe Gly Ser Gly Ser Glu Glu Leu Ile Gly Leu Leu Lys Thr Ala Arg
            515                 520                 525

Leu Leu Arg Leu Val Arg Val Ala Arg Lys Leu Asp Arg Tyr Ser Glu
        530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Pro Ser Ile Lys
        595                 600                 605

Asp Lys Tyr Val Thr Ala Leu Tyr Phe Thr Phe Ser Ser Leu Thr Ser
        610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
            660                 665                 670

Tyr His Thr Gln Met Leu Arg Val Arg Glu Phe Ile Arg Phe His Gln
        675                 680                 685

Ile Pro Asn Pro Leu Arg Gln Arg Leu Glu Glu Tyr Phe Gln His Ala
        690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
        755                 760                 765

Leu Val His Ala Gly Asp Leu Leu Thr Ala Leu Tyr Phe Ile Ser Arg
        770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
            820                 825                 830

Ile His Arg Asp Asp Leu Leu Glu Val Leu Asp Met Tyr Pro Glu Phe
        835                 840                 845

Ser Asp His Phe Trp Ser Ser Leu Glu Ile Thr Phe Asn Leu Arg Asp
        850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
        915                 920                 925
```

```
Glu Ser Pro Ser Ser Gly Pro Ser Ser Pro Glu Ser Ser Glu Asp Glu
    930                 935                 940
Gly Pro Gly Arg Ser Ser Pro Leu Arg Leu Val Pro Phe Ser Ser
945                 950                 955                 960
Pro Arg Pro Pro Gly Glu Pro Gly Gly Glu Pro Leu Met Glu Asp
                965                 970                 975
Cys Glu Lys Ser Ser Asp Thr Cys Asn Pro Leu Ser Gly Ala Phe Ser
            980                 985                 990
Gly Val Ser Asn Ile Phe Ser Phe Trp Gly Asp Ser Arg Gly Arg Gln
        995                 1000                1005
Tyr Gln Glu Leu Pro Arg Cys Pro Ala Pro Thr Pro Ser Leu Leu Asn
    1010                1015                1020
Ile Pro Leu Ser Ser Pro Gly Arg Arg Pro Arg Gly Asp Val Glu Ser
1025                1030                1035                1040
Arg Leu Asp Ala Leu Gln Arg Gln Leu Asn Arg Leu Glu Thr Arg Leu
                1045                1050                1055
Ser Ala Asp Met Ala Thr Val Leu Gln Leu Leu Gln Arg Gln Met Thr
                1060                1065                1070
Leu Val Pro Pro Ala Tyr Ser Ala Val Thr Thr Pro Gly Pro Gly Pro
            1075                1080                1085
Thr Ser Thr Ser Pro Leu Leu Pro Val Ser Pro Leu Pro Thr Leu Thr
    1090                1095                1100
Leu Asp Ser Leu Ser Gln Val Ser Gln Phe Met Ala Cys Glu Glu Leu
1105                1110                1115                1120
Pro Pro Gly Ala Pro Glu Leu Pro Gln Glu Gly Pro Thr Arg Arg Leu
                1125                1130                1135
Ser Leu Pro Gly Gln Leu Gly Ala Leu Thr Ser Gln Pro Leu His Arg
            1140                1145                1150
His Gly Ser Asp Pro Gly Ser
        1155

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence:Hypothetical
      sequence for the example of calculating homology.

<400> SEQUENCE: 5
accgtagcta cgtacgtata tagaaagggc gcgatcgtcg tcgcgtatga cgacttagca    60
tgc                                                                 63

<210> SEQ ID NO 6
<211> LENGTH: 130
<212> TYPE: DNA
<213> ORGANISM: Artificial Sequence
<220> FEATURE:
<223> OTHER INFORMATION: Description of Artificial Sequence:Hypothetical
      sequence for example of calculating homology.

<400> SEQUENCE: 6
accggtagct acgtacgtta tttagaaagg ggtgtgtgtg tgtgtgtaaa ccggggtttt    60
cgggatcgtc cgtcgcgtat gacgacttag ccatgcacgg tatatcgtat taggactagc   120
gattgactag                                                         130

<210> SEQ ID NO 7
```

-continued

```
<211> LENGTH: 20
<212> TYPE: DNA
<213> ORGANISM: Homo sapiens

<400> SEQUENCE: 7
gctgggccgc tccccttgga                                               20

<210> SEQ ID NO 8
<211> LENGTH: 20
<212> TYPE: DNA
<213> ORGANISM: Homo sapiens

<400> SEQUENCE: 8
gcatcttcat taattattca                                               20

<210> SEQ ID NO 9
<211> LENGTH: 20
<212> TYPE: DNA
<213> ORGANISM: Homo sapiens

<400> SEQUENCE: 9
gacgtgctgc ctgagtacaa                                               20

<210> SEQ ID NO 10
<211> LENGTH: 22
<212> TYPE: DNA
<213> ORGANISM: Homo sapiens

<400> SEQUENCE: 10
ttcctgctga aggagacgga ag                                            22

<210> SEQ ID NO 11
<211> LENGTH: 21
<212> TYPE: DNA
<213> ORGANISM: Homo sapiens

<400> SEQUENCE: 11
accacctacg tcaatgccaa c                                             21

<210> SEQ ID NO 12
<211> LENGTH: 21
<212> TYPE: DNA
<213> ORGANISM: Homo sapiens

<400> SEQUENCE: 12
tgccccatca acggaatgtg c                                             21

<210> SEQ ID NO 13
<211> LENGTH: 19
<212> TYPE: DNA
<213> ORGANISM: Homo sapiens

<400> SEQUENCE: 13
gatcgctact cagagtacg                                                19

<210> SEQ ID NO 14
<211> LENGTH: 22
<212> TYPE: DNA
<213> ORGANISM: Homo sapiens

<400> SEQUENCE: 14
gcctgggcgg cccctccatc aa                                            22
```

```
<210> SEQ ID NO 15
<211> LENGTH: 21
<212> TYPE: DNA
<213> ORGANISM: Homo sapiens

<400> SEQUENCE: 15
cacctcctcg ttggcattga c                                            21

<210> SEQ ID NO 16
<211> LENGTH: 25
<212> TYPE: DNA
<213> ORGANISM: Homo sapiens

<400> SEQUENCE: 16
gtcgaagggg atggcggcca ccatg                                        25

<210> SEQ ID NO 17
<211> LENGTH: 23
<212> TYPE: DNA
<213> ORGANISM: Homo sapiens

<400> SEQUENCE: 17
tacaccacct gcctccttgc tga                                          23

<210> SEQ ID NO 18
<211> LENGTH: 21
<212> TYPE: DNA
<213> ORGANISM: Homo sapiens

<400> SEQUENCE: 18
gccgcgccgt actctgagta g                                            21

<210> SEQ ID NO 19
<211> LENGTH: 23
<212> TYPE: DNA
<213> ORGANISM: Homo sapiens

<400> SEQUENCE: 19
cagccagccg atgcgtgagt cca                                          23

<210> SEQ ID NO 20
<211> LENGTH: 21
<212> TYPE: DNA
<213> ORGANISM: Homo sapiens

<400> SEQUENCE: 20
gcccgcccct gggcacactc a                                            21

<210> SEQ ID NO 21
<211> LENGTH: 19
<212> TYPE: DNA
<213> ORGANISM: Homo sapiens

<400> SEQUENCE: 21
cagcatctgt gtgtggtag                                               19

<210> SEQ ID NO 22
<211> LENGTH: 19
<212> TYPE: DNA
<213> ORGANISM: Homo sapiens

<400> SEQUENCE: 22
ggcatttcca gtccagtgc                                               19
```

```
<210> SEQ ID NO 23
<211> LENGTH: 20
<212> TYPE: DNA
<213> ORGANISM: Homo sapiens

<400> SEQUENCE: 23
cctggccatg aagttcaaga                                                    20

<210> SEQ ID NO 24
<211> LENGTH: 20
<212> TYPE: DNA
<213> ORGANISM: Homo sapiens

<400> SEQUENCE: 24
gcactgcaaa cccttccgag                                                    20

<210> SEQ ID NO 25
<211> LENGTH: 22
<212> TYPE: DNA
<213> ORGANISM: Homo sapiens

<400> SEQUENCE: 25
gtcggagaac tcagggtaca tg                                                 22

<210> SEQ ID NO 26
<211> LENGTH: 10
<212> TYPE: DNA
<213> ORGANISM: Homo sapiens

<400> SEQUENCE: 26
atgccggtgc                                                               10

<210> SEQ ID NO 27
<211> LENGTH: 20
<212> TYPE: DNA
<213> ORGANISM: Homo sapiens

<400> SEQUENCE: 27
gagggccaga gtgagtgggg                                                    20

<210> SEQ ID NO 28
<211> LENGTH: 20
<212> TYPE: DNA
<213> ORGANISM: Homo sapiens

<400> SEQUENCE: 28
gccccccatg gccgtaagtt                                                    20

<210> SEQ ID NO 29
<211> LENGTH: 20
<212> TYPE: DNA
<213> ORGANISM: Homo sapiens

<400> SEQUENCE: 29
cggaaagatg gtaggagcgg                                                    20

<210> SEQ ID NO 30
<211> LENGTH: 20
<212> TYPE: DNA
<213> ORGANISM: Homo sapiens

<400> SEQUENCE: 30
cactctgcag ggagctgctt                                                    20
```

<210> SEQ ID NO 31
<211> LENGTH: 20
<212> TYPE: DNA
<213> ORGANISM: Homo sapiens

<400> SEQUENCE: 31
ctggccccag gtaagtgtac						20

<210> SEQ ID NO 32
<211> LENGTH: 20
<212> TYPE: DNA
<213> ORGANISM: Homo sapiens

<400> SEQUENCE: 32
tctcccgcag gccgcgccaa						20

<210> SEQ ID NO 33
<211> LENGTH: 20
<212> TYPE: DNA
<213> ORGANISM: Homo sapiens

<400> SEQUENCE: 33
gccagcaccg gtgagggcgc						20

<210> SEQ ID NO 34
<211> LENGTH: 20
<212> TYPE: DNA
<213> ORGANISM: Homo sapiens

<400> SEQUENCE: 34
ctccacctag gggccatgca						20

<210> SEQ ID NO 35
<211> LENGTH: 20
<212> TYPE: DNA
<213> ORGANISM: Homo sapiens

<400> SEQUENCE: 35
ggtcacccag gtaggcgccc						20

<210> SEQ ID NO 36
<211> LENGTH: 20
<212> TYPE: DNA
<213> ORGANISM: Homo sapiens

<400> SEQUENCE: 36
ccgggtgcag gtcctgtccc						20

<210> SEQ ID NO 37
<211> LENGTH: 20
<212> TYPE: DNA
<213> ORGANISM: Homo sapiens

<400> SEQUENCE: 37
ctctgaggag gtggggtcag						20

<210> SEQ ID NO 38
<211> LENGTH: 20
<212> TYPE: DNA
<213> ORGANISM: Homo sapiens

<400> SEQUENCE: 38

| | |
|---|---|
| tgtcccccag ctgatcgggc | 20 |

<210> SEQ ID NO 39
<211> LENGTH: 20
<212> TYPE: DNA
<213> ORGANISM: Homo sapiens

<400> SEQUENCE: 39

| | |
|---|---|
| ctcattggct gtgagtgtgc | 20 |

<210> SEQ ID NO 40
<211> LENGTH: 20
<212> TYPE: DNA
<213> ORGANISM: Homo sapiens

<400> SEQUENCE: 40

| | |
|---|---|
| acgcccccag ccctcatgta | 20 |

<210> SEQ ID NO 41
<211> LENGTH: 20
<212> TYPE: DNA
<213> ORGANISM: Homo sapiens

<400> SEQUENCE: 41

| | |
|---|---|
| catgaacgcg gtgaggccac | 20 |

<210> SEQ ID NO 42
<211> LENGTH: 20
<212> TYPE: DNA
<213> ORGANISM: Homo sapiens

<400> SEQUENCE: 42

| | |
|---|---|
| ctgcccccag gtgctgaagg | 20 |

<210> SEQ ID NO 43
<211> LENGTH: 20
<212> TYPE: DNA
<213> ORGANISM: Homo sapiens

<400> SEQUENCE: 43

| | |
|---|---|
| gccatcctgg gtatggggtg | 20 |

<210> SEQ ID NO 44
<211> LENGTH: 20
<212> TYPE: DNA
<213> ORGANISM: Homo sapiens

<400> SEQUENCE: 44

| | |
|---|---|
| tggcctccag ggaagaatga | 20 |

<210> SEQ ID NO 45
<211> LENGTH: 20
<212> TYPE: DNA
<213> ORGANISM: Homo sapiens

<400> SEQUENCE: 45

| | |
|---|---|
| cctgcgagat gtgagttggc | 20 |

<210> SEQ ID NO 46
<211> LENGTH: 20
<212> TYPE: DNA
<213> ORGANISM: Homo sapiens

<400> SEQUENCE: 46
ttggttccag accaacatga                                              20

<210> SEQ ID NO 47
<211> LENGTH: 20
<212> TYPE: DNA
<213> ORGANISM: Homo sapiens

<400> SEQUENCE: 47
acggacaagg gtgaggcggg                                              20

<210> SEQ ID NO 48
<211> LENGTH: 20
<212> TYPE: DNA
<213> ORGANISM: Homo sapiens

<400> SEQUENCE: 48
tttcccacag acacggagca                                              20

<210> SEQ ID NO 49
<211> LENGTH: 20
<212> TYPE: DNA
<213> ORGANISM: Homo sapiens

<400> SEQUENCE: 49
cccctgtcag gtatcccggg                                              20

<210> SEQ ID NO 50
<211> LENGTH: 20
<212> TYPE: DNA
<213> ORGANISM: Homo sapiens

<400> SEQUENCE: 50
ctggctgcag gcgccttctc                                              20

<210> SEQ ID NO 51
<211> LENGTH: 20
<212> TYPE: DNA
<213> ORGANISM: Homo sapiens

<400> SEQUENCE: 51
agctcaacag gtgagggagt                                              20

<210> SEQ ID NO 52
<211> LENGTH: 20
<212> TYPE: DNA
<213> ORGANISM: Homo sapiens

<400> SEQUENCE: 52
cctgccccag gctggagacc                                              20

<210> SEQ ID NO 53
<211> LENGTH: 20
<212> TYPE: DNA
<213> ORGANISM: Homo sapiens

<400> SEQUENCE: 53
gctttctcag gtaagctcca                                              20

<210> SEQ ID NO 54
<211> LENGTH: 20
<212> TYPE: DNA
<213> ORGANISM: Homo sapiens

```
<400> SEQUENCE: 54
tgtattgcag gtttcccagt                                               20

<210> SEQ ID NO 55
<211> LENGTH: 10
<212> TYPE: DNA
<213> ORGANISM: Homo sapiens

<400> SEQUENCE: 55
gggcagttag                                                          10

<210> SEQ ID NO 56
<211> LENGTH: 19
<212> TYPE: DNA
<213> ORGANISM: Homo sapiens

<400> SEQUENCE: 56
gggccacccg aagcctagt                                                19

<210> SEQ ID NO 57
<211> LENGTH: 18
<212> TYPE: DNA
<213> ORGANISM: Homo sapiens

<400> SEQUENCE: 57
ccgtcccctc gccaaagc                                                 18

<210> SEQ ID NO 58
<211> LENGTH: 17
<212> TYPE: DNA
<213> ORGANISM: Homo sapiens

<400> SEQUENCE: 58
ccgcccatgg gctcagg                                                  17

<210> SEQ ID NO 59
<211> LENGTH: 20
<212> TYPE: DNA
<213> ORGANISM: Homo sapiens

<400> SEQUENCE: 59
catccacact cggaagagct                                               20

<210> SEQ ID NO 60
<211> LENGTH: 20
<212> TYPE: DNA
<213> ORGANISM: Homo sapiens

<400> SEQUENCE: 60
ggtcccgtca cgcgcactct                                               20

<210> SEQ ID NO 61
<211> LENGTH: 20
<212> TYPE: DNA
<213> ORGANISM: Homo sapiens

<400> SEQUENCE: 61
ttgaccccgc ccctggtcgt                                               20

<210> SEQ ID NO 62
<211> LENGTH: 20
<212> TYPE: DNA
<213> ORGANISM: Homo sapiens
```

```
<400> SEQUENCE: 62
gggctatgtc ctcccactct                                              20

<210> SEQ ID NO 63
<211> LENGTH: 22
<212> TYPE: DNA
<213> ORGANISM: Homo sapiens

<400> SEQUENCE: 63
agcctgccct aaagcaagta ca                                           22

<210> SEQ ID NO 64
<211> LENGTH: 19
<212> TYPE: DNA
<213> ORGANISM: Homo sapiens

<400> SEQUENCE: 64
ctccggggct gctcgggat                                               19

<210> SEQ ID NO 65
<211> LENGTH: 20
<212> TYPE: DNA
<213> ORGANISM: Homo sapiens

<400> SEQUENCE: 65
caccagcgca cgccgctcct                                              20

<210> SEQ ID NO 66
<211> LENGTH: 21
<212> TYPE: DNA
<213> ORGANISM: Homo sapiens

<400> SEQUENCE: 66
gccatggaca accacgtggc a                                            21

<210> SEQ ID NO 67
<211> LENGTH: 20
<212> TYPE: DNA
<213> ORGANISM: Homo sapiens

<400> SEQUENCE: 67
cccagaatgc agcaagcctg                                              20

<210> SEQ ID NO 68
<211> LENGTH: 20
<212> TYPE: DNA
<213> ORGANISM: Homo sapiens

<400> SEQUENCE: 68
ggcctgacca cgctgcctct                                              20

<210> SEQ ID NO 69
<211> LENGTH: 20
<212> TYPE: DNA
<213> ORGANISM: Homo sapiens

<400> SEQUENCE: 69
ccctctccaa gctcctccaa                                              20

<210> SEQ ID NO 70
<211> LENGTH: 20
<212> TYPE: DNA
```

<213> ORGANISM: Homo sapiens

<400> SEQUENCE: 70
cagagatgtc atcgctcctg                                          20

<210> SEQ ID NO 71
<211> LENGTH: 22
<212> TYPE: DNA
<213> ORGANISM: Homo sapiens

<400> SEQUENCE: 71
caggcgtagc cacactcggt ag                                       22

<210> SEQ ID NO 72
<211> LENGTH: 22
<212> TYPE: DNA
<213> ORGANISM: Homo sapiens

<400> SEQUENCE: 72
ttcctgctga aggagacgga ag                                       22

<210> SEQ ID NO 73
<211> LENGTH: 23
<212> TYPE: DNA
<213> ORGANISM: Homo sapiens

<400> SEQUENCE: 73
tacaccacct gcctccttgc tga                                      23

<210> SEQ ID NO 74
<211> LENGTH: 21
<212> TYPE: DNA
<213> ORGANISM: Homo sapiens

<400> SEQUENCE: 74
tgccccatca acggaatgtg c                                        21

<210> SEQ ID NO 75
<211> LENGTH: 22
<212> TYPE: DNA
<213> ORGANISM: Homo sapiens

<400> SEQUENCE: 75
gaagtagagc gccgtcacat ac                                       22

<210> SEQ ID NO 76
<211> LENGTH: 22
<212> TYPE: DNA
<213> ORGANISM: Homo sapiens

<400> SEQUENCE: 76
gcctgggcgg cccctccatc aa                                       22

<210> SEQ ID NO 77
<211> LENGTH: 21
<212> TYPE: DNA
<213> ORGANISM: Homo sapiens

<400> SEQUENCE: 77
agtttcctcc aacttgggtt c                                        21

<210> SEQ ID NO 78
<211> LENGTH: 19

```
<212> TYPE: DNA
<213> ORGANISM: Homo sapiens

<400> SEQUENCE: 78
gcagaggctg acggcccca                                                    19

<210> SEQ ID NO 79
<211> LENGTH: 21
<212> TYPE: DNA
<213> ORGANISM: Homo sapiens

<400> SEQUENCE: 79
acttgtttgc tgtgccaaga g                                                 21

<210> SEQ ID NO 80
<211> LENGTH: 22
<212> TYPE: DNA
<213> ORGANISM: Homo sapiens

<400> SEQUENCE: 80
atggtggagt ggagtgtggg tt                                                22

<210> SEQ ID NO 81
<211> LENGTH: 21
<212> TYPE: DNA
<213> ORGANISM: Homo sapiens

<400> SEQUENCE: 81
agaaggctcg cacctcttga g                                                 21

<210> SEQ ID NO 82
<211> LENGTH: 20
<212> TYPE: DNA
<213> ORGANISM: Homo sapiens

<400> SEQUENCE: 82
gagaggtgcc tgctgcctgg                                                   20

<210> SEQ ID NO 83
<211> LENGTH: 21
<212> TYPE: DNA
<213> ORGANISM: Homo sapiens

<400> SEQUENCE: 83
acagctggaa gcaggaggat g                                                 21

<210> SEQ ID NO 84
<211> LENGTH: 20
<212> TYPE: DNA
<213> ORGANISM: Homo sapiens

<400> SEQUENCE: 84
gggccctgat actgattttg                                                   20

<210> SEQ ID NO 85
<211> LENGTH: 21
<212> TYPE: DNA
<213> ORGANISM: Homo sapiens

<400> SEQUENCE: 85
gccctgtgaa gtccaaaaag c                                                 21

<210> SEQ ID NO 86
```

```
-continued

<211> LENGTH: 20
<212> TYPE: DNA
<213> ORGANISM: Homo sapiens

<400> SEQUENCE: 86
ccctgatact gattttggtt                                                   20

<210> SEQ ID NO 87
<211> LENGTH: 19
<212> TYPE: DNA
<213> ORGANISM: Homo sapiens

<400> SEQUENCE: 87
caccccgcct tccagctcc                                                    19

<210> SEQ ID NO 88
<211> LENGTH: 21
<212> TYPE: DNA
<213> ORGANISM: Homo sapiens

<400> SEQUENCE: 88
tgaggcccat tctctgtttc c                                                 21

<210> SEQ ID NO 89
<211> LENGTH: 21
<212> TYPE: DNA
<213> ORGANISM: Homo sapiens

<400> SEQUENCE: 89
gtagacgcac caccgctgcc a                                                 21

<210> SEQ ID NO 90
<211> LENGTH: 21
<212> TYPE: DNA
<213> ORGANISM: Homo sapiens

<400> SEQUENCE: 90
ctcacccagc tctgctctct g                                                 21

<210> SEQ ID NO 91
<211> LENGTH: 21
<212> TYPE: DNA
<213> ORGANISM: Homo sapiens

<400> SEQUENCE: 91
caccaggacc tggaccagac t                                                 21

<210> SEQ ID NO 92
<211> LENGTH: 20
<212> TYPE: DNA
<213> ORGANISM: Homo sapiens

<400> SEQUENCE: 92
gtggaggctg tcactggtgt                                                   20

<210> SEQ ID NO 93
<211> LENGTH: 21
<212> TYPE: DNA
<213> ORGANISM: Homo sapiens

<400> SEQUENCE: 93
gaggaagcag ggctggagct t                                                 21
```

```
<210> SEQ ID NO 94
<211> LENGTH: 22
<212> TYPE: DNA
<213> ORGANISM: Homo sapiens

<400> SEQUENCE: 94
tgcccatgct ctgtgtgtat tg                                              22

<210> SEQ ID NO 95
<211> LENGTH: 21
<212> TYPE: DNA
<213> ORGANISM: Homo sapiens

<400> SEQUENCE: 95
cggcccagca gcgccttgat c                                               21

<210> SEQ ID NO 96
<211> LENGTH: 45
<212> TYPE: DNA
<213> ORGANISM: Homo sapiens

<400> SEQUENCE: 96
tggttcctca tcgacatggt ggccgccatc cccttcgacc tgctc                     45

<210> SEQ ID NO 97
<211> LENGTH: 15
<212> TYPE: PRT
<213> ORGANISM: Homo sapiens

<400> SEQUENCE: 97

Trp Phe Leu Ile Asp Met Val Ala Ala Ile Pro Phe Asp Leu Leu
 1               5                  10                  15

<210> SEQ ID NO 98
<211> LENGTH: 54
<212> TYPE: DNA
<213> ORGANISM: Homo sapiens

<400> SEQUENCE: 98
gtcatctaca cggctgtctt cacaccctac tcggctgcct tcctgctgaa ggag           54

<210> SEQ ID NO 99
<211> LENGTH: 18
<212> TYPE: PRT
<213> ORGANISM: Homo sapiens

<400> SEQUENCE: 99

Val Ile Tyr Thr Ala Val Phe Thr Pro Tyr Ser Ala Ala Phe Leu Leu
 1               5                  10                  15

Lys Glu

<210> SEQ ID NO 100
<211> LENGTH: 48
<212> TYPE: DNA
<213> ORGANISM: Homo sapiens

<400> SEQUENCE: 100
gtcatctacc ggctgtcttc acaccctact cggctgcctt cctgctga                  48

<210> SEQ ID NO 101
<211> LENGTH: 15
<212> TYPE: PRT
<213> ORGANISM: Homo sapiens
```

```
<400> SEQUENCE: 101

Val Ile Tyr Arg Leu Ser Ser His Pro Thr Arg Leu Pro Ser Cys
 1               5                  10                  15

<210> SEQ ID NO 102
<211> LENGTH: 6
<212> TYPE: PRT
<213> ORGANISM: Homo sapiens

<400> SEQUENCE: 102

Leu Ile Ala His Trp Leu
 1               5

<210> SEQ ID NO 103
<211> LENGTH: 6
<212> TYPE: PRT
<213> ORGANISM: Homo sapiens

<400> SEQUENCE: 103

Leu Ile Val His Trp Leu
 1               5

<210> SEQ ID NO 104
<211> LENGTH: 6
<212> TYPE: PRT
<213> ORGANISM: Mus musculus

<400> SEQUENCE: 104

Leu Ala Ala His Trp Lys
 1               5

<210> SEQ ID NO 105
<211> LENGTH: 6
<212> TYPE: PRT
<213> ORGANISM: Rattus rattus

<400> SEQUENCE: 105

Leu Ala Ala His Trp Met
 1               5

<210> SEQ ID NO 106
<211> LENGTH: 6
<212> TYPE: PRT
<213> ORGANISM: Drosophila melanogaster

<400> SEQUENCE: 106

Leu Val Ala His Trp Leu
 1               5

<210> SEQ ID NO 107
<211> LENGTH: 6
<212> TYPE: PRT
<213> ORGANISM: Unknown
<220> FEATURE:
<223> OTHER INFORMATION: Description of Unknown Organism:See Warmke and
      Ganetzky, 1994.

<400> SEQUENCE: 107

Leu Ala Ala His Trp Leu
 1               5

<210> SEQ ID NO 108
<211> LENGTH: 7
<212> TYPE: PRT
<213> ORGANISM: Homo sapiens
```

```
<400> SEQUENCE: 108

Asp Ile Leu Ile Asn Phe Arg
1               5

<210> SEQ ID NO 109
<211> LENGTH: 7
<212> TYPE: PRT
<213> ORGANISM: Homo sapiens

<400> SEQUENCE: 109

Asp Ile Leu Ile Asp Phe Arg
1               5

<210> SEQ ID NO 110
<211> LENGTH: 7
<212> TYPE: PRT
<213> ORGANISM: Drosophila melanogaster

<400> SEQUENCE: 110

Asp Ile Val Leu Asn Phe His
1               5

<210> SEQ ID NO 111
<211> LENGTH: 7
<212> TYPE: PRT
<213> ORGANISM: Unknown
<220> FEATURE:
<223> OTHER INFORMATION: Description of Unknown Organism:See Warmke and
      Ganetzky, 1994.

<400> SEQUENCE: 111

Asp Ile Leu Leu Asn Phe Arg
1               5

<210> SEQ ID NO 112
<211> LENGTH: 8
<212> TYPE: PRT
<213> ORGANISM: Homo sapiens

<400> SEQUENCE: 112

Ser Val Gly Phe Gly Asn Val Ser
1               5

<210> SEQ ID NO 113
<211> LENGTH: 8
<212> TYPE: PRT
<213> ORGANISM: Homo sapiens

<400> SEQUENCE: 113

Ser Val Gly Phe Ser Asn Val Ser
1               5

<210> SEQ ID NO 114
<211> LENGTH: 8
<212> TYPE: PRT
<213> ORGANISM: Mus musculus

<400> SEQUENCE: 114

Ser Val Gly Phe Gly Asn Ile Ala
1               5

<210> SEQ ID NO 115
<211> LENGTH: 8
<212> TYPE: PRT
```

```
<213> ORGANISM: Drosophila melanogaster

<400> SEQUENCE: 115

Ser Val Gly Phe Gly Asn Val Ala
  1               5

<210> SEQ ID NO 116
<211> LENGTH: 8
<212> TYPE: PRT
<213> ORGANISM: Drosophila melanogaster

<400> SEQUENCE: 116

Thr Val Gly Tyr Gly Asp Met Thr
  1               5
```